US009637512B2

(12) United States Patent
Chun et al.

(10) Patent No.: US 9,637,512 B2
(45) Date of Patent: May 2, 2017

(54) NUCLEOSIDE PHOSPHORAMIDATES

(71) Applicant: GILEAD PHARMASSET LLC, Foster City, CA (US)

(72) Inventors: Byoung-Kwon Chun, Robbinsville, NJ (US); Ganapati Reddy Pamulapati, San Ramon, CA (US); Suguna Rachakonda, Twinsburg, OH (US); Bruce Ross, El Granada, CA (US); Michael Joseph Sofia, Doylestown, PA (US); Peiyuan Wang, Totowa, NJ (US); Hai-Ren Zhang, San Jose, CA (US)

(73) Assignee: Gilead Pharmasset LLC, Foster City, CA (US)

( * ) Notice: Subject to any disclaimer, the term of this patent is extended or adjusted under 35 U.S.C. 154(b) by 334 days.

(21) Appl. No.: 14/152,243

(22) Filed: Jan. 10, 2014

(65) Prior Publication Data
US 2014/0121366 A1 May 1, 2014

Related U.S. Application Data

(60) Continuation of application No. 13/732,725, filed on Jan. 2, 2013, now Pat. No. 9,206,217, which is a division of application No. 12/783,680, filed on May 20, 2010, now Pat. No. 8,642,756.

(60) Provisional application No. 61/319,513, filed on Mar. 31, 2010, provisional application No. 61/179,923, filed on May 20, 2009.

(51) Int. Cl.
| C07H 19/10 | (2006.01) |
| A61K 31/7072 | (2006.01) |
| A61K 45/00 | (2006.01) |
| C07F 9/24 | (2006.01) |
| A61K 31/716 | (2006.01) |
| C07H 17/02 | (2006.01) |
| C07F 9/6558 | (2006.01) |
| C07H 1/00 | (2006.01) |

(52) U.S. Cl.
CPC ......... *C07H 19/10* (2013.01); *A61K 31/7072* (2013.01); *A61K 31/716* (2013.01); *A61K 45/00* (2013.01); *C07F 9/24* (2013.01); *C07F 9/242* (2013.01); *C07F 9/65586* (2013.01); *C07H 1/00* (2013.01); *C07H 17/02* (2013.01)

(58) Field of Classification Search
None
See application file for complete search history.

(56) References Cited

U.S. PATENT DOCUMENTS

| 3,798,209 A | 3/1974 | Witkowski et al. |
| 3,852,267 A | 12/1974 | Meyer, Jr. et al. |
| RE29,835 E | 11/1978 | Witkowski et al. |
| 4,814,477 A | 3/1989 | Wijnberg et al. |
| 4,957,924 A | 9/1990 | Beauchamp |
| 5,026,687 A | 6/1991 | Yarchoan et al. |
| 5,118,820 A | 6/1992 | Hertel |
| 5,149,794 A | 9/1992 | Yatvin et al. |
| 5,157,027 A | 10/1992 | Biller et al. |
| 5,192,549 A | 3/1993 | Barenolz et al. |
| 5,194,654 A | 3/1993 | Hostetler et al. |
| 5,223,263 A | 6/1993 | Hostetler et al. |
| 5,256,641 A | 10/1993 | Yatvin et al. |
| 5,256,798 A | 10/1993 | Chou et al. |
| 5,372,808 A | 12/1994 | Blatt et al. |
| 5,376,380 A | 12/1994 | Kikuchi et al. |
| 5,405,598 A | 4/1995 | Schinazi et al. |
| 5,411,947 A | 5/1995 | Hostetler et al. |
| 5,420,266 A | 5/1995 | Britton et al. |
| 5,426,183 A | 6/1995 | Kjell |
| 5,453,499 A | 9/1995 | Chou et al. |
| 5,462,724 A | 10/1995 | Schinazi et al. |
| 5,463,092 A | 10/1995 | Hostetler et al. |
| 5,496,546 A | 3/1996 | Wang et al. |
| 5,538,865 A | 7/1996 | Reyes et al. |
| 5,543,389 A | 8/1996 | Yatvin et al. |
| 5,543,390 A | 8/1996 | Yatvin et al. |
| 5,543,391 A | 8/1996 | Yatvin et al. |
| 5,554,728 A | 9/1996 | Basava et al. |
| 5,610,054 A | 3/1997 | Draper |
| 5,633,358 A | 5/1997 | Gruetzke et al. |
| 5,633,388 A | 5/1997 | Diana et al. |
| 5,676,942 A | 10/1997 | Testa et al. |
| 5,703,058 A | 12/1997 | Schinazi et al. |
| 5,711,944 A | 1/1998 | Gilbert et al. |
| 5,725,859 A | 3/1998 | Omer |
| 5,738,845 A | 4/1998 | Imakawa |

(Continued)

FOREIGN PATENT DOCUMENTS

| AU | 2010-249481 | 12/2011 |
| CA | 2 682 230 A1 | 10/2008 |

(Continued)

OTHER PUBLICATIONS

Cahard, Dominique, et al., Aryloxy Phosphoramidate Triesters as Pro-Tides, Mini-Reviews in Medicinal Chemistry (2004), 4, 371-381.
McGuigan, Christopher, Certain Phosphoramidate Derivatives of Dideoxy Uridine (ddU) Are Active Against HIV and Successfully By-pass Thymidine Kinase, FEBS Letters 351 (1994) 11-14.
International Preliminary Report issued Nov. 22, 2011 for International Application No. PCT/US2010/035641.

(Continued)

*Primary Examiner* — Shaojia Anna Jiang
*Assistant Examiner* — Dale R Miller

(57) ABSTRACT

Disclosed herein are nucleoside phosphoramidates and their use as agents for treating viral diseases. These compounds are inhibitors of RNA-dependent 5 RNA viral replication and are useful as inhibitors of HCV NS5B polymerase, as inhibitors of HCV replication and for treatment of hepatitis C infection in mammals.

5 Claims, 21 Drawing Sheets

(56) References Cited

U.S. PATENT DOCUMENTS

| | | |
|---|---|---|
| 5,738,846 A | 4/1998 | Greenwald et al. |
| 5,747,646 A | 5/1998 | Hakimi et al. |
| 5,767,097 A | 6/1998 | Tam |
| 5,792,834 A | 8/1998 | Hakimi et al. |
| 5,830,455 A | 11/1998 | Valtuena et al. |
| 5,830,905 A | 11/1998 | Diana et al. |
| 5,834,594 A | 11/1998 | Hakimi et al. |
| 5,837,257 A | 11/1998 | Tsai et al. |
| 5,846,964 A | 12/1998 | Ozeki |
| 5,849,696 A | 12/1998 | Chretien et al. |
| 5,869,253 A | 2/1999 | Draper |
| 5,891,874 A | 4/1999 | Colacino et al. |
| 5,905,070 A | 5/1999 | Schinazi et al. |
| 5,908,621 A | 6/1999 | Glue et al. |
| 5,922,757 A | 7/1999 | Chojkier |
| 5,928,636 A | 7/1999 | Alber et al. |
| 5,942,223 A | 8/1999 | Bazer et al. |
| 5,980,884 A | 11/1999 | Blatt et al. |
| 5,990,276 A | 11/1999 | Zhang et al. |
| 6,004,933 A | 12/1999 | Spruce et al. |
| 6,034,134 A | 3/2000 | Gold et al. |
| 6,043,077 A | 3/2000 | Barber et al. |
| 6,056,961 A | 5/2000 | Lavie et al. |
| 6,060,080 A | 5/2000 | Kikuchi et al. |
| 6,090,932 A | 7/2000 | McGee et al. |
| 6,130,326 A | 10/2000 | Ramasamy et al. |
| 6,132,763 A | 10/2000 | Fisher |
| 6,156,501 A | 12/2000 | McGall et al. |
| 6,180,134 B1 | 1/2001 | Zalipsky et al. |
| 6,232,300 B1 | 5/2001 | Schinazi et al. |
| 6,239,159 B1 | 5/2001 | Brown et al. |
| 6,348,587 B1 | 2/2002 | Schinazi et al. |
| 6,372,883 B1 | 4/2002 | Attwood et al. |
| 6,391,859 B1 | 5/2002 | Schinazi et al. |
| 6,410,531 B1 | 6/2002 | Llinas-Brunet et al. |
| 6,420,380 B2 | 7/2002 | Llinas-Brunet et al. |
| 6,455,513 B1 | 9/2002 | McGuigan et al. |
| 6,455,690 B1 | 9/2002 | Tam et al. |
| 6,475,985 B1 | 11/2002 | Wagner et al. |
| 6,479,463 B1 | 11/2002 | Wang et al. |
| 6,495,677 B1 | 12/2002 | Ramasamy et al. |
| 6,509,320 B1 | 1/2003 | Wang et al. |
| 6,534,523 B1 | 3/2003 | Llinas-Brunet et al. |
| 6,552,183 B1 | 4/2003 | Ramasamy et al. |
| 6,555,677 B2 | 4/2003 | Petrillo et al. |
| 6,573,248 B2 | 6/2003 | Ramasamy et al. |
| 6,642,206 B2 | 11/2003 | Ramasamy et al. |
| 6,660,721 B2 | 12/2003 | Devos et al. |
| 6,677,314 B2 | 1/2004 | Klecker et al. |
| 6,677,315 B2 | 1/2004 | Klecker et al. |
| 6,680,303 B2 | 1/2004 | Schinazi et al. |
| 6,682,715 B2 | 1/2004 | Klecker et al. |
| 6,683,045 B2 | 1/2004 | Klecker et al. |
| 6,703,374 B1 | 3/2004 | Klecker et al. |
| 6,753,309 B2 | 6/2004 | Klecker et al. |
| 6,777,395 B2 | 8/2004 | Bhat et al. |
| 6,784,166 B2 | 8/2004 | Devos et al. |
| 6,787,305 B1 | 9/2004 | Li et al. |
| 6,787,526 B1 | 9/2004 | Bryant et al. |
| 6,812,219 B2 | 11/2004 | LaColla et al. |
| 6,815,542 B2 | 11/2004 | Hong et al. |
| 6,846,810 B2 | 1/2005 | Martin et al. |
| 6,897,201 B2 | 5/2005 | Boyer et al. |
| 6,908,924 B2 | 6/2005 | Watanabe et al. |
| 6,911,424 B2 | 6/2005 | Schinazi et al. |
| 6,914,054 B2 | 7/2005 | Sommadossi et al. |
| 6,962,991 B2 | 11/2005 | Dempcy et al. |
| 7,018,985 B1 | 3/2006 | Boyer et al. |
| 7,018,989 B2 | 3/2006 | McGuigan et al. |
| 7,081,449 B2 | 7/2006 | Pietrzkowski et al. |
| 7,105,493 B2 | 9/2006 | Sommadossi et al. |
| 7,105,499 B2 | 9/2006 | Carroll et al. |
| 7,125,855 B2 | 10/2006 | Bhat et al. |
| 7,148,206 B2 | 12/2006 | Sommadossi et al. |
| 7,163,929 B2 | 1/2007 | Sommadossi et al. |
| 7,202,224 B2 | 4/2007 | Eldrup et al. |
| 7,217,523 B2 | 5/2007 | Wagner |
| 7,268,119 B2 | 9/2007 | Cook et al. |
| 7,307,065 B2 | 12/2007 | Schinazi et al. |
| 7,323,453 B2 | 1/2008 | Olsen et al. |
| 7,365,057 B2 | 4/2008 | LaColla et al. |
| 7,390,791 B2 | 6/2008 | Becker et al. |
| 7,429,572 B2 | 9/2008 | Clark |
| 7,601,820 B2 | 10/2009 | Wang et al. |
| 7,608,597 B2 | 10/2009 | Sommadossi et al. |
| 7,608,600 B2 | 10/2009 | Storer et al. |
| 7,635,689 B2 | 12/2009 | LaColla et al. |
| 7,754,699 B2 | 7/2010 | Chun et al. |
| 7,879,815 B2 | 2/2011 | MacCoss et al. |
| 7,964,580 B2 | 6/2011 | Sofia et al. |
| 8,148,349 B2 | 4/2012 | Meppen et al. |
| 8,173,621 B2 | 5/2012 | Du et al. |
| 8,334,270 B2 | 12/2012 | Sofia et al. |
| 8,415,322 B2 | 4/2013 | Clark |
| 8,551,973 B2 | 10/2013 | Bao et al. |
| 8,563,530 B2 | 10/2013 | Chang et al. |
| 8,580,765 B2 | 11/2013 | Sofia et al. |
| 8,642,756 B2 | 2/2014 | Ross et al. |
| 8,859,756 B2 | 10/2014 | Ross et al. |
| 8,916,538 B2 | 12/2014 | Kuldipkumar et al. |
| 9,085,573 B2 | 7/2015 | Du et al. |
| 2001/0034440 A1 | 10/2001 | Shepard et al. |
| 2002/0058635 A1 | 5/2002 | Averett |
| 2002/0198173 A1 | 12/2002 | Schinazi et al. |
| 2003/0050229 A1 | 3/2003 | Sommadossi et al. |
| 2003/0060400 A1 | 3/2003 | LaColla et al. |
| 2003/0120071 A1 | 6/2003 | McGuigan et al. |
| 2003/0144502 A1 | 7/2003 | Pietrzkowski et al. |
| 2003/0153744 A1 | 8/2003 | Mekouar et al. |
| 2003/0187018 A1 | 10/2003 | Llinas-Brunet et al. |
| 2004/0006007 A1 | 1/2004 | Gosselin et al. |
| 2004/0014108 A1 | 1/2004 | Eldrup et al. |
| 2004/0023240 A1 | 2/2004 | Marliere et al. |
| 2004/0023901 A1 | 2/2004 | Cook et al. |
| 2004/0059104 A1 | 3/2004 | Cook et al. |
| 2004/0063622 A1 | 4/2004 | Sommadossi et al. |
| 2004/0067901 A1 | 4/2004 | Bhat et al. |
| 2004/0072788 A1 | 4/2004 | Bhat et al. |
| 2004/0087541 A1 | 5/2004 | Jonaitis et al. |
| 2004/0097461 A1 | 5/2004 | Sommadossi et al. |
| 2004/0097462 A1 | 5/2004 | Sommadossi et al. |
| 2004/0101535 A1 | 5/2004 | Sommadossi et al. |
| 2004/0102414 A1 | 5/2004 | Sommadossi et al. |
| 2004/0110717 A1 | 6/2004 | Carroll et al. |
| 2004/0167140 A1 | 8/2004 | Schinazi et al. |
| 2004/0191824 A1 | 9/2004 | Dempcy et al. |
| 2004/0214844 A1 | 10/2004 | Otto et al. |
| 2004/0229839 A1 | 11/2004 | Babu et al. |
| 2004/0229840 A1 | 11/2004 | Bhat et al. |
| 2004/0248892 A1 | 12/2004 | Wang |
| 2004/0254141 A1 | 12/2004 | Schinazi et al. |
| 2004/0259934 A1 | 12/2004 | Olsen et al. |
| 2004/0265969 A1 | 12/2004 | Li et al. |
| 2004/0266996 A1 | 12/2004 | Rabi |
| 2005/0009737 A1 | 1/2005 | Clark |
| 2005/0020825 A1 | 1/2005 | Storer et al. |
| 2005/0026853 A1 | 2/2005 | Mekouar et al. |
| 2005/0031588 A1 | 2/2005 | Sommadossi et al. |
| 2005/0075309 A1 | 4/2005 | Storer et al. |
| 2005/0080034 A1 | 4/2005 | Standring et al. |
| 2005/0090660 A1 | 4/2005 | Watanabe et al. |
| 2005/0124532 A1 | 6/2005 | Sommadossi et al. |
| 2005/0130931 A1 | 6/2005 | Boyer et al. |
| 2005/0137161 A1 | 6/2005 | Sommadossi et al. |
| 2005/0148534 A1 | 7/2005 | Castellino et al. |
| 2005/0154056 A1 | 7/2005 | Yang et al. |
| 2005/0164960 A1 | 7/2005 | Olsen et al. |
| 2005/0215513 A1 | 9/2005 | Boojamra et al. |
| 2005/0227947 A1 | 10/2005 | Chen et al. |
| 2005/0261237 A1 | 11/2005 | Boojamra et al. |
| 2005/0267018 A1 | 12/2005 | Blatt et al. |
| 2006/0003951 A1 | 1/2006 | Mekouar et al. |
| 2006/0014943 A1 | 1/2006 | Dempcy et al. |
| 2006/0035866 A1 | 2/2006 | Cannizzaro et al. |

(56) References Cited

U.S. PATENT DOCUMENTS

| | | |
|---|---|---|
| 2006/0040890 A1 | 2/2006 | Martin et al. |
| 2006/0040927 A1 | 2/2006 | Blake et al. |
| 2006/0040944 A1 | 2/2006 | Gosselin et al. |
| 2006/0079478 A1 | 4/2006 | Boojamra et al. |
| 2006/0110727 A9 | 5/2006 | McGall et al. |
| 2006/0122146 A1 | 6/2006 | Chun et al. |
| 2006/0122154 A1 | 6/2006 | Olsen et al. |
| 2006/0142238 A1 | 6/2006 | McGuigan |
| 2006/0166964 A1 | 7/2006 | Hudyma et al. |
| 2006/0194749 A1 | 8/2006 | Keicher et al. |
| 2006/0199783 A1 | 9/2006 | Wang et al. |
| 2006/0241064 A1 | 10/2006 | Roberts et al. |
| 2006/0276511 A1 | 12/2006 | Serrano-Wu et al. |
| 2006/0293306 A1 | 12/2006 | Beaulieu et al. |
| 2007/0015905 A1 | 1/2007 | LaColla et al. |
| 2007/0037735 A1 | 2/2007 | Gosselin et al. |
| 2007/0037773 A1 | 2/2007 | Sommadossi et al. |
| 2007/0042939 A1 | 2/2007 | LaColla et al. |
| 2007/0042988 A1 | 2/2007 | Klumpp et al. |
| 2007/0042990 A1 | 2/2007 | Gosselin et al. |
| 2007/0049754 A1 | 3/2007 | Boojamra et al. |
| 2007/0060498 A1 | 3/2007 | Gosselin et al. |
| 2007/0060541 A1 | 3/2007 | Gosselin et al. |
| 2007/0087960 A1 | 4/2007 | Storer et al. |
| 2007/0197463 A1 | 8/2007 | Chun et al. |
| 2007/0225249 A1 | 9/2007 | Shi |
| 2007/0265222 A1 | 11/2007 | MacCoss et al. |
| 2007/0275912 A1 | 11/2007 | Bhat et al. |
| 2007/0275947 A1 | 11/2007 | Bergstrom |
| 2008/0070861 A1 | 3/2008 | Clark |
| 2008/0253995 A1 | 10/2008 | Clark |
| 2009/0004135 A1 | 1/2009 | Clark |
| 2009/0036666 A1 | 2/2009 | Clark |
| 2009/0137521 A1 | 5/2009 | Hamilton et al. |
| 2009/0176732 A1 | 7/2009 | Beigelman et al. |
| 2009/0233879 A1 | 9/2009 | Reddy et al. |
| 2009/0280084 A1 | 11/2009 | Schinazi et al. |
| 2009/0306007 A1 | 12/2009 | Wagner |
| 2010/0016251 A1 | 1/2010 | Sofia et al. |
| 2010/0022468 A1 | 1/2010 | Meppen et al. |
| 2010/0029008 A1 | 2/2010 | Rojas Stutz et al. |
| 2010/0035835 A1 | 2/2010 | Narjes et al. |
| 2010/0048917 A1 | 2/2010 | Wang et al. |
| 2010/0081628 A1 | 4/2010 | Du et al. |
| 2010/0137576 A1 | 6/2010 | Stec et al. |
| 2010/0152128 A1 | 6/2010 | Attenni et al. |
| 2010/0173863 A1 | 7/2010 | Schinazi et al. |
| 2010/0227801 A1 | 9/2010 | Hopkins |
| 2010/0279973 A1 | 11/2010 | Chun et al. |
| 2010/0286083 A1 | 11/2010 | Bao et al. |
| 2010/0298257 A1 | 11/2010 | Ross et al. |
| 2010/0316594 A1 | 12/2010 | Sommadossi et al. |
| 2011/0015146 A1 | 1/2011 | Sofia et al. |
| 2011/0124592 A1 | 5/2011 | McGuigan et al. |
| 2011/0245484 A1 | 10/2011 | Ross et al. |
| 2011/0251152 A1 | 10/2011 | Ross et al. |
| 2011/0257122 A1 | 10/2011 | Sofia et al. |
| 2012/0107278 A1 | 5/2012 | Berrey et al. |
| 2012/0245335 A1 | 9/2012 | Clark |
| 2013/0029929 A1 | 1/2013 | Sofia et al. |
| 2013/0109647 A1 | 5/2013 | Berrey et al. |
| 2013/0136776 A1 | 5/2013 | Cleary et al. |
| 2013/0137654 A1 | 5/2013 | Ross et al. |
| 2013/0165401 A1 | 6/2013 | Ross et al. |
| 2013/0165644 A1 | 6/2013 | Ross et al. |
| 2013/0288997 A1 | 10/2013 | Ross et al. |
| 2013/0310551 A1 | 11/2013 | Ross et al. |

FOREIGN PATENT DOCUMENTS

| | | |
|---|---|---|
| CN | 101108870 A | 1/2008 |
| DE | 199 14 474 A1 | 10/1999 |
| EP | 0 180 276 A1 | 5/1986 |
| EP | 0 350 287 A2 | 1/1990 |
| EP | 1 828 217 A2 | 9/2007 |
| EP | 1 881 001 A1 | 1/2008 |
| EP | 2 097 430 A1 | 9/2009 |
| EP | 2 124 555 A2 | 12/2009 |
| EP | 2 207 786 B1 | 3/2012 |
| EP | 2552931 | 7/2014 |
| JP | 5-238939 A | 9/1993 |
| WO | 89/02733 A1 | 4/1989 |
| WO | 90/00555 A1 | 1/1990 |
| WO | 91/16920 A1 | 11/1991 |
| WO | 91/18914 A1 | 12/1991 |
| WO | 91/19721 A1 | 12/1991 |
| WO | 93/00910 A1 | 1/1993 |
| WO | 94/26273 A1 | 11/1994 |
| WO | 95/13090 A1 | 5/1995 |
| WO | 95/24185 A1 | 9/1995 |
| WO | 96/15132 A1 | 5/1996 |
| WO | 96/32403 A2 | 10/1996 |
| WO | 97/12033 A1 | 4/1997 |
| WO | 97/36554 A1 | 10/1997 |
| WO | 98/16184 A2 | 4/1998 |
| WO | 98/17679 A1 | 4/1998 |
| WO | 98/22496 A2 | 5/1998 |
| WO | 99/07734 A2 | 2/1999 |
| WO | 99/15194 A1 | 4/1999 |
| WO | 99/32139 A1 | 7/1999 |
| WO | 99/32140 A1 | 7/1999 |
| WO | 99/43691 A1 | 9/1999 |
| WO | 99/59621 A1 | 11/1999 |
| WO | 99/64016 A1 | 12/1999 |
| WO | 00/06529 A1 | 2/2000 |
| WO | 00/09531 A2 | 2/2000 |
| WO | WO-00/18775 A1 | 4/2000 |
| WO | 00/37110 A2 | 6/2000 |
| WO | 01/09121 A2 | 2/2001 |
| WO | 01/32153 A2 | 5/2001 |
| WO | 01/60315 A2 | 8/2001 |
| WO | 01/79246 A2 | 10/2001 |
| WO | 01/81359 A1 | 11/2001 |
| WO | 01/90121 A2 | 11/2001 |
| WO | 01/91737 A2 | 12/2001 |
| WO | 01/92282 A2 | 12/2001 |
| WO | 01/96353 A2 | 12/2001 |
| WO | 02/08187 A1 | 1/2002 |
| WO | 02/08198 A2 | 1/2002 |
| WO | 02/08241 A2 | 1/2002 |
| WO | 02/08251 A2 | 1/2002 |
| WO | 02/08256 A2 | 1/2002 |
| WO | 02/18404 A2 | 3/2002 |
| WO | 02/32414 A2 | 4/2002 |
| WO | 02/32920 A2 | 4/2002 |
| WO | 02/48116 A2 | 6/2002 |
| WO | 02/48157 A2 | 6/2002 |
| WO | 02/48165 A2 | 6/2002 |
| WO | 02/48172 A2 | 6/2002 |
| WO | 02/057287 A2 | 7/2002 |
| WO | 02/057425 A2 | 7/2002 |
| WO | 02/060926 A2 | 8/2002 |
| WO | 02/100415 A2 | 12/2002 |
| WO | 03/000713 A1 | 1/2003 |
| WO | 03/006490 A1 | 1/2003 |
| WO | 03/010141 A2 | 2/2003 |
| WO | 03/024461 A1 | 3/2003 |
| WO | 03/026589 A2 | 4/2003 |
| WO | 03/037895 A1 | 5/2003 |
| WO | 03/051899 A1 | 6/2003 |
| WO | 03/053989 A1 | 7/2003 |
| WO | 03/061576 A2 | 7/2003 |
| WO | 03/062256 A1 | 7/2003 |
| WO | 03/064456 A1 | 8/2003 |
| WO | 03/068244 A1 | 8/2003 |
| WO | 03/101993 A1 | 12/2003 |
| WO | 03/104250 A1 | 12/2003 |
| WO | 03/105770 A2 | 12/2003 |
| WO | 03/106477 A1 | 12/2003 |
| WO | 2004/000858 A2 | 12/2003 |
| WO | 2004/002422 A2 | 1/2004 |
| WO | 2004/002940 A1 | 1/2004 |
| WO | 2004/002944 A1 | 1/2004 |
| WO | 2004/002977 A1 | 1/2004 |

(56) References Cited

FOREIGN PATENT DOCUMENTS

| | | |
|---|---|---|
| WO | 2004/002999 A2 | 1/2004 |
| WO | 2004/003000 A2 | 1/2004 |
| WO | 2004/003138 A2 | 1/2004 |
| WO | 2004/007512 A2 | 1/2004 |
| WO | 2004/009020 A2 | 1/2004 |
| WO | 2004/009610 A2 | 1/2004 |
| WO | 2004/011478 A2 | 2/2004 |
| WO | 2004/014313 A2 | 2/2004 |
| WO | 2004/014852 A2 | 2/2004 |
| WO | 2004/035571 A1 | 4/2004 |
| WO | 2004/041201 A2 | 5/2004 |
| WO | 2004/046331 A2 | 6/2004 |
| WO | 2004/065367 A1 | 8/2004 |
| WO | 2004/080466 A1 | 9/2004 |
| WO | 2004/094452 A2 | 11/2004 |
| WO | 2004/096210 A1 | 11/2004 |
| WO | 2004/096234 A2 | 11/2004 |
| WO | 2004/096235 A2 | 11/2004 |
| WO | 2004/096286 A2 | 11/2004 |
| WO | 2004/106356 A1 | 12/2004 |
| WO | 2005/002626 A2 | 1/2005 |
| WO | 2005/003147 A2 | 1/2005 |
| WO | 2005/007810 A2 | 1/2005 |
| WO | 2005/009418 A2 | 2/2005 |
| WO | 2005/012327 A2 | 2/2005 |
| WO | 2005/020884 A2 | 3/2005 |
| WO | 2005/021568 A2 | 3/2005 |
| WO | 2005/028502 A1 | 3/2005 |
| WO | 2005/037214 A2 | 4/2005 |
| WO | 2005/067900 A2 | 7/2005 |
| WO | 2005/072361 A2 | 8/2005 |
| WO | 2005/082144 A1 | 9/2005 |
| WO | 2005/087788 A2 | 9/2005 |
| WO | 2005/095403 A2 | 10/2005 |
| WO | 2005/103045 A1 | 11/2005 |
| WO | 2005/123087 A1 | 12/2005 |
| WO | 2006/000922 A2 | 1/2006 |
| WO | 2006/012078 A2 | 2/2006 |
| WO | 2006/012440 A2 | 2/2006 |
| WO | 2006/020082 A1 | 2/2006 |
| WO | 2006/029081 A1 | 3/2006 |
| WO | 2006/031725 A2 | 3/2006 |
| WO | 2006/035061 A1 | 4/2006 |
| WO | 2006/037028 A2 | 4/2006 |
| WO | 2006/050161 A2 | 5/2006 |
| WO | 2006/063149 A1 | 6/2006 |
| WO | 2006/063717 A2 | 6/2006 |
| WO | 2006/065335 A2 | 6/2006 |
| WO | 2006/065590 A2 | 6/2006 |
| WO | 2006/067606 A1 | 6/2006 |
| WO | 2006/093801 A1 | 9/2006 |
| WO | 2006/100310 A1 | 9/2006 |
| WO | 2006/116557 A1 | 11/2006 |
| WO | 2006/120251 A1 | 11/2006 |
| WO | 2006/120252 A2 | 11/2006 |
| WO | 2006/121820 A1 | 11/2006 |
| WO | 2007/002602 A2 | 1/2007 |
| WO | 2007/014920 A1 | 2/2007 |
| WO | 2007/014921 A1 | 2/2007 |
| WO | 2007/014922 A1 | 2/2007 |
| WO | 2007/014925 A1 | 2/2007 |
| WO | 2007/014926 A1 | 2/2007 |
| WO | 2007/015824 A2 | 2/2007 |
| WO | 2007/020193 A2 | 2/2007 |
| WO | 2007/027248 A2 | 3/2007 |
| WO | 2007/039142 A1 | 4/2007 |
| WO | 2007/039145 A1 | 4/2007 |
| WO | 2007/065829 A1 | 6/2007 |
| WO | 2007/070556 A2 | 6/2007 |
| WO | 2007/076034 A2 | 7/2007 |
| WO | 2007/088148 A1 | 8/2007 |
| WO | 2007/092000 A1 | 8/2007 |
| WO | 2007/093901 A1 | 8/2007 |
| WO | 2007/095269 A2 | 8/2007 |
| WO | 2008/010921 A2 | 1/2008 |
| WO | 2008/045419 A1 | 4/2008 |
| WO | 2008/048128 A1 | 4/2008 |
| WO | 2008/062206 A2 | 5/2008 |
| WO | 2008/079206 A1 | 7/2008 |
| WO | 2008/082601 A2 | 7/2008 |
| WO | 2008/085508 A2 | 7/2008 |
| WO | 2008121634 A1 | 9/2008 |
| WO | 2008/142055 A2 | 11/2008 |
| WO | 2009/029844 A1 | 3/2009 |
| WO | 2009/052287 A1 | 4/2009 |
| WO | 2009/115893 A2 | 9/2009 |
| WO | 2009/120878 A2 | 10/2009 |
| WO | 2009/129120 A2 | 10/2009 |
| WO | 2009/132123 A1 | 10/2009 |
| WO | 2009/152095 A2 | 12/2009 |
| WO | 2010/042834 A1 | 4/2010 |
| WO | 2010/075517 A2 | 7/2010 |
| WO | 2010/075549 A2 | 7/2010 |
| WO | 2010/075554 A1 | 7/2010 |
| WO | 2010/080878 A1 | 7/2010 |
| WO | 2010/081082 A2 | 7/2010 |
| WO | WO-2010/135569 | 11/2010 |
| WO | 2011/035231 A1 | 3/2011 |
| WO | WO-2011/123645 | 10/2011 |
| WO | WO-2011/123668 | 10/2011 |
| WO | WO-2011/123672 | 10/2011 |

OTHER PUBLICATIONS

Selected prosecution documents from U.S. Appl. No. 12/053,015: (1) Jun. 15, 2010 Restriction Requirement; (2) Oct. 28, 2010 Amendment; (3) Jan. 5, 2011 Notice of Allowance; and (4) Apr. 1, 2011 Amendment.
U.S. Appl. No. 13/099,671, filed May 3, 2011—pending claims as of Jun. 17, 2011.
U.S. Appl. No. 13/076,552, filed Mar. 31, 2011—original claims.
U.S. Appl. No. 12/645,710, filed Dec. 23, 2009—original claims.
Selected prosecution documents from U.S. Appl. No, 10/182,8753: (1) Feb. 26, 2007 Amendment; (2) Mar. 30, 2007 Office Action; (3) Jun. 19, 2007 Interview Summary; (4) Sep. 12, 2007 Amendment; (5) Sep. 12, 2007 Declaration; (6) Sep. 24, 2007 Declaration; (7) Nov. 28, 2007 Amendment; (8) Feb. 26, 2008 Office action; (9) Mar. 11, 2008 Amendment; and (10) May 29, 2008 Notice of Allowance.
U.S. Appl. No. 11/854,218—pending claims as of Jun. 28, 2011.
Selected prosecution documents from U.S. Appl. No. 11/854,218: (1) Sep. 12, 2007 Amendment; (2) Oct. 1, 2009 Office Action; (3) Mar. 31, 2010 Response; (4) Mar. 3, 2011 Declaration; (5) Jul. 22, 2010 Office Action; (6) Oct. 11, 2010 Amendment; (7) Oct. 11, 2010 Declaration; (8) Dec. 23, 2010 Office Action; (9) Jun. 28, 2011 Amendment.
U.S. Appl. No. 12/878,262—pending claims as of Sep. 1, 2011.
Selected prosecution documents from U.S. Appl. No. 12/878,262: (1) Sep. 9, 2010 Amendment; (2) Jun. 8, 2011 Office Action; and (3) Sep. 1, 2011 Amendment.
International Search Report and Writen Opinion mailed Nov. 7, 2011 for International Application PCT/US2011/030725.
Chawla et al., CRIPS (2004) 5(1): 9-12.
Haleblian, J. Pharm. Sci. (1975) 64(8): 1269-1288.
J.K. Guillory Polymorphism in Pharmaceutical Solids (1999); p. 183-226; H.G. Brittain (ed.); Marcel Dekker, Inc. (New York).
Byrn et al., Pharmaceutical Research (1995) 12(7) 945-954.
McGuigan et al., Biorg. Med. Chem. (2005) 13: 3219-3227.
Sofia et al., J. Med. Chem. (2010) 53(19):7202-7218.
Partial International Search Report of PCT/US2011/030725 mailed Aug. 22, 2011.
International Search Report of PCT/US2010/035641 mailed Sep. 28, 2010.
Office Action issued Feb. 25, 2011—PA patent appln. No. 88758-01.
Gudmundsson et al., Nucleosides, Nucleotides & Nucleic Acids (2003) 22(10):1953-1961.
McGuigan et al., Bioorg. & Med. Chem. Lett. (2009) 19:4316-4320.
Siddiqui et al., J. Med. Chem. (1999) 42(3): 393-399.
Venkatachalam et al., Bioorg. & Med. Chem. (2006) 14:5161-5177.
Dumez et al., Arzneim.-Forsch./Drug Res. (2006), 56(2a):136-151.
Gardelli et al., J. Med. Chem. (2009) 52(17): 5394-5407.

(56) References Cited

OTHER PUBLICATIONS

Gudmundsson et al., Nucleosides, Nucleotides and Nucleic Acids (2004) 23(12): 1929-1937.
Lehsten et al., Org. Process Res. & Dev. (2002) 6(6): 819-822.
McGuigan et al., Bioorg. & Med. Chem. Lett. (2009) 19: 4250-4254.
Nakayama et al., J. Am. Chem. Soc. (1990) 112(19): 6936-6942.
Wozniak et al., Chem. Soc. Rev. (2003) 32:158-169.
Uchiyama et al., J. Org. Chem. (1993) 58(2): 373-379.
Mitchell et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J. Chem. Soc. Perkin. Trans. 1, pp. 2345-2353 (1992).
Olsen et al., "2'-Modified Nucleoside Analogs as Inhibitors of Hepatitis C RNA Replication," Program and Abstracts, 16th International Conference on Antiviral Research, Abstract No. 121, p. A76 (Apr. 27-May 1, 2003).
Otto, M., "Evaluation of Nucleoside Analogs in the Hepatitis C Virus Replicon System," Framing the Knowledge of Therapeutics for Viral Hepatitis, IHL Press, First Edition, pp. 247-261 (2006).
Piantadosi et al., "Synthesis and Evaluation of Novel Ether Lipid Nucleoside Conjugates for Anti-HIV-1 Activity," J. Med. Chem., vol. 34, No. 4, pp. 1408-1414 (1991).
Pierra et al., "Synthesis and Pharmacokinetics of Valopicitabine (NM283), an Efficient Prodrug of the Potent Anti-HCV Agent 2'-C-Methylcytidine," J. Med. Chem., vol. 49, No. 22, pp. 6614-6620 (2006).
Starrett, Jr. et al., "Synthesis, Oral Bioavailability Determination, and in Vitro Evaluation of Prodrugs of the Antiviral Agent 9-[2-(Phosphonomethoxy)ethyl]adenine (PMEA)," J. Med. Chem., vol. 37, No. 12, pp. 1857-1864 (1994).
Stuyver et al., "Inhibition of hepatitis C replicon RNA synthesis by B-D-2'-deoxy-2'-fluoro-2'-C-methlcytidine: a specific inhibitor of hepatitis C virus replication," Antiviral Chemistry & Chemotherapy, vol. 17, No. 2, pp. 79-87 (2006).
Stuyver et al., "Dynamics of Subgenomic Hepatitis C Virus Replicon RNA Levels in Huh-7 Cells after Exposure to Nucleoside Antimetabolites," J. Virol., vol. 77, No. 19, pp. 10689-10694 (2003).
Stuyver et al., "Ribonucleoside Analogue that Blocks Replication of Bovine Viral Diarrhea and Hepatitis C Viruses in Culture," Antimicrobial Agents and Chemotherapy, vol. 47, No. 1, pp. 244-254 (2003).
Wolff, M.E., "Burger's Medicinal Chemistry and Drug Discovery," Fifth Edition, vol. 1, pp. 975-977 (1995).
Zon, G., "4 Cyclophosphoamide Analogues," Progress in Medicinal Chemistry, vol. 19, pp. 205-246 (1982).
Bhat et al., "Synthesis and Pharmacokinetic Properties of Nucleoside Analogues as Possible Inhibitors of HCV RNA Replication," (Oral Session V: Hepatitis C Virus, Flaviviruses), 16th International Conference on Antiviral Research, Abstract No. 120, p. A75 (Apr. 27-May 1, 2003).
Chu et al., "Isolation and Structure of SCH 351633: A Novel Hepatitis C Virus (HCV) NS3 Protease Inhibitor from the Fungus Penicillium Griseofulvum," Bioorg. & Med. Chem. Lett., vol. 9, pp. 1949-1952 (1999).
Chu et al., "Structure of Sch 68631: A New Hepatitis C Virue Proteinase Inhibitor from *Streptomyces* sp." Tet. Lett., vol. 37, No. 40, pp. 7229-7232 (1996).
De Lombaert et al., "N-Phosphonomethyl Dipeptides and Their Phosphonate Prodrugs, a New Generation of Neutral Endopeptidase (NEP, EC 3.4.24.11) Inhibitors," J. Med. Chem., vol. 37, No. 4, pp. 498-511 (1994).
Edmundson et al., "Cyclic Organophosphorus Compounds. Part 23. Configurational Assignments in the 4-Phenyl-1,3,2-dioxaphosphorinane Series. X-Ray Molecular Structure of cis-2-Benzylamino-4-phenyl-1,3,2-dioxaphosphorinane 2-oxide," J. Chem. Research (S), pp. 122-123 (1989).

Goekjian et al., "Synthesis of Fluorinated Marcocyclic Bis(indolyl)maleimides as Potential 19F NMR Probes for Protein Kinase C," J. Org. Chem. vol., 64., No. 12, pp. 4238-4246 (1999).
Hernandez et al., "Synthesis of Highly Functionalized Chiral Nitriles by Radical Fragmentation of beta-Hydroxy Azides. Convenient Transformation of Aldononitriles into 1,4- and 1,5-Iminoalditols," J. Org. Chem., vol. 69. No. 24, pp. 8437-8444 (2004).
Hostetler et al., "Greatly Enhanced Inhibition of Human Immunodeficiency Virus Type 1 Replication in CEM and HT4-6C Cells by 3'-Deoxythymidine Diphosphate Dimyristoylglycerol, a Lipid Prodrug of 3'-Deoxythymidine," Antimicrobial Agents and Chemotherapy, vol. 36, No. 9, pp. 2025-2029 (1992).
Kucera et al., "Novel Membrane-Interactive Ether Lipid Analogs That Inhibit Infectious HIV-1 Production and Induce Defective Virus Formation," Aids Research and Human Retroviruses, vol. 6, No. 4, pp. 491-501 (1990).
Meier et al., "Cyclic Saligenyl Phosphotriesters of 2',3'-Dideoxy-2',3'-didehydrothymidine (d4T)—A New Pro-Nucleotide Approach," Bioorg. & Med. Chem. Lett., vol. 7, No. 2, pp. 99-104, (1997).
Neidlein et al., "Mild Preparation of 1-Benzyloxyiminoalkylphosphonic Dichlorides: Application to the Synthesis of Cyclic Phosphonic Diesters and Cyclic Monoester Amides," Heterocycles, vol. 35, No. 2, pp. 1185-1203 (1993).
Nifantyev et al., "Synthesis and Structure of Some Stable Phospholane-Phospholanes," Phosphorus, Sulfur, and Silicon, vol. 113, pp. 1-13 (1996).
Novak, J. J. K., "Chiroptical Properties of 2-Methyl-1,4-Lactones; Revised Absolute Configuration of 2-Deoxy-2-C-Methyl-erythro-D-Pentono-1,4-Lactones," Collection Czechoslov. Chem. Commun., vol. 39, pp. 869-882 (1974).
Novak, J. J. K., "Nucleic Acid Components and Their Analogues CXLIII. Nucleosides Derived from 2-Deoxy-2(R)-C-Methyl-erythro-D-Pentose," Collection Czechoslov. Chem. Commun., vol. 36, pp. 3670-3677 (1971).
Oishi et al., "Asymmetric Dihydroxylation of Chiral Olefins. High Control of Diastereofacial Selection," Tet. Lett., vol. 34, No. 22, pp. 3573-3576 (1993).
Shih et al., "Preparation and Structures of 2-Dimethylamino-4-phenyl-1,3,2-dioxaphosphorinane-2-oxides," Bull. Inst. Chem., Acad. Sin., vol. 41, pp. 9-16, (Mar. 1994).
Stella, V. J., "Prodrugs as Therapeutics," Expert opinion on therapeutic patents, vol. 14, No. 3, pp. 277-280 (Mar. 2004).
Xiao-Ling et al., "Study on the Chirality of Sulfur in Ethyl (2S, 3R,4R)-4,5-O-Isopropylidene-2,3-sulfinyl-2,3,4,5-tetrahydroxy-pentanoate", Acta Chimica Sinica, vol. 55, pp. 600-604 (1997).
Xiao-Ling et al., "The Synthesis of (2S,3R)-Sphingosine from D-Mannitol", Acta Chimica Sinica, vol. 54, pp. 826-832 (1996).
International Search Report issued in International Application No. PCT/US2004/012472 mailed Dec. 30, 2004 (4 pages).
International Search Report issued in International Application No. PCT/US2005/025916 mailed Jun. 15, 2006 (2 pages).
International Search Report issued in International Application No. PCT/EP2006/069060 mailed Jan. 30, 2007 (4 pages).
International Search Report issued in International Application No. PCT/US2005/032406 mailed May 8, 2008 (3 pages).
Bartenschlager et al., "Nonstructural Protein 3 of the Hepatitis C Virus Encodes a Serine-Type Proteinase Required for Cleavage at the NS3/4 and NS4/5 Junctions," J. Virol., vol. 67, No. 7, pp. 3835-3844 (1993).
Bartenschlager et al., "Kinetic and Structural Analyses of Hepatitis C Virus Polyprotein Processing," J. Virol., vol. 68, No. 8, pp. 5045-5055 (1994).
Bazan et al., "Detection of a Trypsin-like Serine Protease Domain in Flaviviruses and Pestiviruses," Virology, vol. 171, pp. 637-639 (1989).
Beaulieu et al., "Inhibitors of the HCV NS5B polymerase: New hope for the treatment of hepatitis C infections," Current Opinion in Investigational Drugs, vol. 5, No. 8, pp. 838-850 (2004).
Behrens et al., "Identification and properties of the RNA-dependent RNA polymerase of hepatitis C virus," The EMBO Journal, vol. 15, No. 1, pp. 12-22 (1996).

(56) References Cited

OTHER PUBLICATIONS

Calisher et al., "Antigenic Relationships between Flaviviruses as Determined by Cross-neutralization Tests with Polyclonal Antisera," J. Gen. Virol., vol. 70, pp. 37-43 (1989).
Carroll et al., "Nucleoside Analog Inhibitors of Hepatitis C Virus Replication," Infectious Disorders—Drug Targets, vol. 6, No. 1, pp. 17-29 (2006).
Eckart et al., "The Hepatitis C Virus Encodes a Serine Protease Involved in Processing of the Putative Nonstructural Proteins from the Viral Polyprotein Precursor," Biochemical and Biophysical Research Communications, vol. 192, No. 2, pp. 399-406 (1993).
Failla et al., "Both NS3 and NS4A are Required for Proteolytic Processing of Hepatitis C Virus Nonstructural Proteins," J. Virol., vol. 68, No. 6, pp. 3753-3760 (1994).
Rice, C. M., "Flaviviridae: The Viruses and Their Replication," Fields Virology, 3rd Edition, vol. 1, pp. 931-959 (1996).
Gorbalenya et al., "A conserved NTP-motif in putative helicases," Nature, vol. 333, p. 22 (1988).
Gorbalenya et al., "N-terminal domains of putative helicases of flavi- and pestiviruses may be serine proteases," Nucleic Acids Research, vol. 17, No. 10, pp. 3889-3897 (1989).
Grakoui et al., "Characterization of the Hepatitis C Virus-Encoded Serine Proteinase: Determination of Proteinase-Dependent Polyprotein Clevage Sites," J. Virol., vol. 67, No. 5, pp. 2832-2843 (1993).
Grakoui et al., "A second hepatitis C virus-encoded proteinase," Proc. Natl. Acad. Sci., vol. 90, pp. 10583-10587 (1993).
Griffith et al., "HCV Anti-viral Agents," Annual Reports in Medicinal Chemistry, vol. 39, pp. 223-237 (2004).
Halstead, S. B., "Selective Primary Health Care: Strategies for Control of Disease in the Developing World. XI. Dengue," Review of Infectious Diseases, vol. 6, No. 2, pp. 251-263 (1984).
Office Action in U.S. Appl. No. 13/732,725 dated Feb. 3, 2015 (14 pages).
Brittain, H. G. (2009). Polymorphism in pharmaceutical solids (vol. 192). Informa Healthcare.
Cahard, et al., Aryloxy Phosphoramidate Triestes as Pro-Tides, Mini-Reviews in Medicinal Chemistry, (2004), 4:371-381.
Communication enclosing Partial European Search Report for European Patent Application No. 13159791.6 dated Feb. 6, 2014 (6 pages).
Office Action in Canadian Application No. 2794669 dated Jan. 15, 2015 (4 pages).
Office Action in Chinese Application No. 201180017181.3 dated Aug. 19, 2014 (7 pages).
Search and Examination Report in African Regional Intellectual Property Organization Application No. AP/P/2012/006543 dated Jan. 9, 2015 (4 pages).
Communication pursuant to Rule 114(2) for European Application No. 11714465.9 dated Dec. 1, 2014 (3 pages).
Office Action in Chinese Application No. 20118017181.3 dated Dec. 8, 2014 (9 pages).
Examination Report for New Zealand Application No. 603232 dated Dec. 4, 2014 (3 pages).
English Translation of Office Action for Taiwanese Application No. 100111246 dated Sep. 15, 2014 (3 pages).
English Translation of Office Action for Chilean Application No. 716-2011 dated Oct. 9, 2014 (8 pages).
English Translation of Office Action for Eurasian Application No. 201290993 dated Sep. 17, 2014 (3 pages).
English Translation of Office Action for Mexican Application No. MX/a/2012/011171 dated Aug. 7, 2014 (3 pages).
English Translation of Office Action for Panamanian Application No. 89230-02 dated Jun. 17, 2014 (4 pages).
Office Action for Pakistani Application No. 748/2012 dated Sep. 4, 2014 (2 pages).
Office Action for Pakistani Application No. 233/2011 dated Mar. 28, 2014 (2 pages).
Office Action in Ukraine Application No. A 2012 12444 dated Jan. 27, 2015 (4 pages).

Examination Report in Australia Application No. 2011235112 dated Feb. 5, 2015 (3 pages).
Office Action in Chilean Application No. 716-2011 dated Mar. 30, 2015( 6 pages).
Office Action in Mexican Application No. MX/a/2012/011171 dated Mar. 25, 2015 (6 pages).
Office action in U.S. Appl. No. 13/925,078 dated Apr. 23, 2015 (7 pages).
Subsequent Substantive Examination Report in Philippine Application No. 1/2011/502433 dated Apr. 15, 2015 (1 page).
Notification of Publication of Search Report in Euarasian Application No. 201370186 dated Feb. 27, 2015 (2 pages).
Resolution No. 50410 in Colombian Application No. 12-195602 dated Aug. 18, 2015, (11 pages).
Official Letter in Taiwan Application No. 104102544 dated Aug. 21, 2015, (11 pages).
Notice of Preliminary Rejection in Korean Application No. 10-2014-7032628 dated Aug. 27, 2015 (8 pages).
Office Action, Paper No. 3 in Philippines Application No. 1-2014-502684 dated Sep. 4, 2015 (2 pages).
English translation of First Office Action in Taiwan Application No. 99115937 dated May 11, 2015, 7 pages.
English translation of Official Action in Eurasian Application No. 201290993 dated Apr. 27, 2015, 3 pages.
Extended Search Report in European Application No. 15152203.4 dated May 28, 2015, 9 pages.
English translation of Official Notification in Israel Application No. 222099 dated Apr. 28, 2015, 10 pages.
Further Examination Report in New Zealand Application No. 623602 dated Jul. 21, 2015, 2 pages.
First Examination Report in New Zealand Application No. 709926 dated Jul. 21, 2015, 2 pages.
Communication pursuant to Rule 94(3) in European Application No. 13159791.6 dated Jul. 28, 2015, 9 pages.
English translation of Official Action in Mexican Application No. MX/a/2012/011171 dated Aug. 3, 2015, 3 pages.
English translation of Office Action in Israel Application No. 237471 dated Aug. 5, 2015, 6 pages.
Abraham et al., "Synthesis and Biological Activity of Aromatic Amino Acid Phosphoramidates of 5-fluoro-2'-deoxyuridine and 1-beta-Arabinofuranosylcytosine: Evidence of Phosphoramidase Activity," J. Med. Chem., vol. 39, No. 23, pp. 4569-4575, (1996).
Pogam et al., "No Evidence of R7128 Drug Resistance After Up to 4 Weeks Treatment of GT1, 2 and 3 Hepatitis C Virus Infected Individuals", 44th Annual Meeting of European Association for the Study of the Liver (EASL), Copenhagen, Denmark (Apr. 22-26, 2009).
Sofia et al., "beta-D-2'-Deoxy-2'-C-methyluridine Phosphoramidates: Potent and Selective Inhibitors of HCV RNA Replication", Poster #P-259, 14th International Symposium on Hepatitis C Virus and Related Viruses, Glasgow, Scotland, UK (Sep. 9 to 13, 2007).
Sofia, M.J., "beta-D-2'-Deoxy-2'-fluoro-2'-C-methyluridine Phosphoramidates: Potent and Selective Inhibitors of HCV RNA Replication", 2nd International Workshop on HCV—Resistance and New Compounds (Oct. 31, 2007).
Sofia et al., "beta-D-2'-Deoxy-2'-fluoro-2'-C-methyluridine Phosphoramidates: Potent and Selective Inhibitors of HCV RNA Replication", 2nd International Workshop on HCV, Poster #7 (Oct. 31, 2007).
Sofia, M.J., "R7128, A Potent and Selective Nucleoside Inhibitor of HCV NS5B Polymerase: An Overview of Clinical Efficacy and Progress Toward Second Generation Inhibitors", HCV Drug Discovery 2008, Chicago, IL (Apr. 28, 2008).
Response filed Oct. 25, 2010 at the EPO for European patent application No. EP08732818.3.
Abraham et al., "Synthesis, Biological Activity and Decomposition Studies of Amino Acid Phosphomonoester Amidates of Acyclovir," Nucleosides, Nucleotides and Nucleic Acids, vol. 16, No. 10, pp. 2079-2092 (1997).
Balzarini et al., "Mechanism of anti-HIV action of masked alaninyl d4t-MP derivatives," Proc. Natl. Acad. Sci., vol. 93, pp. 7295-7299 (1996).

(56) References Cited

OTHER PUBLICATIONS

Chang et al., "Amino Acid Phosphoramidate Monoesters of 3'-Azido-3'-deoxythymidine: Relationship between Antiviral Potency and Intracellular Metabolism," J. Med. Chem., vol. 44, No. 2, pp. 223-231 (2001).

Chen et al., "In Vivo Pharmacokinetics and Metabolism of Anti-Human Immunodeficiency Virus Agent D4t-5'-[P-Bromophenyl Methoxyalaninyl Phosphate] (Sampidine) in Mice," Drug Metabolism and Disposition, vol. 29, No. 7, pp. 1035-1041 (2001).

Chen et al., "Metabolism of Stavudine-5'-[P-Bromophenyl Methoxyalaninyl Phosphate], Stampidine, in Mice, Dogs, and Cats," Drug Metabolism and Disposition, vol. 30, No. 12, pp. 1523-1531 (2002).

Chou et al., "Evidence that Human Histidine Triad Nucleotide Binding Protein 3 (Hint3) is a Distinct Branch of the Histidine Triad (HIT) Superfamily," J. Mol. Biol., vol. 373, pp. 978-989 (2007).

Chou et al., "Phosphoramidate Pronucleotides: A Comparison of the Phosphoramidase Substrate Specificity of Human and *Escherichia coli* Histidine Triad Nucleotide Binding Proteins," Molecular Pharmaceutics, vol. 4, No. 2, pp. 208-217 (2006).

Cihlar et al. "Design and Profiling of GS-9148, a Novel Nucleotide Analog Active against Nucleoside-Resistant Variants of Human Immunodeficiency Virus Type 1, and Its Orally Bioavailable Phosphonoamidate Prodrug, GS-9131," Antimicrobial Agents and Chemotherapy, vol. 52, No. 2, pp. 655-665 (2008).

Congiatu et al. "Molecular Modeling Studies on the Binding of Some Protides to the Putative Human Phosphoramidase Hint1," Nucleosides, Nucleotides and Nucleic Acids, vol. 26, pp. 1121-1124 (2007).

Congiatu et al., "Naphthyl Phosphoramidate Derivatives of BVdU as Potential Anticancer Agents: Design, Synthesis and Biological Evaluation," Nucleosides, Nucleotides, and Nucleic Acids, vol. 24, No. 5-7, pp. 485-489 (2005).

Curley et al., "Synthesis and anti-HIV evaluation of some phosphoramidate derivatives of AZT: studies on the effect of chain elongation on biological activity," Antiviral Research, vol. 14, pp. 345-356 (1990).

D'Cruz et al., "Stampidine: a selective oculo-genital microbicide," Journal of Antimicrobial Chemotherapy, vol. 56, pp. 10-19 (2005).

Drontle et al., "Designing a Pronucleotide Stratagem: Lessons from Amino Acid Phosphoramidates of Anticancer and Antiviral Pyrimidines," MiniReviews in Medicinal Chemistry, vol. 4, No. 4, pp. 409-419 (2004).

Egron et al., "S-Acyl-2-thioethyl Phosphoramidate Diester Derivatives as Mononucleotide Prodrugs" J. Med. Chem., vol. 46, No. 21, pp. 4564-4571 (2003).

Howes et al., "The Regiospecific One-Pot Phosphorylation of Either the 5'- or 2'-Hydroxyl in 3'-Deoxycytidines Without Protection: Critical Role of the Base," Nucleosides, Nucleotides, and Nucleic Acids, vol. 22, No. 5-8, pp. 687-689 (2003).

Iyer et al., "Synthesis, in Vitro Anti-Breast Cancer Activity, and Intracellular Decomposition of Amino Acid Methyl Ester and Alkyl Amide Phosphoramidate Monoesters of 3'-Azido-3'-deoxythymidine (AZT)," J. Med. Chem., vol. 43, No. 11, pp. 2266-2274 (2000).

Kim et al., "Monitoring the Intracellular Metabolism of Nucleoside Phosphoramidate Pronucleotides by 31P NMR," Nucleosides, Nucleotides and Nucleic Acid, vol. 23, No. 1 & 2, pp. 483-493 (2004).

Lehsten et al., "An Improved Procedure for the Synthesis of Nucleoside Phosphoramidates," Organic Process Research and Development, vol. 6, pp. 819-822 (2002).

McGuigan et al., "Aryl phosphate derivatives of AZT retain activity against HIV1 in cell lines which are resistant to the action of AZT," Antiviral Research, vol. 17, pp. 311-321 (1992).

McGuigan et al., "Application of Phosphoramidate ProTide Technology Significantly Improves Antiviral Potency of Carbocyclic Adenosine Derivatives," J. Med. Chem., vol. 49, No. 24, pp. 7215-7226 (2006).

McGuigan et al., "Application of Phosphoramidate Pronucleotides Technology to Abacavir Leads to a Significant Enhancement of Antiviral Potency," J. Med. Chem., vol. 48, No. 10, pp. 3504-3515 (2005).

McGuigan et al., "Aryl Phosphoramidate Derivatives of d4T Have Improved Anti-HIV Efficacy in Tissue Culture and May Act by the Generation of a Novel Intracellular Metabolite," J. Med. Chem., vol. 39, No. 8, pp. 1748-1753 (1996).

McGuigan et al., "Synthesis and anti-HIV activity of some novel chain-extended phosphoramidate derivatives of d4T (stavudine): esterase hydrolysis as a rapid predictive test for antiviral potency," Antiviral Chemistry and Chemotherapy, vol. 9, pp. 109-115 (1998).

McGuigan et al., "Synthesis and evaluation of some novel phosphoramidate derivatives of 3'-azido-3'-deoxythymidine (AZT) as anti-HIV compounds," Antiviral Chemistry and Chemotherapy, vol. 1, No. 2, pp. 107-113 (1990).

McIntee et al., "Probing the Mechanism of Action and Decomposition of Amino Acid Phosphomonoester Amidates of Antiviral Nucleoside Prodrugs," J. Med. Chem., vol. 40, No. 21, pp. 3323-3331 (1997).

Perrone et al., "First Example of Phosphoramidate Approach Applied to a 4'-Substituted Purine Nucleoside (4'Azidoadenosine): Conversion of an Inactive Nucleoside to a Submicromolar Compound versus Hepatitis C Virus," J. Med. Chem., vol. 50, No. 22, pp. 5463-5470 (2007).

Perrone et al. "Application of the Phosphoramidate ProTide Approach to 4'-Azidouridine Confers Sub-micromolar Potency versus Hepatitis C Virus on an Inactive Nucleoside," J. Med. Chem., vol. 50, No. 8, 1840-1849 (2007).

Saboulard et al., "Characterization of the Activation Pathway of Phosphoramidate Triester Prodrugs of Stavudine and Zidovudine," Mol. Pharmacol., vol. 56, pp. 693-704 (1999).

Schultz, C., "Prodrugs of Biologically Active Phosphate Esters" Bioorg. and Med. Chem., vol. 11, pp. 885-898 (2003).

Siccardi et al., "Stereoselective and Concentration-Dependent Polarized Epithelial Permeability of a Series of Phosphoramidate Triester Prodrugs of d4T: An in Vitro Study in Caco-2 and Madin-Darby Canine Kidney Cell Monolayers," J. Pharmacol. and Exp. Ther., vol. 307, No. 3, pp. 1112-1119 (2003).

Siccardi et al., "Stereospecific chemical and enzymatic stability of phosphoramidate triester prodrugs of d4T in vitro," European Journal of Pharmaceutical Sciences, vol. 22, pp. 25-31 (2004).

Siddiqui et al., "Design and Synthesis of Lipophilic Phosphoramidate d4T-MP Prodrugs Expressing High Potency Against HIV in Cell Culture: Structural Determinants for in Vitro Activity and QSAR," J. Med. Chem., vol. 42, No. 20, pp. 4122-4128 (1999).

Siddiqui et al., "Enhancing the Aqueous Solubility of d4T-based Phosphoramidate Prodrugs," Bioorg. and Med. Chem. Lett., vol. 10, pp. 381-384 (2000).

Song et al., "Pharmacokinetics of Amino Acid Phosphoramidate Monoesters of Zidovudine in Rats," Antimicrobial Agents and Chemotherapy, vol. 46, No. 5, pp. 1357-1363 (2002).

Uckun et al., "In Vivo Pharmacokinetics and Toxicity Profile of the Anti-HIV Agent Stampidine in Dogs and Feline Immunodeficiency Virus-infected Cats," Arzneim.-Forsch./Drug Res., vol. 56, No. 2a, pp. 176-192 (2006).

Valette et al., "Decomposition Pathways and in Vitro HIV Inhibitory Effects of IsoddA Pronucleotides: Toward a Rational Approach for Intracellular Delivery of Nucleoside 5'-Monophosphates," J. Med. Chem., vol. 39, No. 10, pp. 1981-1990 (1996).

Venkatachalam et al., "Synthesis and metabolism of naphthyl substituted phosphoramidate derivatives of stavudine," Bioorg. and Med. Chem., vol. 14, pp. 5161-5177 (2006).

Venkatachalam et al., "Rational Drug Design of Multifunctional Phosphoramidate Substituted Nucleoside Analogs," Current Pharmaceutical Design, vol. 10, No. 15, pp. 1713-1726 (2004).

Wagner et al., "Antiviral Nucleoside Drug Delivery via Amino Acid Phosphoramidates," Nucleosides, Nucleotides and Nucleic Acids, vol. 18, No. 4 & 5, pp. 913-919 (1999).

Wu et al., "Synthesis and Biological Activity of a Gemcitabine Phosphoramidate Prodrug," J. Med. Chem., vol. 50, No. 15, pp. 3743-3746 (2007).

(56) References Cited

OTHER PUBLICATIONS

Gunic et al., "6-Hydrazinopurine 2'-methyl ribonucleosides and their 5'-monophosphate prodrugs as potent hepatitis C virus inhibitors," Bioorg. & Med. Chem. Lett., vol. 17, pp. 2456-2458 (2007).
International Search Report issued in International PCT application No. PCT/US2008/058183 mailed Mar. 31, 2010 (7 pages).
International Preliminary Examination Report along with Written Opinion of the International Searching Authority issued in International PCT application No. PCT/US2008/058183 issued Apr. 7, 2010 (17 pages).
Halstead, S. B., "Pathogenesis of Dengue: Challenges to Molecular Biology," Science, vol. 239, pp. 476-481 (1988).
Hijikata et al., "Two Distinct Proteinase Activities required for the Processing of a Putative Nonstructural Precursor Protein of Hepatitis C Virus," J. Virol., vol. 67, No. 8, pp. 4665-4675 (1993).
Jin et al., "Expression, Isolation, and characterization of the Hepatitis C Virus ATPase/RNA Helicase," Archives of Biochemistry and Biophysics, vol. 323, No. 1, pp. 47-53 (1995).
Kim et al., "C-Terminal Domain of the Hepatitis C Virus NS3 Protein Contains an RNA Helicase Activity," Biochemical and Biophysical Research Communications, vol. 215, No. 1, pp. 160-166 (1995).
Koonin et al., "Evolution and Taxonomy of Positive-Strand RNA Viruses: Implications of Comparatives Analysis of Amino Acid Sequences," Critical Reviews in Biochemistry and Molecular Biology, vol. 28, No. 5, pp. 375-430 (1993).
Lohmann et al., "Biochemical Properties of Hepatitis C Virus NS5B RNA-Dependent RNA Polymerase and Identification of Amino Acid Sequence Motifs Essential for Enzymatic Activity," J. Virol., vol. 71, No. 11, pp. 8416-8428 (1997).
Meyers et al., "Molecular Characterization of Pestiviruses," Advance in Virus Research, vol. 47, pp. 53-119 (1996).
Moennig et al., "The Pestiviruses," Advances in Virus Research, vol. 41, pp. 53-99 (1992).
Monath, T. P., M.D., "Japanese Encephalitis—A Plague of the Orient," N. Engl. J. Med., vol. 319, No. 10, pp. 641-643 (Sep. 8, 1988).
Ni et al., "Progress and development of small molecule HCV antivirals," Current Opinion in Drug Discovery & Development, vol. 7, No. 4, pp. 446-459 (2004).
Tan et al., "Hepatitis C Therapeutics: current Status and Emerging Strategies," Nature Reviews, vol. 1, pp. 867-881 (2002).
Tomei et al., "NS3 Is a Serine Protease Required for Processing of Hepatitis C Virus Polyprotein," J. Virol., vol. 67, No. 7, pp. 4017-4026 (1993).
Walker et al., "Promising candidates for the treatment of chronic hepatitis C," Expert Opin. Investig. Drugs, vol. 12, No. 8, pp. 1269-1280 (2003).
Warrener et al., "Pestivirus NS3 (p80) Protein Possesses RNA Helicase Activity," J. Virol., vol. 69, No. 3, pp. 1720-1726 (1995).
Wiskerchen et al., Pestivirus Gene Expression: Protein p80 of Bovine Viral Diarrhea Virus Is a Proteinase Involved in Polyprotein Processing, Virology, vol. 184, pp. 341-350 (1991).
Wu et al., "Targeting NS5B RNA-Dependent RNA Polymerase for Anti-HCV Chemotherapy," Current Drug Targets—Infectious Disorders, vol. 3, No. 3, pp. 207-219 (2003).
Xu et al., "Bovine Viral Diarrhea Virus NS3 Serine Proteinase: Polyprotein Cleavage Sites, Cofactor Requirements, and Molecular Model of an Enzyme Essential for Pestivirus Replication," J. Virol., vol. 71, No. 7, pp. 5312-5322 (1997).
Yuan et al., "Expression, Purification, and Partial Characterization of HCV RNA Polymerase," Biochemical and Biophysical Research Communications, vol. 232, No. 1, pp. 231-235 (1997).
Zhong et al., "Identification and characterization of an RNA-Dependent RNA Polymerase Activity within the Nonstructural Protein 5B Region of Bovine Viral Diarrhea Virus," J. Virol., vol. 72, No. 11, pp. 9365-9369 (1998).
Aquaro et al., "Activities of Masked 2',3'-Dideoxynucleoside Monophosphate Derivatives Against Human Immunodeficiency Virus in Resting Macrophages," Antimicrobial Agents and Chemotherapy, vol. 44, No. 1, pp. 173-177 (2000).
Chapman et al., "Purification of PMPA Amidate Prodrugs by SMB Chromatography and X-Ray Crystallography of the Diastereomerically Pure GS-7340," Nucleosides, Nucleotides & Nucleic Acids, vol. 20, No. 4-7, pp. 1085-1090 (2001).
Chapman et al., "Practical Synthesis, Separation, and Stereochemical Assignment of the PMPS Pro-Drug GS-7340," Nucleosides, Nucleotides & Nucleic Acids, vol. 20, No. 4 - 7, pp. 621-628 (2001).
Eisenberg et al., "Metabolism of GS-7340, A Novel Phenyl Monophosphoramidate Intracellular Prodrug of PMPA, in Blood," Nucleosides, Nucleotides & Nucleic Acids, vol. 20, No. 4-7, pp. 1091-1098 (2001).
Lee et al., "Selective Intracellular Activation of a Novel Prodrug of the Human Immunodeficiency Virus reverse Transcriptase Inhibitor Tenofovir Leads to Preferential Distribution and Accumulation in Lymphatic Tissue," Antimicrobial Agents and Chemotherapy, vol. 49, No. 5, pp. 1898-1906 (2005).
McGuigan et al., "Synthesis, anti-human immunodeficiency virus activity and esterase lability of some novel carboxylic ester-modified phosphoramidate derivatives of stavudine (d4T)," Antiviral Chemistry & Chemotherapy, vol. 9, pp. 473-479 (1998).
Murakami et al., "The Mechanism of Action of beta-D-2'-Deoxy-2'-Fluoro-2'-C-Methylcytidine Involves a Second Metabolic Pathway Leading to beta-D-2'-Deoxy-2'-Fluoro-2'-C-Methyluridine 5'-Triphosphate, a Potent Inhibitor of the Hepatitis C Virus RNA-Dependent RNA Polymerase," Antimicrobial Agents and Chemotherapy, vol. 52, No. 2, pp. 458-464 (2008).
Murakami et al., "Mechanism of Activation of beta-D-2'-Deoxy-2'-Fluoro-2'-C-Methylcytidine and Inhibition of hepatitis C Virus NS5B RNA Polymerase," Antimicrobial Agents and Chemotherapy, vol. 51, No. 2, pp. 503-509 (Feb. 2007).
Ray et al., "Intracellular Metabolism of the Nucleotide Prodrugs GS-9131, a Potent Anti-Human Immunodeficiency Virus Agent," Antimicrobial Agents and Chemotherapy, vol. 52, No. 2, pp. 648-654 (2008).
Stuyver et al., "Inhibition of the Subgenomic Hepatitis C Virus Replicon in Huh-7 Cells by 2'-Deoxy-2'-Fluorocytidine," Antimicrobial Agents and Chemotherapy, vol. 48, No. 2, pp. 651-654 (2004).
U.S. Appl. No. 10/828,753, Non-Final Office Action Rejection, mailed Mar. 30, 2007.
U.S. Appl. No. 10/828,753, Final Office Action Rejection, mailed Feb. 26, 2008.
U.S. Appl. No. 11/225,425, Non-Final Office Action Rejection, mailed Nov. 13, 2008.
U.S. Appl. No. 11/225,425, Non-Final Office Action Rejection, mailed Jul. 7, 2009.
Response to non-final Office Action dated Oct. 1, 2009 for U.S. Appl. No. 12/142,554.
U.S. Appl. No. 11/225,425, Final Office Action Rejection, mailed Feb. 18, 2010.
U.S. Appl. No. 11/353,597, Non-Final Office Action Rejection, mailed Oct. 2, 2007.
U.S. Appl. No. 11/353,597, Non-Final Office Action Rejection, mailed Jul. 17, 2008.
U.S. Appl. No. 11/353,597, Final Office Action Rejection, mailed Dec. 2, 2008.
U.S. Appl. No. 11/635,898, Non-Final Office Action Rejection, mailed Jul. 28, 2009.
U.S. Appl. No. 11/635,898, Pending claims filed on Dec. 24, 2009.
U.S. Appl. No. 11/854,218, Pending claims filed Sep. 12, 2007.
U.S. Appl. No. 11/854,218, Non-Final Office Action Rejection, mailed Oct. 1, 2009.
U.S. Appl. No. 12/142,536, Pending claims filed on Jun. 19, 2008.
U.S. Appl. No. 12/142,536, Non-Final Office Action Rejection, mailed Oct. 2, 2009.
U.S. Appl. No. 12/142,554, Non-Final Office Action Rejection, mailed Oct. 1, 2009.
U.S. Appl. No. 12/142,554, Pending claims filed on Dec. 17, 2009.
U.S. Appl. No. 12/240,342, Pending claims filed on Sep. 29, 2008.
U.S. Appl. No. 12/240,342, Non-Final Office Action Rejection, mailed Oct. 1, 2009.

(56) References Cited

OTHER PUBLICATIONS

U.S. Appl. No. 12/479,075, filed Jun. 5, 2009.
U.S. Appl. No. 12/553,483, Non-Final Office Action Rejection, mailed Dec. 17, 2009.
Search Report and Written Opinion for Singapore Application No. 2011086105 dated Apr. 30, 2014.
English Translation for Office Action in Korean Application No. 10-2014-7032628 dated Feb. 6, 2015.
Zhou, Xiao-Jian, et al., "Safety and Pharmacokinetics of IDX184, a Liver-Targeted Nucleotide Polymerase Inhibitor of Hepatitis C Virus, in Healthy Subjects," Antimicrob. Agents & Chemother. (2011) 55(1):76-81.
Zhu et al., "Design and synthesis of HCV agents with sequential triple inhibitory potentials," Bioorg. & Med. Chem. Lett. (2010) 20(17):5212-5216.
Supplementary Serarch Report in Singapore Application No. 201207206-2 dated Mar. 17, 2015, 7 pages.
Subsequent Substantive Examination Report for Philippines Application No. 1/2011/502433 dated Jan. 13, 2015, 1 page
English translation of Office Action in Japanese Application No. 2013-502843 dated Feb. 19, 2015, 3 pages.
Office Action in Canada Application No. 2819700 dated Mar. 6, 2015, 4 pages.
English translation of Office Action in Japanese Application No. 2012-512043 dated Mar. 17, 2015, 8 pages.
English translation of Office Action in Israel Application No. 237471 dated Mar. 10, 2015, 3 pages.
English Translation of Office Action in Korean Application No. 10-2011-7030501 dated Mar. 25, 2015, (4 pages).
Caira, " Crystalline Polymorphism of Organic Compounds," Topics in Current Chemistry, Springer, Berlin, DE, (1998), 198:163-208.
Extended Search Report in European Application No. 15152204.2 dated May 27, 2015, (12 pages).
Examiner's Report in Chilean Application No. 903-2013 dated Apr. 24, 2015 (8 pages).
Office Action in Eurasian Application No. 201171417/28 dated May 18, 2015 (2 pages).
Office Action in Korean Application No. 10-2011-7030501 dated Mar. 26, 2015 (9 pages).
Office Action in Canadian Application No. 2849694 dated Apr. 29, 2015 (4 pages).
Official Action in Ukraine Application No. a 2012 12444 dated Jun. 11, 2015 (8 pages).
Office Action in Chinese Application No. 201180017181.3 dated May 25, 2015 (7 pages).
Notification before Examination of Israel Application No. 239115 dated Jun. 15, 2015 (5 pages).
Notice of Rejection in Japanese Application No. 2014-197788 dated Jun. 16, 2015 (7 pages).
Murakami, E., et al., "The Mechanism of Action of beta-D-2'-Deoxy-2'-fluoro-2'-C-methylcytidine Involves a Second Metabolic Pathway Leading to beta-D-2'-Deoxy-2'-fluoro-2'-C-methyluridine 5'-Triphosphate, a Potent Inhibitor of the HCV RNA-Dependent RNA Polymerase," 14th International Symposium on Hepatitis C Virus and Related Viruses, Glasgow, Scotland (Sep. 2007).
Office Action issued in Canadian Patent Application No. 2,763,151, dated Sep. 25, 2013 (4 pages).
Office Action issued in Canadian Patent Application No. 2,794,669, dated Sep. 30, 2013 (4 pages).
Furman, Phillip A., et al., "PSI-7851: A Novel Liver-Targeting Nucleotide Prodrug for the Treatment of Hepatitis C," Hepatology (2008) 48(4 Suppl):1161A (Abstract #1901).
Furman, Phillip A., et al., "PSI-7851: A Novel Liver-Targeting Nucleotide Prodrug for the Treatment of Hepatitis C," Presented at the 59th Annual Meeting of the American Association for the Study of Liver Diseases, San Francisco, CA, Oct. 31-Nov. 4, 2008.
Furman, P.A., et al., "b-D-2'-Deoxy-2'-fluoro-2'-C-methyluridine Phosphoramidates are Potent and Selective Inhibitors of HCV RNA Replication," Presented at the 15th International Symposium on Hepatitis C Virus & Related Viruses, San Antonio, TX, Oct. 5-9, 2008.
Sofia, Michael J., et al., "Beta-D-2'-Deoxy-2'-fluoro-2'-C-methyluridine (PSI-6206) phosphoramidates: Potent liver targeting nucleoside inhibitors of HCV RNA replication," 236th ACS National Meeting, Philadelphia, PA, Aug. 20, 2008 (Abstract MEDI 330).
Mehellou, Youcef, et al., "Aryloxy Phosphoramidate Triesters: a Technology for Delivering Monophosphorylated Nucleosides and Sugars into Cells," ChemMedChem 4:1779-1791 (2009).
International Preliminary Report on Patentability for PCT/US2011/030725 mailed Oct. 2, 2012 (17 pages).
Wittine, K., et al., "The Novel Phosphoramidate Derivatives of NSAID 3-Hydroxypropylamides: Synthesis, Cytostatic and Antiviral Activity Evaluations," Eur. J. Med. Chem. (2009) 44:143-151.
International Search Report for PCT/US2009/046619 mailed Sep. 23, 2010 (4 pages).
U.S. Appl. No. 12/553,483, Pending claims filed on Feb. 22, 2010.
U.S. Appl. No. 12/645,710, filed Dec. 23, 2009.
U.S. Appl. No. 12/645,765, filed Dec. 23, 2009.
U.S. Appl. No. 12/645,821, filed Dec. 23, 2009.
Stephen G. Gillespie, et al., "Stereoselective Inhibition of Cholesterol Esterase by Enantiomeric Phosphonates," Phosphorous, Sulfur and Silicon, 1997, 122: 205-208.
Remington Farmacia, 17th ed., pp. 1912-1920 (1985) (Editorial Medica Panamericana, Buenos Aires).
English Translation of Office Action issued in Colombian Patent Application No. 11-158583, dated Dec. 3, 2013 (17 pages).
Office Action in Chinese Application No. 201080032541.2 dated Dec. 3, 2014.
English Translation of Office Action in Chilean Application No. 903-13 dated Dec. 3, 2014.
Substantive Examination Report for PH Application 1-2011-502433, dated May 20, 2014, 2 pages.
Subsequent Substantive Examination Report for PH Application 1-2011-502433, dated Aug. 1, 2014, 2 pages.
Baschang et al., "Neue Derivate von Thymidin-3',5'-cyclophosphat," Angew. Chem., vol. 85, No. 1, pp. 44-45 (1973).
Broeders et al., "A 400- and 600-Mhz 'H NMR Confromational Study on Nucleoside Cyclic 3', 5' PV-TBP Systems. Conformational Transmission Induces Diequatorial Orientation of the 3', 5'-Dioxaphosphorinane Ring in a Nonchair Confirmation," J. Am. Chem. Soc., vol. 112, No. 21, pp. 7475-7482 (1990).
Engels et al., "Ctclophosphate, III. Synthese und Eignschaften von Uridin-3',5'-cyclophosphat-estern," Chemische Berichte, vol. 110, No. 6, pp. 2019-2027 (1977).
Lopez Aparicio et al., "Synthesis of Saccharinic Acid Derivatives," Carbohydrate Research, vol. 129, pp. 99-109 (1984).
Nelson et al., "The Question of Chair-twist Equilibria for the Phosphate Rings of Nucleoside Cyclic 3',5'Monophosphates. 1H NMR and X-ray Crystallographic Study of Diastereomers of Thymidine Phenyl Cyclic 3',5'-Monophosphate," J. Am. Chem. Soc., vol. 109, No. 13, pp. 4058-4064 (1987).
Written Opinion of the International Searching Authority issued in International Application No. PCT/US2004/012472 (7 pages).
International Preliminary Report on Patentability and Written Opinion of the International Searching Authority issued in International Application No. PCT/US2004/012472 (8 pages).
International Preliminary Report on Patentability and Written Opinion of the International Searching Authority issued in International Application No. PCT/US2005/025916 (4 pages).
The Extended search report includes the supplementary European search report issued in European Application No. 05775359.2 dated Sep. 15, 2010 (9 pages).
International Preliminary Report on Patentability and Written Opinion of the International Searching Authority issued in International Application No. PCT/US2005/032406 (4 pages).
International Preliminary Report on Patentability and Written Opinion of the International Searching Authority issued in International Application No. PCT/EP2006/069060 (13 pages).
Written Opinion of the International Searching Authority issued in the International Application No. PCT/US/2008/058183 (12 pages).

(56) References Cited

OTHER PUBLICATIONS

International Search Report issued in International Application No. PCT/US2009/046619 (4 pages).
Partial International Search Report issued in International Application No. PCT/US2009/069475 (7 pages).
International Search Report and Written Opinion of the International Searching Authority issued in International Application No. PCT/US2009/069475 (21 pages).
Invitation to Pay Additional Fees & Partial International Search Report issued in International Application No. PCT/US2010/035641 (10 pages).
International Search Report and Written Opinion of the International Searching Authority issued in PCT/US2010/035641 (23 pages).
Gromova et al., "Optical Rotatory Dispersion and Circular Dichroism of Mono- and Oligonucleotide-Amino Acids (Amidates)," Biochim. Biophys. Acta., vol. 240, No. 1, pp. 1-11 (1971).
Harris et al., "Synthesis and antiviral evaluation of phosphoramidate derivatives of (E)-5-(2-bromovinyl)-2'-deoxyuridine," Antiviral Chemistry & Chemotherapy, vol. 12, No. 5, pp. 293-300 (2001).
Juodka et al., "Oligonucleotides and Nucleotide-Peptides. XXXIV. Synthesis and Some Properties of Complex Nucleotidyl (Oligonucleotidyl)-(P—N)-Amino Acids (Peptides) and Their Ethyl Esters," J. Carbohydrates Nucleosides Nucleotides, vol. 6, No. 4, pp. 333-357 (1979).
Juodka et al., "Oligonucleotides and Nucleotide-Peptides. XXXV. Some Properties of Nucleotidyl-(5'-N)-Amino Acid Esters Differing in Amino Acid and Nucleotide Components," J. Carbohydrates Nucleosides Nucleotides, vol. 8, No. 1, pp. 19-39 (1981).
Juodka et al., "Oligonucleotides and Nucleotide-Peptides. XXXVII. On the Mechanism of Hydrolysis of Uridyly-(5'-N)-Amino Acids. IntramolecuLar Catalysis by the alpha-Carboxyl Group of Amino Acids," J. Carbohydrates Nucleosides Nucleotides, vol. 8, No. 6, pp. 519-535 (1981).
Lackey et al., "Enzyme-catalyzed therapeutic agent (ECTA) design: activation of the antitumor ECTA compound NB1011 by thymidylate synthase," Biochemical Pharmacology, vol. 61, No. 2, pp. 179-189 (2001).
McIntee et al., "Amino Acid Phosphoramidate Nucleosides: Potential ADEPT/GDEPT Substrates," Bioorganic & Medicinal Chemistry Letters, vol. 11, No. 21, pp. 2803-2805 (2001).
Remy et al., "Studies on Flourinated Pyrimidines. XIV. The Synthesis of Derivatives of 5-Fluoro-2'-deoxyuridine 5'-Phosphate and Related Compounds," J. Org. Chem., vol. 27, No. 7, pp. 2491-2500 (1962).
Smirrnov et al., "A Fluorescent Study of Tryptophan Derivatives of Oligonucleotides and Their Helical Complexes with Polyuridylic," FEBS Letters, vol. 51. No. 1, pp. 211-214 (1975).
Yuodka et al., "Oligonucleotides and Polynucleotides. XXVI. Synthesis of Esters of Nucleotidyl- and Oligonucleotidyl-(5'-N)-(Amino Acid)S and -Peptides," Soviet Journal of Bioorganic Chemistry, vol. 2, No. 11 pp. 1089-1094(1976) Translated from Russian.
U.S. Appl. No. 60/392,350, filed Jun. 28, 2002.
U.S. Appl. No. 60/392,351, filed Jun. 28, 2002.
Asif et al., "Pharmacokinetics of the Antiviral Agent B-D-2'-Deoxy-2'-Fluoro-2'-C-Methylcytidine in Rhesus Monkeys," Antimicrobial Agents and Chemotherapy, vol. 51, No. 8, pp. 2877-2882 (2007).
Banker et al., "Prodrugs," Modern Pharmaceutics, Third Edition, Revised and Expanded, pp. 451 and 596 (1996).
Battaglia et al., "Combination Therapy with Interferon and Ribavirin in the Treatment of Chronic Hepatitis C Infection," The Annals of Pharmacotherapy, vol. 34, No. 4, pp. 487-494 (2000).
Berenguer, M., "Hepatitis C virus in the transplant setting," Antiviral Therapy, vol. 3, Supplement 3, pp. 125-136 (1998).
Clark et al., "Design, Synthesis, and Antiviral Activity of 2'-Deoxy-2'-fluoro-2'-C-methylcytidine, a Potent Inhibitor of Hepatitis C Virus Replication," J. Med. Chem., vol. 48, No. 17, pp. 5504-5508 (2005).
Davis, G. L., "Current Therapy for Chronic Hepatitis C," Gastroenterology, vol. 118, No. 2, pp. S104-S114 (2000).
Eldrup et al., "Oral Session V: Hepatitis C Virus, Flaviviruses," Program and Abstracts, The Sixteenth International Conference on Antiviral Research, p. A75, Abstract 119 (Apr. 27 to May 1, 2003).
Eldrup et al., "Structure-Activity Relationship of Purine Ribonucleosides for Inhibition of Hepatitis C Virus RNA-Dependent RNA Polymerase," J. Med. Chem., vol. 47, No. 9, pp. 2283-2295 (2004).
Farquhar et al., "Synthesis and Biological Evaluation of Neutral Derivatives of 5-Fluoro-2'-deoxyuridine 5'-Phosphate," J. Med. Chem., vol. 26, No. 8, pp. 1153-1158 (1983).
Farquhar et al., "Synthesis of Biological Evaluation of 9-[5'-(2-Oxo-1,3,2-oxazaphosphorinan-2-yl)-beta-D-arabinosyl] adenine and 9-[5'-(2-Oxo-1,3,2-dioxaphosphorinan-2-yl)-beta-D-arabinosyl]adenine: Potential Neutral Precursors of 9- [beta-D-Arabinofuranosyl]adenine 5'-Monophosphate," J. Med. Chem., vol. 28, No. 9, pp. 1358-1361 (1985).
Freed et al., "Evidence for acyloxymethyl esters of pyrimidine 5'-deoxyribonucleotides as extracellular sources of active 5'-deoxyribonucleotides in cultured cells," Biochemical Pharmacology, vol. 38, No. 19, pp. 3193-3198 (1989).
Hertel et al., "Synthesis of 2-Deoxy-2,2-difluoro-D-ribose and 2-Deoxy-2,2-difluoro-D-ribofuranosyl Nucleosides," J. Org. Chem., vol. 53, No. 11, pp. 2406-2409 (1988).
Hostetler et al., "Synthesis and Antiretroviral Activity of Phospholipid Analogs of Azidothymidine and Other Antiviral Nucleosides," J. Biol. Chem., vol. 265, No. 11, pp. 6112-6117 (1990).
Hunston et al., "Synthesis and Biological Properties of Some Cyclic Phosphotriesters Derived from 2'-Deoxy-5-fluorouridine," J. Med. Chem., vol. 27, No. 4, pp. 440-444 (1984).
International Search Report issued in International Application No. PCT/US2005/025916 mailed Jun. 15, 2006.
Jones et al., "Minireview: Nucleotide Prodrugs," Antiviral Research, vol. 27, No. 1-2 pp. 1-17 (1995).
Khamnei et al., "Neighboring Group Catalysis in the Design of Nucleotide Prodrugs," J. Med. Chem., vol. 39, No. 20, pp. 4109-4115 (1996).
Kotra et al., "Structure-Activity Relationships of 2'-Deoxy-2',2'-difluoro-L-erythro-pentofuranosyl Nucleosides," J. Med. Chem., vol. 40, No. 22, pp. 3635-3644 (1997).
Kryuchkov et al., "Influence of Solvent on the Strength of Cyclic Oxygen-Containing Phosphorus Acids," Bulletin of the Academy of Sciences of the USSR. Division of Chemical Science, vol. 36, No. 6, Part 1, pp. 1145-1148 (1987) Translated from Russian.
Li et al., "Synthesis of the Phosphoramidite Derivative of 2'-Deoxy-2'-C-beta-methylcytidine", J. Org. Chem., vol. 68, No. 17, pp. 6799-6802 (2003).
Ma et al., "Characterization of the Metabolic Activation of Hepatitis C Virus Nucleoside Inhibitor B-D-2'-Deoxy-2-Fluoro-2'-C-Methylcytidine (PSI-6130) and Identification of a Novel Active 5'-Triphosphate Species," J. Biol. Chem., vol. 282, No. 41, pp. 29812-29820 (Oct. 12, 2007).
U.S. Appl. No. 14/013,237, filed Aug. 29, 2013.
U.S. Appl. No. 14/057,675, filed Oct. 18, 2013.
U.S. Appl. No. 13/956,195, filed Jul. 31, 2013.
Office Action and Examination Search Report in Canadian Application No. 2,794,669 dated Oct. 22, 2015, 4 pages.
Office Action in Canadian Application No. 2,794,669 dated Jan. 24, 2014, 2 pages.
Office Action and Examination Search Report in Canadian Application No. 2,849,694 dated Feb. 11, 2016, 4 pages.
Resolution of Rejection in Chilean Application No. 2011-000716 dated Dec. 11, 2015, 3 pages.
Office Action and Search Report Chinese Application No. 201180017181.3 dated Jan. 24, 2014, 7 pages.
Office Action in Chinese Application No. 201180017181.3 dated Dec. 8, 2014, 4 pages.
Rejection Decision in Chinese Application No. 201180017181.3 dated Feb. 3, 2016, 9 pages.
Office Action in Chinese Application No. 201410247228.0 dated Aug. 5, 2015, 10 pages.
Second Office Action in Chinese Application No. 201410247228.0 dated Apr. 26, 2016, 7 pages.

(56) References Cited

OTHER PUBLICATIONS

English translation of Official Action in Eurasian Application No. 201290993 dated Apr. 12, 2016, 2 pages.
Communication pursuant to Article 94(3) in European Application No. 11714465.9 dated Apr. 8, 2014, 7 pages.
Communication pursuant to Article 94(3) in European Application No. 11714465.9 dated Aug. 13, 2013, 7 pages.
Communication pursuant to Article 94(3) in European Application No. 11714465.9 dated Dec. 12, 2014, 4 pages.
Extended European Search Report in European Application No. 13159791.6 dated Jul. 2, 2014, 15 pages.
Partial European Search Report in European Application No. 13159791.6 dated Feb. 6, 2014, 6 pages.
English translation of Notification prior to examination in Israel Application No. 222099 dated Oct. 2, 2014, 3 pages.
English translation of Official Action in Japanese Application No. 2013-502843 dated May 16, 2014, 5 pages.
English translation of Report of Reconsideration in Japanese Application No. 2013-502843 dated Aug. 13, 2015, 3 pages.
English translation of Notice of Reasons for Rejection in Korean Application No. 10-2012-7028451 dated Jun. 23, 2016, 8 pages.
English translation of Notice of Reasons for Rejection in Korean Application No. 10-2012-7028451 dated Dec. 18, 2015, 6 pages.
Further Examination Report in New Zealand Application No. 603232 dated Jan. 7, 2015, 3 pages.
English translation of Official Action and Search Report in Peru Application No. 1750-2012DIN dated Jan. 21, 2016, 15 pages.
Official Notification and Written Opinion in Singapore Application No. 2012072062 dated Mar. 13, 2015, 9 pages.
English translation of Official Action in Ukraine Application No. a 2012 12444 dated Oct. 22, 2015, 9 pages.
Non-Final Office Action in U.S. Appl. No. 13/936,448 dated Nov. 4, 2013, 6 pages.
English translation of Office Action in Vietnam Application No. 1-2012-03236 dated Dec. 28, 2012, 1 page.
Examination Report and Search Report in United Arab Emirates Application No. 1158/2011 dated Dec. 15, 2015, 11 pages.
Examination Report in Australia Application No. 2014274548 dated Oct. 6, 2015, 4 pages.
Office Action in Canadian Application No. 2,763,151 dated Jan. 10, 2014, 4 pages.
Office Action and Examination Search Report in Canadian Application No. 2,819,700 dated Oct. 8, 2014, 4 pages.
Office Action in Canadian Application No. 2,819,700 dated Jun. 4, 2014, 3 pages.

Resolution of Rejection in Chile Application No. 2010-000520 dated Dec. 16, 2015, 3 pages.
English translation of First Office Action and Patent Search Report in Chinese Application No. 201410487915X dated Nov. 3, 2015, 7 pages.
English translation of Fifth Official Action in Eurasian Application No. 201171417/28 dated Nov. 18, 2015, 2 pages.
English translation of Sixth Official Action in Eurasian Application No. 201171417/28 dated Mar. 3, 2016, 2 pages.
English translation of First Official Action in Eurasian Application No. 201370186/28 dated Mar. 24, 2016, 3 pages.
Communication pursuant to Article 94(3) in European Application No. 10721225.0 dated Aug. 20, 2014, 9 pages.
Extended European Search Report in European Patent Application No. 13159903.7 dated Dec. 19, 2013, 12 pages.
Partial European Search Report in European Patent Application No. 13159903.7 dated Sep. 2, 2013, 6 pages.
Communication pursuant to Article 94(3) in European Patent Application No. 15152203.4 dated Apr. 15, 2016, 8 pages.
English translation of Office Action in Israeli Application No. 237471 dated Dec. 24, 2015, 2 pages.
English translation of Office Action in Israeli Application No. 239115 dated Nov. 4, 2015, 2 pages.
English translation of Notice of Preliminary Rejection in Korean Application No. 10-2011-7030501 dated Aug. 20, 2014, 5 pages.
English translation of Notice of Preliminary Rejection in Korean Application No. 10-2015-7008852 dated Feb. 24, 2016, 5 pages.
English translation of Notice of Preliminary Rejection in Korean Application No. 10-2015-7008852 dated Aug. 13, 2015, 7 pages.
Substantive Examination Adverse Report and Search Report in Application No. PI 2011005625 dated Jan. 29, 2016, 3 pages.
First Examination Report in New Zealand Application No. 623602 dated Apr. 16, 2014, 2 pages.
Search and Examination Report in Singapore Application No. 2011086105 dated Nov. 3, 2014, 22 pages.
English translation of Office Action and Search Report in Taiwan Application No. 99115937 dated Jul. 21, 2014, 4 pages.
English translation of Official Letter and Search Report in Taiwan Application No. 99115937 dated Apr. 13, 2016, 6 pages.
English translation of Office Action in Taiwan Application No. 104102544 dated Mar. 31, 2016, 8 pages.
Final Rejection in U.S. Appl. No. 12/783,680 dated Dec. 10, 2012, 13 pages.
Non-Final Office Action in U.S. Appl. No. 12/783,680 dated Jun. 18, 2012, 9 pages.
Non-Final Office Action in U.S. Appl. No. 12/783,680 dated Apr. 16, 2013, 16 pages.
Non-Final Office Action in U.S. Appl. No. 13/738,425 dated Apr. 4, 2013, 8 pages.

NUCLEOSIDE PHOSPHORAMIDATES

PRIORITY CLAIM

This application is a continuation of U.S. application Ser. No. 13/732,725, filed Jan. 2, 2013, now U.S. Pat. No. 9,206,217, which is a divisional of U.S. application Ser. No. 12/783,680, filed May 20, 2010, now U.S. Pat. No. 8,642,756, which claims priority under 35 U.S.C. §119(e) to U.S. Provisional Patent Application No. 61/179,923, filed May 20, 2009, and 61/319,513, filed Mar. 31, 2010, all of which are incorporated by reference in their entireties.

FIELD OF THE INVENTION

Disclosed herein are nucleoside phosphoramidates and their use as agents for treating viral diseases. These compounds are inhibitors of RNA-dependent RNA viral replication and are useful as inhibitors of HCV NS5B polymerase, as inhibitors of HCV replication and for treatment of hepatitis C infection in mammals.

BACKGROUND

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest can harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring. Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. Therefore, NS5B polymerase is considered to be an essential component in the HCV replication complex (K. Ishi, et al, *Heptology*, 1999, 29: 1227-1235; V. Lohmann, et al., *Virology*, 1998, 249: 108-118). Inhibition of HCV NS5B polymerase prevents formation of the double-stranded HCV RNA and therefore constitutes an attractive approach to the development of HCV-specific antiviral therapies.

HCV belongs to a much larger family of viruses that share many common features.

Flaviviridae Viruses

The Flaviviridae family of viruses comprises at least three distinct genera: pestiviruses, which cause disease in cattle and pigs; flavivruses, which are the primary cause of diseases such as dengue fever and yellow fever; and hepaciviruses, whose sole member is HCV. The flavivirus genus includes more than 68 members separated into groups on the basis of serological relatedness (Calisher et al., *J. Gen. Virol*, 1993, 70, 37-43). Clinical symptoms vary and include fever, encephalitis and hemorrhagic fever (*Fields Virology*, Editors: Fields, B. N., Knipe, D. M., and Howley, P. M., Lippincott-Raven Publishers, Philadelphia, Pa., 1996, Chapter 31, 931-959). Flaviviruses of global concern that are associated with human disease include the Dengue Hemorrhagic Fever viruses (DHF), yellow fever virus, shock syndrome and Japanese encephalitis virus (Halstead, S. B., *Rev. Infect. Dis.*, 1984, 6, 251-264; Halstead, S. B., *Science*, 239:476-481, 1988; Monath, T. P., *New Eng. J. Med*, 1988, 319, 64 1-643).

The pestivirus genus includes bovine viral diarrhea virus (BVDV), classical swine fever virus (CSFV, also called hog cholera virus) and border disease virus (BDV) of sheep (Moennig, V. et al. *Adv. Vir. Res.* 1992, 41, 53-98). Pestivirus infections of domesticated livestock (cattle, pigs and sheep) cause significant economic losses worldwide. BVDV causes mucosal disease in cattle and is of significant economic importance to the livestock industry (Meyers, G. and Thiel, H. J., Advances in Virus Research, 1996, 47, 53-118; Moennig V., et al, Adv. Vir. Res. 1992, 41, 53-98). Human pestiviruses have not been as extensively characterized as the animal pestiviruses. However, serological surveys indicate considerable pestivirus exposure in humans.

Pestiviruses and hepaciviruses are closely related virus groups within the Flaviviridae family. Other closely related viruses in this family include the GB virus A, GB virus A-like agents, GB virus-B and GB virus-C (also called hepatitis G virus, HGV). The hepacivirus group (hepatitis C virus; HCV) consists of a number of closely related but genotypically distinguishable viruses that infect humans. There are at least 6 HCV genotypes and more than 50 subtypes. Due to the similarities between pestiviruses and hepaciviruses, combined with the poor ability of hepaciviruses to grow efficiently in cell culture, bovine viral diarrhea virus (BVDV) is often used as a surrogate to study the HCV virus.

The genetic organization of pestiviruses and hepaciviruses is very similar. These positive stranded RNA viruses possess a single large open reading frame (ORF) encoding all the viral proteins necessary for virus replication. These proteins are expressed as a polyprotein that is co- and post-translationally processed by both cellular and virus-encoded proteinases to yield the mature viral proteins. The viral proteins responsible for the replication of the viral genome RNA are located within approximately the carboxy-terminal. Two-thirds of the ORF are termed nonstructural (NS) proteins. The genetic organization and polyprotein processing of the nonstructural protein portion of the ORF for pestiviruses and hepaciviruses is very similar. For both the pestiviruses and hepaciviruses, the mature nonstructural (NS) proteins, in sequential order from the amino-terminus of the nonstructural protein coding region to the carboxy-terminus of the ORF, consist of p7, NS2, NS3, NS4A, NS4B, NS5A, and NS5B.

The NS proteins of pestiviruses and hepaciviruses share sequence domains that are characteristic of specific protein functions. For example, the NS3 proteins of viruses in both groups possess amino acid sequence motifs characteristic of serine proteinases and of helicases (Gorbalenya et al., *Nature*, 1988, 333, 22; Bazan and Fletterick *Virology*, 1989, 171, 637-639; Gorbalenya et al., *Nucleic Acid Res.*, 1989, 17, 3889-3897). Similarly, the NS5B proteins of pestiviruses and hepaciviruses have the motifs characteristic of RNA-directed RNA polymerases (Koonin, E. V. and Dolja, V. V., *Crit. Rev. Biochem. Molec. Biol.* 1993, 28, 375-430).

The actual roles and functions of the NS proteins of pestiviruses and hepaciviruses in the lifecycle of the viruses are directly analogous. In both cases, the NS3 serine proteinase is responsible for all proteolytic processing of polyprotein precursors downstream of its position in the ORF (Wiskerchen and Collett, *Virology*, 1991, 184, 341-350; Bartenschlager et al., *J. Virol.* 1993, 67, 3835-3844; Eckart et al. *Biochem. Biophys. Res. Comm.* 1993, 192, 399-406; Grakoui et al., *J. Virol.* 1993, 67, 2832-2843; Grakoui et al., *Proc. Natl. Acad. Sci. USA* 1993, 90, 10583-10587; Hijikata et al., *J. Virol.* 1993, 67, 4665-4675; Tome et al., *J. Virol.*, 1993, 67, 4017-4026). The NS4A protein, in both cases, acts as a cofactor with the NS3 serine protease (Bartenschlager et al., *J. Virol.* 1994, 68, 5045-5055; Failla et al., *J. Virol.* 1994, 68, 3753-3760; Xu et al., *J. Virol.*, 1997, 71:53 12-5322). The NS3 protein of both viruses also functions as a helicase (Kim et al., *Biochem. Biophys. Res. Comm.*, 1995, 215, 160-166; Jin and Peterson, *Arch. Biochem. Biophys.*, 1995, 323, 47-53; Warrener and Collett, *J. Virol.* 1995, 69, 1720-1726). Finally, the NS5B proteins of pestiviruses and hepaciviruses have the predicted RNA-directed RNA polymerases activity (Behrens et al., EMBO, 1996, 15, 12-22; Lechmann et al., *J. Virol.*, 1997, 71, 8416-8428; Yuan et al., *Biochem. Biophys. Res. Comm.* 1997, 232, 231-235; Hagedorn, PCT WO 97/12033; Zhong et al, *J. Virol.*, 1998, 72, 9365-9369).

Currently, there are limited treatment options for individuals infected with hepatitis C virus. The current approved therapeutic option is the use of immunotherapy with recombinant interferon-α alone or in combination with the nucleoside analog ribavirin. This therapy is limited in its clinical effectiveness and only 50% of treated patients respond to therapy. Therefore, there is significant need for more effective and novel therapies to address the unmet medical need posed by HCV infection.

A number of potential molecular targets for drug development of direct acting antivirals as anti-HCV therapeutics have now been identified including, but not limited to, the NS2-NS3 autoprotease, the N3 protease, the N3 helicase and the NS5B polymerase. The RNA-dependent RNA polymerase is absolutely essential for replication of the single-stranded, positive sense, RNA genome and this enzyme has elicited significant interest among medicinal chemists.

Inhibitors of HCV NS5B as potential therapies for HCV infection have been reviewed: Tan, S.-L., et al., *Nature Rev. Drug Discov.*, 2002, 1, 867-881; Walker, M. P. et al., *Exp. Opin. Investigational Drugs*, 2003, 12, 1269-1280; Ni, Z-J., et al., *Current Opinion in Drug Discovery and Development*, 2004, 7, 446-459; Beaulieu, P. L., et al., *Current Opinion in Investigational Drugs*, 2004, 5, 838-850; Wu, J., et al., *Current Drug Targets-Infectious Disorders*, 2003, 3, 207-219; Griffith, R. C., et al, *Annual Reports in Medicinal Chemistry*, 2004, 39, 223-237; Carrol, S., et al., *Infectious Disorders-Drug Targets*, 2006, 6, 17-29. The potential for the emergence of resistant HCV strains and the need to identify agents with broad genotype coverage supports the need for continuing efforts to identify novel and more effective nucleosides as HCV NS5B inhibitors.

Nucleoside inhibitors of NS5B polymerase can act either as a non-natural substrate that results in chain termination or as a competitive inhibitor which competes with nucleotide binding to the polymerase. To function as a chain terminator the nucleoside analog must be taken up by the cell and converted in vivo to a triphosphate to compete for the polymerase nucleotide binding site. This conversion to the triphosphate is commonly mediated by cellular kinases which imparts additional structural requirements on a potential nucleoside polymerase inhibitor. Unfortunately, this limits the direct evaluation of nucleosides as inhibitors of HCV replication to cell-based assays capable of in situ phosphorylation.

In some cases, the biological activity of a nucleoside is hampered by its poor substrate characteristics for one or more of the kinases needed to convert it to the active triphosphate form. Formation of the monophosphate by a nucleoside kinase is generally viewed as the rate limiting step of the three phosphorylation events. To circumvent the need for the initial phosphorylation step in the metabolism of a nucleoside to the active triphosphate analog, the preparation of stable phosphate prodrugs has been reported. Nucleoside phosphoramidate prodrugs have been shown to be precursors of the active nucleoside triphosphate and to inhibit viral replication when administered to viral infected whole cells (McGuigan, C., et al., *J. Med. Chem.*, 1996, 39, 1748-1753; Valette, G., et al., *J. Med. Chem.*, 1996, 39, 1981-1990; Balzarini, J., et al., *Proc. National Acad Sci USA*, 1996, 93, 7295-7299; Siddiqui, A. Q., et al., *J. Med. Chem.*, 1999, 42, 4122-4128; Eisenberg, E. J., et al., *Nucleosides, Nucleotides and Nucleic Acids*, 2001, 20, 1091-1098; Lee, W. A., et al., *Antimicrobial Agents and Chemotherapy*, 2005, 49, 1898); US 2006/0241064; and WO 2007/095269.

Also limiting the utility of nucleosides as viable therapeutic agents is their sometimes poor physicochemical and pharmacokinetic properties. These poor properties can limit the intestinal absorption of an agent and limit uptake into the target tissue or cell. To improve on their properties prodrugs of nucleosides have been employed. It has been demonstrated that preparation of nucleoside phosphoramidates improves the systemic absorption of a nucleoside and furthermore, the phosphoramidate moiety of these "pronucleotides" is masked with neutral lipophilic groups to obtain a suitable partition coefficient to optimize uptake and transport into the cell dramatically enhancing the intracellular concentration of the nucleoside monophosphate analog relative to administering the parent nucleoside alone. Enzyme-mediated hydrolysis of the phosphate ester moiety produces a nucleoside monophosphate wherein the rate limiting initial phosphorylation is unnecessary. To this end, U.S. patent application Ser. No. 12/053,015, which corresponds to WO 2008/121634 and US 2010/0016251, discloses a number of phosphoramidate nucleoside prodrugs, many of which show activity in an HCV assay. Several compounds disclosed in US 2010/0016251 were tested as a potential clinical candidate for approval by the FDA.

SUMMARY OF THE INVENTION

Disclosed herein is a compound represented by formula 4 and its respective phosphorus-based diastereomers represented by formulas $S_P$-4 and $R_P$-4.

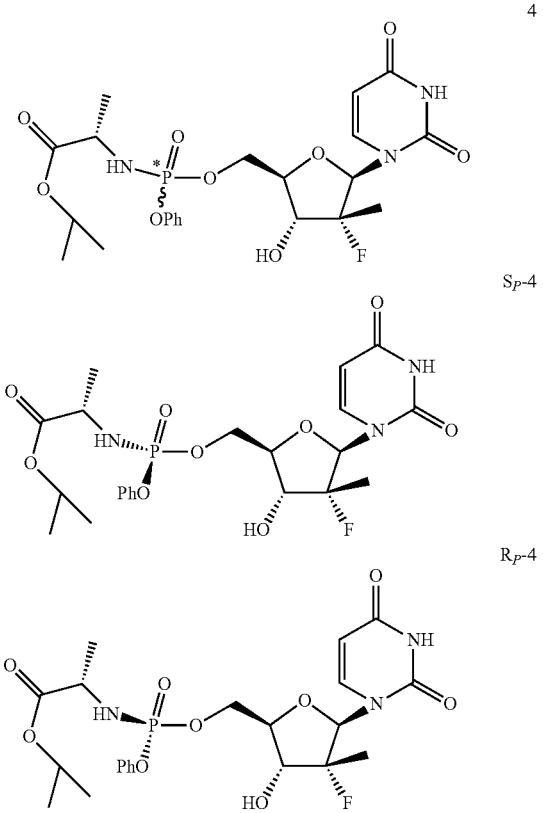

DETAILED DESCRIPTION OF THE INVENTION

Definitions

Figure 1:
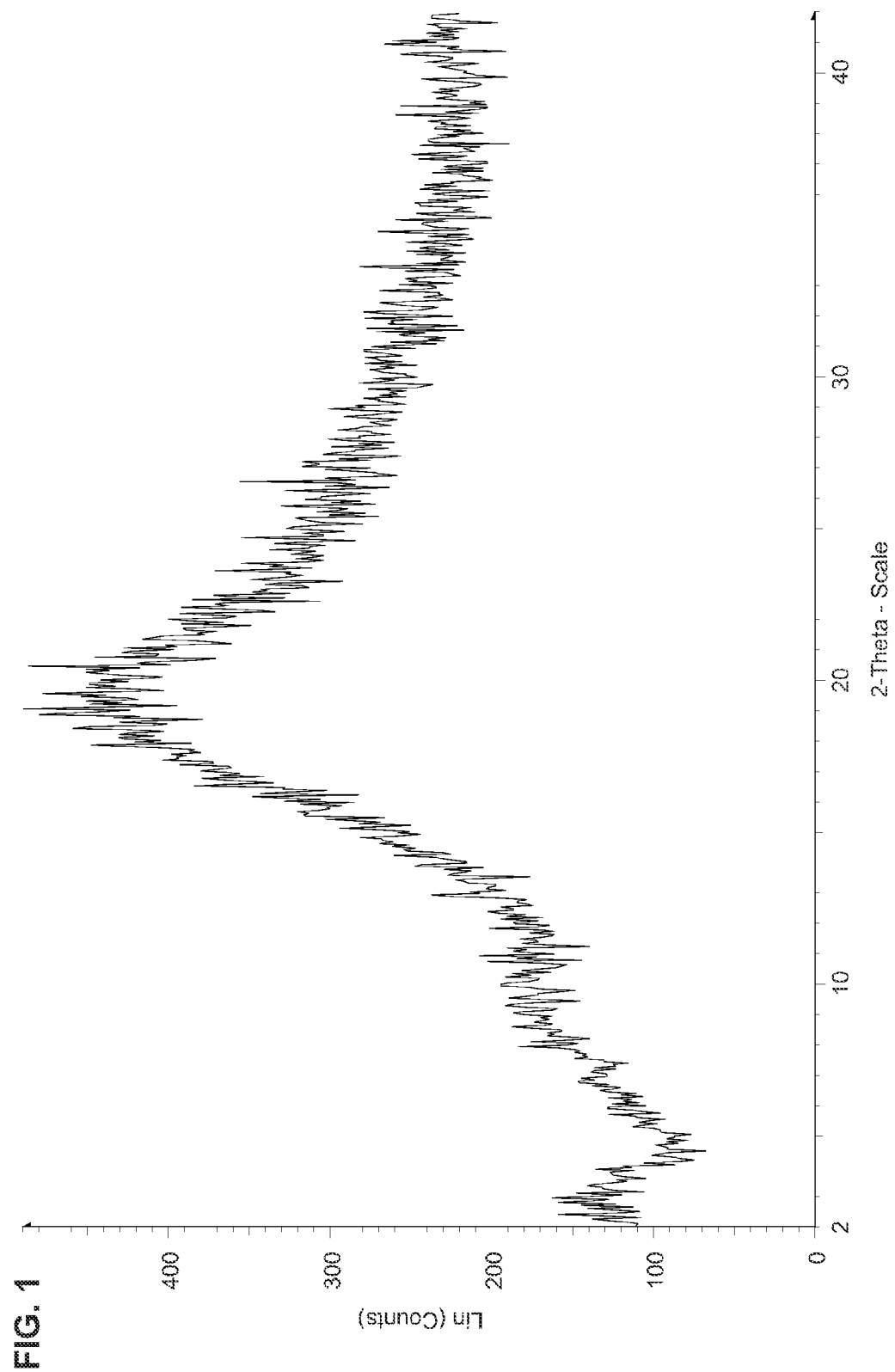
FIG. 1. High resolution XRD diffractogram of 4.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "P*" means that the phosphorus atom is chiral and that it has a corresponding Cahn-Ingold-Prelog designation of "R" or "S" which have their accepted plain meanings.

The term "purified," as described herein, refers to the purity of a given compound. For example, a compound is "purified" when the given compound is a major component of the composition, i.e., at least 50% w/w pure. Thus, "purified" embraces at least 50% w/w purity, at least 60% w/w purity, at least 70% purity, at least 80% purity, at least 85% purity, at least 90% purity, at least 92% purity, at least 94% purity, at least 96% purity, at least 97% purity, at least 98% purity, at least 99% purity, at least 99.5% purity, and at least 99.9% purity, wherein "substantially pure" embraces at least 97% purity, at least 98% purity, at least 99% purity, at least 99.5% purity, and at least 99.9% purity.

The term "metabolite," as described herein, refers to a compound produced in vivo after administration to a subject in need thereof.

The term "about" (also represented by ~) means that the recited numerical value is part of a range that varies within standard experimental error.

The expression "substantially as shown in . . . " a specified XRPD pattern means that the peak positions shown in the XRPD pattern are substantially the same, within visual inspection or resort to selected peak listings (±0.2° 2θ). One of ordinary skill understands that the intensities can vary depending on the sample.

The term "substantially anhydrous" means that a substance contains at most 10% by weight of water, preferably at most 1% by weight of water, more preferably at most 0.5% by weight of water, and most preferably at most 0.1% by weight of water.

A solvent or anti-solvent (as used in reactions, crystallization, etc. or lattice and/or adsorbed solvents) includes at least one of a $C_1$ to $C_8$ alcohol, a $C_2$ to $C_8$ ether, a $C_3$ to $C_7$ ketone, a $C_3$ to $C_7$ ester, a $C_1$ to $C_2$ chlorocarbon, a $C_2$ to $C_7$ nitrile, a miscellaneous solvent, a $C_5$ to $C_{12}$ saturated hydrocarbon, and a $C_6$ to $C_{12}$ aromatic hydrocarbon.

The $C_1$ to $C_8$ alcohol refers to a straight/branched and/or cyclic/acyclic alcohol having such number of carbons. The $C_1$ to $C_8$ alcohol includes, but is not limited to, methanol, ethanol, n-propanol, isopropanol, isobutanol, hexanol, and cyclohexanol.

The $C_2$ to $C_8$ ether refers to a straight/branched and/or cyclic/acyclic ether having such number of carbons. The $C_2$ to $C_8$ ether includes, but is not limited to, dimethyl ether, diethyl ether, di-isopropyl ether, di-n-butyl ether, methyl-t-butyl ether (MTBE), tetrahydrofuran, and dioxane The $C_3$ to $C_7$ ketone refers to a straight/branched and/or cyclic/acyclic ketone having such number of carbons. The $C_3$ to $C_7$ ketone includes, but is not limited to, acetone, methyl ethyl ketone, propanone, butanone, methyl isobutyl ketone, methyl butyl ketone, and cyclohexanone.

The $C_3$ to $C_7$ ester refers to a straight/branched and/or cyclic/acyclic ester having such number of carbons. The $C_3$ to $C_7$ ester includes, but is not limited to, ethyl acetate, propyl acetate, n-butyl acetate, etc.

The $C_1$ to $C_2$ chlorocarbon refers to a chlorocarbon having such number of carbons. The $C_1$ to $C_2$ chlorocarbon includes, but is not limited to, chloroform, methylene chloride (DCM), carbon tetrachloride, 1,2-dichloroethane, and tetrachloroethane.

A $C_2$ to $C_7$ nitrile refers to a nitrile have such number of carbons. The $C_2$ to $C_7$ nitrile includes, but is not limited to, acetonitrile, propionitrile, etc.

A miscellaneous solvent refers to a solvent commonly employed in organic chemistry, which includes, but is not limited to, diethylene glycol, diglyme (diethylene glycol dimethyl ether), 1,2-dimethoxy-ethane, dimethylformamide, dimethylsulfoxide, ethylene glycol, glycerin, hexamethylphsphoramide, hexamethylphosphorous triame, N-methyl-2-pyrrolidinone, nitromethane, pyridine, triethyl amine, and acetic acid.

The term $C_5$ to $C_{12}$ saturated hydrocarbon refers to a straight/branched and/or cyclic/acyclic hydrocarbon. The $C_5$ to $C_{12}$ saturated hydrocarbon includes, but is not limited to, n-pentane, petroleum ether (ligroine), n-hexane, n-heptane, cyclohexane, and cycloheptane.

The term $C_6$ to $C_{12}$ aromatic refers to substituted and unsubstituted hydrocarbons having a phenyl group as their backbone. Preferred hydrocarbons include benzene, xylene, toluene, chlorobenzene, o-xylene, m-xylene, p-xylene, xylenes, with toluene being more preferred.

The term "halo" or "halogen" as used herein, includes chloro, bromo, iodo and fluoro.

The term "blocking group" refers to a chemical group which exhibits the following characteristics. The "group" is derived from a "protecting compound." Groups that are selective for primary hydroxyls over secondary hydroxyls that can be put on under conditions consistent with the stability of the phosphoramidate (pH 2-8) and impart on the resulting product substantially different physical properties allowing for an easier separation of the 3'-phosphoramidate-5'-new group product from the unreacted desired compound. The group must react selectively in good yield to give a protected substrate that is stable to the projected reactions (see Protective Groups in Organic Synthesis, $3^{nd}$ ed. T. W. Greene and P. G. M. Wuts, John Wiley & Sons, New York, N.Y., 1999). Examples of groups include, but are not limited to: benzoyl, acetyl, phenyl-substituted benzoyl, tetrahydropyranyl, trityl, DMT (4,4'-dimethoxytrityl), MMT (4-monomethoxytrityl), trimethoxytrityl, pixyl(9-phenylxanthen-9-yl) group, thiopixyl(9-phenylthioxanthen-9-yl) or 9-(p-methoxyphenyl)xanthine-9-yl (MOX), etc.; C(O)-alkyl, C(O)Ph, C(O)aryl, $CH_2O$-alkyl, $CH_2O$-aryl, $SO_2$-alkyl, $SO_2$-aryl, tert-butyldimethylsilyl, tert-butyldiphenylsilyl. Acetals, such as MOM or THP and the like are considered possible groups. Fluorinated compounds are also contemplated in so far that they can be attached to the compound and can be selectively removed by passing through a fluorous solid phase extraction media (Fluoro-Flash®). A specific example includes a fluorinated trityl analog, trityl analog 1-[4-(1H,1H,2H,2H-perfluorodecyl) phenyl)-1,1-diphenylmethanol. Other fluorinated analogs of trityl, BOC, FMOC, CBz, etc. are also contemplated. Sulfonyl chlorides like p-toluenesulfonyl chloride can react selectively on the 5' position. Esters could be formed selectively such as acetates and benzoates. Dicarboxylic anhydrides such as succinic anhydride and its derivatives can be used to generate an ester linkage with a free carboxylic acid, such examples include, but are not limited to oxalyl, malonyl, succinyl, glutaryl, adipyl, pimelyl, superyl, azelayl, sebacyl, phthalyl, isophthalyl, terephthalyl, etc. The free carboxylic acid increases the polarity dramatically and can also be used as a handle to extract the reaction product into mildy basic aqueous phases such as sodium bicarbonate solutions. The phosphoramidate group is relatively stable in acidic media, so groups requiring acidic reaction conditions, such as, tetrahydropyranyl, could also be used.

The term "protecting group" which is derived from a "protecting compound," has its plain and ordinary meaning, i.e., at least one protecting or blocking group is bound to at least one functional group (e.g., —OH, —$NH_2$, etc.) that allows chemical modification of at least one other functional group. Examples of protecting groups, include, but are not limited to, benzoyl, acetyl, phenyl-substituted benzoyl, tetrahydropyranyl, trityl, DMT (4,4'-dimethoxytrityl), MMT (4-monomethoxytrityl), trimethoxytrityl, pixyl (9-phenylxanthen-9-yl) group, thiopixyl (9-phenylthioxanthen-9-yl) or 9-(p-methoxyphenyl)xanthine-9-yl (MOX), etc.; C(O)-alkyl, C(O)Ph, C(O)aryl, C(O)O(lower alkyl), C(O)O(lower alkylene)aryl (e.g., —C(O)OCH$_2$Ph), C(O)Oaryl, $CH_2O$-alkyl, $CH_2O$-aryl, $SO_2$-alkyl, $SO_2$-aryl, a protecting group comprising at least one silicon atom, such as, tert-butyldimethylsilyl, tert-butyldiphenylsilyl, Si(lower alkyl)$_2$OSi (lower alkyl)$_2$OH (such as, —Si($^i$Pr)$_2$OSi($^i$Pr)$_2$OH.

The term "protecting compound," as used herein and unless otherwise defined, refers to a compound that contains a "protecting group" and that is capable of reacting with a compound that contains functional groups that are capable of being protected.

The term "leaving group", as used herein, has the same meaning to the skilled artisan (Advanced Organic Chemistry: reactions, mechanisms and structure—Fourth Edition by Jerry March, John Wiley and Sons Ed.; 1992 pages 351-357) and represents a group which is part of and attached to a substrate molecule; in a reaction where the substrate molecule undergoes a displacement reaction (with for example a nucleophile), the leaving group is then displaced. Examples of leaving groups include, but are not limited to: halogen (F, Cl, Br, and I), preferably Cl, Br, or I; tosylate, mesylate, triflate, acetate, camphorsulfonate, aryloxide, and aryloxide substituted with at least one electron withdrawing group (e.g., p-nitrophenoxide, 2-chlorophenoxide, 4-chlorophenoxide, 2,4-dinitrophenoxide, pentafluorophenoxide, etc.), etc. The term "electron withdrawing group" is accorded its plain meaning here. Examples of electron withdrawing groups include, but are not limited to, a halogen, —NO2, —C(O)(lower alkyl), —C(O)(aryl), —C(O)O (lower alkyl), —C(O)O(aryl), etc.

The term "basic reagent", as used herein, means a compound that is capable of deprotonating a hydroxyl group. Examples of basic reagents include, but are not limited to, a (lower alk)oxide ((lower alkyl)OM) in combination with an alcoholic solvent, where (lower alk)oxides include, but are not limited to, MeO$^-$, EtO$^-$, $^n$PrO$^-$, $^i$PrO$^-$, $^t$BuO$^-$, $^i$AmO- (iso-amyloxide), etc., and where M is an alkali metal cation, such as Li$^+$, Na$^+$, K$^+$, etc. Alcoholic solvents include (lower alkyl)OH, such as, for example, MeOH, EtOH, $^n$PrOH, $^i$PrOH, $^t$BuOH, $^i$AmOH, etc. Non-alkoxy bases can also be used such as sodium hydride, sodium hexamethyldisilazane, lithium hexamethyldisilazane, lithium diisopropylamide, calcium hydride, sodium carbonate, potassium carbonate, cesium carbonate, DBU, DBN, Grignard reagents, such as (lower alkyl)Mg(halogen), which include but are not limited to MeMgCl, MeMgBr, $^t$BuMgCl, $^t$BuMgBr, etc.

The term "base" embraces the term "basic reagent" and is meant to be a compound that is capable of deprotonating a proton containing compound, i.e., a Bronsted base. In addition to the examples recited above, further examples of a base include, but are not limited to pyridine, collidine, 2,6-(loweralkyl)-pyridine, dimethyl-aniline, imidazole, N-methyl-imidazole, pyrazole, N-methyl-pyrazole, triethylamine, di-isopropylethylamine, etc.

The term "electron withdrawing group" is accorded its plain meaning Examples of electron withdrawing groups include, but are not limited to, a halogen (F, Cl, Br, or I), —NO$_2$, —C(O)(lower alkyl), —C(O)(aryl), —C(O)O (lower alkyl), —C(O)O(aryl), etc.

The term "co-crystallates" include co-crystallates of 4, R$_P$-4, or S$_P$-4 in combination with salts, which embraces pharmaceutically acceptable salts.

The term "salts," as described herein, refers to a compound comprising a cation and an anion, which can be produced by the protonation of a proton-accepting moiety and/or deprotonation of a proton-donating moiety. It should be noted that protonation of the proton-accepting moiety results in the formation of a cationic species in which the charge is balanced by the presence of a physiological anion, whereas deprotonation of the proton-donating moiety results in the formation of an anionic species in which the charge is balanced by the presence of a physiological cation.

The phrase "pharmaceutically acceptable salt" means a salt that is pharmaceutically acceptable. Examples of pharmaceutically acceptable salts include, but are not limited to: (1) acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like or (2) basic addition salts formed with the conjugate bases of any of the inorganic acids listed above, wherein the conjugate bases comprise a cationic component selected from among Na$^+$, K$^+$, Mg$^{2+}$, Ca$^{2+}$, NH$_g$R'''$_{4-g}^+$, in which R''' is a C$_{1-3}$ alkyl and g is a number selected from among 0, 1, 2, 3, or 4. It should be understood that all references to pharmaceutically acceptable salts include solvent addition forms (solvates) or crystal forms (polymorphs) as defined herein, of the same acid addition salt.

The term "alkyl" refers to an unbranched or branched chain, saturated, monovalent hydrocarbon residue containing 1 to 30 carbon atoms. The term "C$_{1-M}$ alkyl" refers to an alkyl comprising 1 to M carbon atoms, where M is an integer having the following values: 2, 3, 4, 5, 6, 7, 8, 9, 10, 11, 12, 13, 14, 15, 16, 17, 18, 19, 20, 21, 22, 23, 24, 25, 26, 27, 28, 29, or 30. The term "C$_{1-4}$ alkyl" refers to an alkyl containing 1 to 4 carbon atoms. The term "lower alkyl" denotes a straight or branched chain hydrocarbon residue comprising 1 to 6 carbon atoms. "C$_{1-20}$ alkyl" as used herein refers to an alkyl comprising 1 to 20 carbon atoms. "C$_{1-10}$ alkyl" as used herein refers to an alkyl comprising 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl. The term (ar)alkyl or (heteroaryl)alkyl indicate the alkyl group is optionally substituted by an aryl or a heteroaryl group respectively.

The term "alkenyl" refers to an unsubstituted hydrocarbon chain radical having from 2 to 10 carbon atoms having one or two olefinic double bonds, preferably one olefinic double bond. The term "C$_{2-N}$ alkenyl" refers to an alkenyl comprising 2 to N carbon atoms, where N is an integer having the following values: 3, 4, 5, 6, 7, 8, 9, or 10. The term "C$_{2-10}$ alkenyl" refers to an alkenyl comprising 2 to 10 carbon atoms. The term "C$_{2-4}$ alkenyl" refers to an alkenyl comprising 2 to 4 carbon atoms. Examples include, but are not limited to, vinyl, 1-propenyl, 2-propenyl (allyl) or 2-butenyl (crotyl).

The term "aryl," as used herein, and unless otherwise specified, refers to substituted or unsubstituted phenyl (Ph), biphenyl, or naphthyl, preferably the term aryl refers to substituted or unsubstituted phenyl. The aryl group can be substituted with one or more moieties selected from among hydroxyl, F, Cl, Br, I, amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in T. W. Greene and P. G. M. Wuts, "Protective Groups in Organic Synthesis," 3rd ed., John Wiley & Sons, 1999.

The term "aryloxide," as used herein, and unless otherwise specified, refers to substituted or unsubstituted phenoxide (PhO—), p-phenyl-phenoxide (p-Ph-PhO—), or naphthoxide, preferably the term aryloxide refers to substituted or unsubstituted phenoxide. The aryloxide group can be substituted with one or more moieties selected from among hydroxyl, F, Cl, Br, I, —C(O)(lower alkyl), —C(O)O(lower alkyl), amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in T. W. Greene and P. G. M. Wuts, "Protective Groups in Organic Synthesis," 3rd ed., John Wiley & Sons, 1999.

The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use.

The term "crystalline" refers to a situation where a solid sample of either S$_P$-4 or R$_P$-4 has crystalline characteristics when determined by X-ray powder diffraction or a single crystal X-ray technique.

The term "crystal-like" refers to a situation where a solid sample of either S$_P$-4 or R$_P$-4 has crystalline characteristics when determined by one means, e.g., visually or by optical or polarizing microscopy, but does not have crystalline characteristics when determined by another means, e.g., x-ray powder diffraction. Methods of visually determining the crystallinity of a solid sample by visual or by optical or by polarizing microscopy are disclosed in USP <695> and <776>, both of which are incorporated by reference. A solid sample of either $S_P$-4 or $R_P$-4 that is "crystal-like" may be crystalline under certain conditions but may become non-crystalline when subjected to other conditions.

The term "amorphous" refers to a situation where a solid sample of either $S_P$-4 or $R_P$-4 is neither crystalline nor crystal-like.

Embodiments

A first embodiment is directed to a compound represented by formula 4:

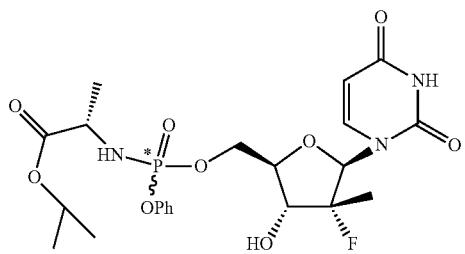

4 wherein P* represents a chiral phosphorus atom. Due to the chiral phosphorus atom, the compound represented by formula 4 comprises two diastereomers designated as $R_P$-4 and $S_P$-4. The compound represented by formula 4 can also be part of a solvate, a hydrate, or a mixed solvate/hydrate. The solvate is designated as 4.nS, while the hydrate is designated as 4.mH$_2$O, where S is a lattice solvent, n varies by an integer or non-integer amount from about 0 to about 3 and m varies by an integer or non-integer amount from about 0 to about 5. Finally, the compound represented by formula 4 might not exist as a solvate or hydrate, but have a certain advantageous amount of adsorbed solvent (S) or water. In which case, the amount of S or water can vary from about 0 wt. % to about 10 wt. % based on the weight of the compound represented by formula 4. The compound represented by formula 4 and its solvates and hydrates thereof is crystalline, crystal-like, or amorphous.

A second embodiment is directed to a compound represented by formula $R_P$-4:

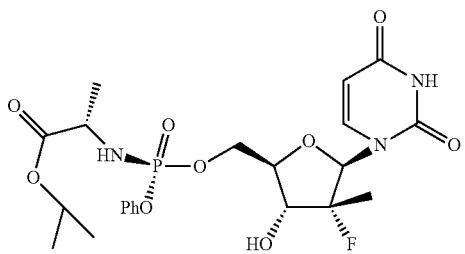

$R_P$-4

The compound represented by formula $R_P$-4 can also be part of a solvate, a hydrate, or a mixed solvate/hydrate. The solvate is designated as $R_P$-4.nS, while the hydrate is designated as $S_P$-4.mH$_2$O, where S is a lattice solvent, n varies by an integer or non-integer amount from about 0 to about 3 and m varies by an integer or non-integer amount from about 0 to about 5. Finally, the compound represented by formula $R_P$-4 might not exist as a solvate, hydrate, or mixed solvate/hydrate, but have a certain advantageous amount of adsorbed solvent (S), water, or both S and water. In which case, the amount of S or water can vary from about 0 wt. % to about 10 wt. % based on the weight of the compound represented by formula $R_P$-4. The compound represented by formula $R_P$-4 and its solvates and hydrates thereof is crystalline, crystal-like, or amorphous.

A first aspect of the second embodiment is directed to crystalline $R_P$-4.

A second aspect of the second embodiment is directed to crystalline $R_P$-4 having XRPD 2θ-reflections (°) at about: 6.6, 7.1, 9.0, 11.6, 17.9, 20.7, 24.1, 24.4, and 26.2.

A third aspect of the second embodiment is directed to a crystalline $R_P$-4 having XRPD 2θ-reflections (°) at about: 6.6, 7.1, 9.0, 11.0, 11.6, 12.0, 16.0, 17.9, 19.6, 20.7, 21.0, 21.7, 21.9, 22.2, 23.1, 24.1, 24.4, 26.1, 27.3, 27.7, and 28.2.

Figure 2:
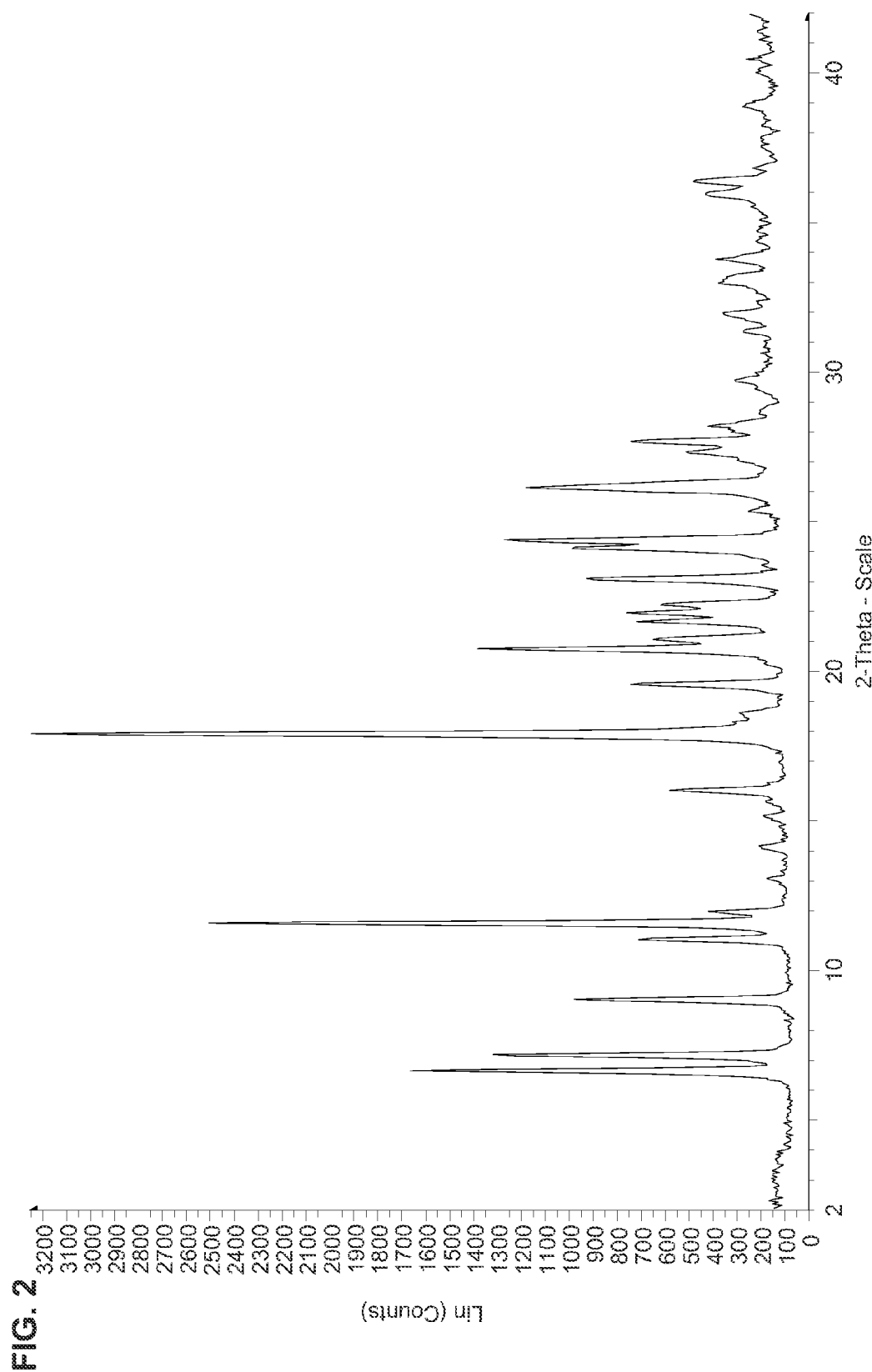
FIG. 2. High resolution XRD diffractogram of $R_P$-4.
Figure 3:
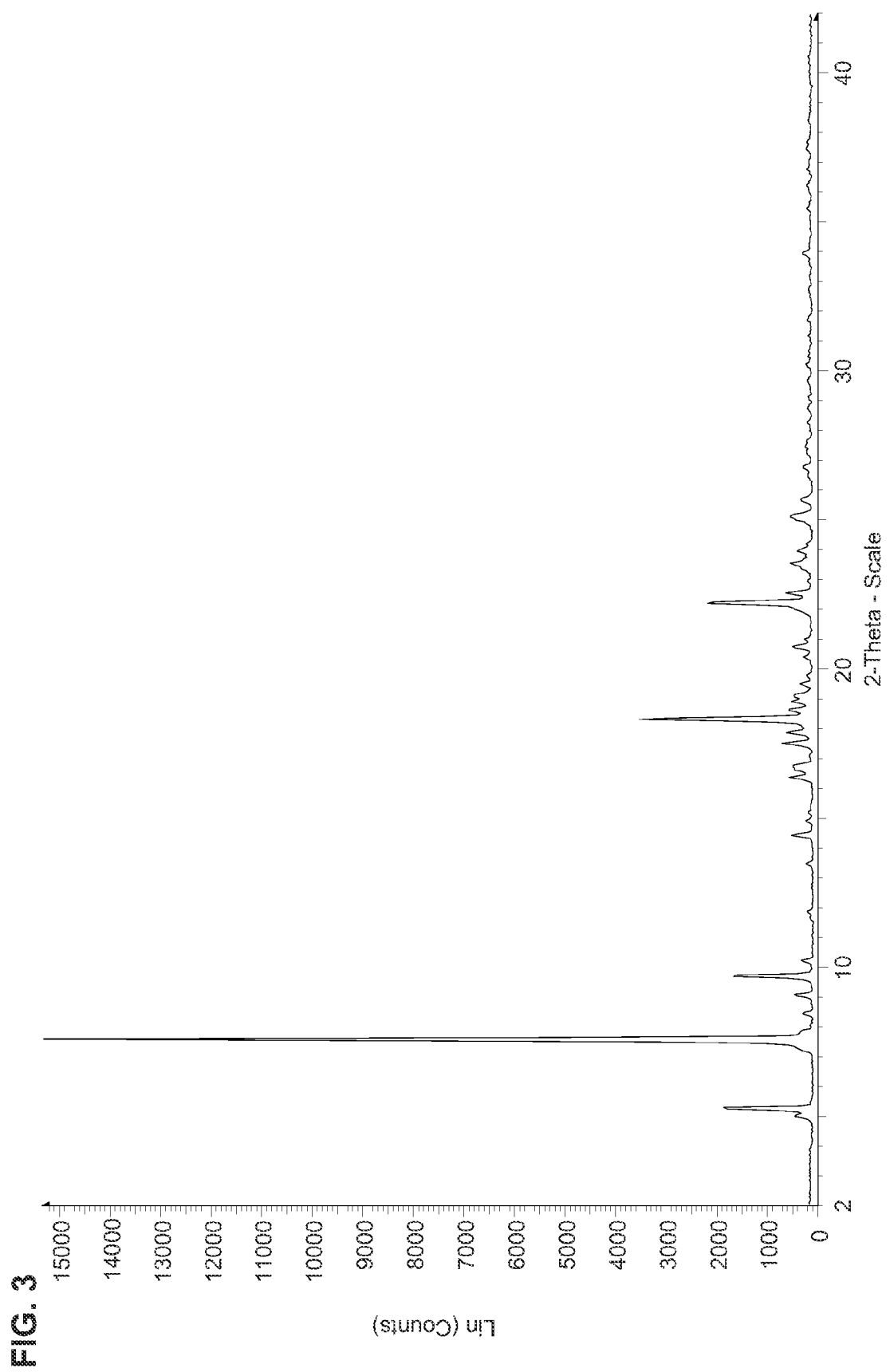
FIG. 3. High resolution XRD diffractogram of $S_P$-4 (Form 1).

A fourth aspect of the second embodiment is directed to crystalline $R_P$-4 having an XRPD diffraction pattern substantially as that shown in FIG. 2.

A fifth aspect of the second embodiment is directed to $R_P$-4 having the following FT-IR peaks (cm$^{-1}$): 1742, 1713, 1679, 1460, 1377, 1259, 1157, and 1079.

Figure 15:
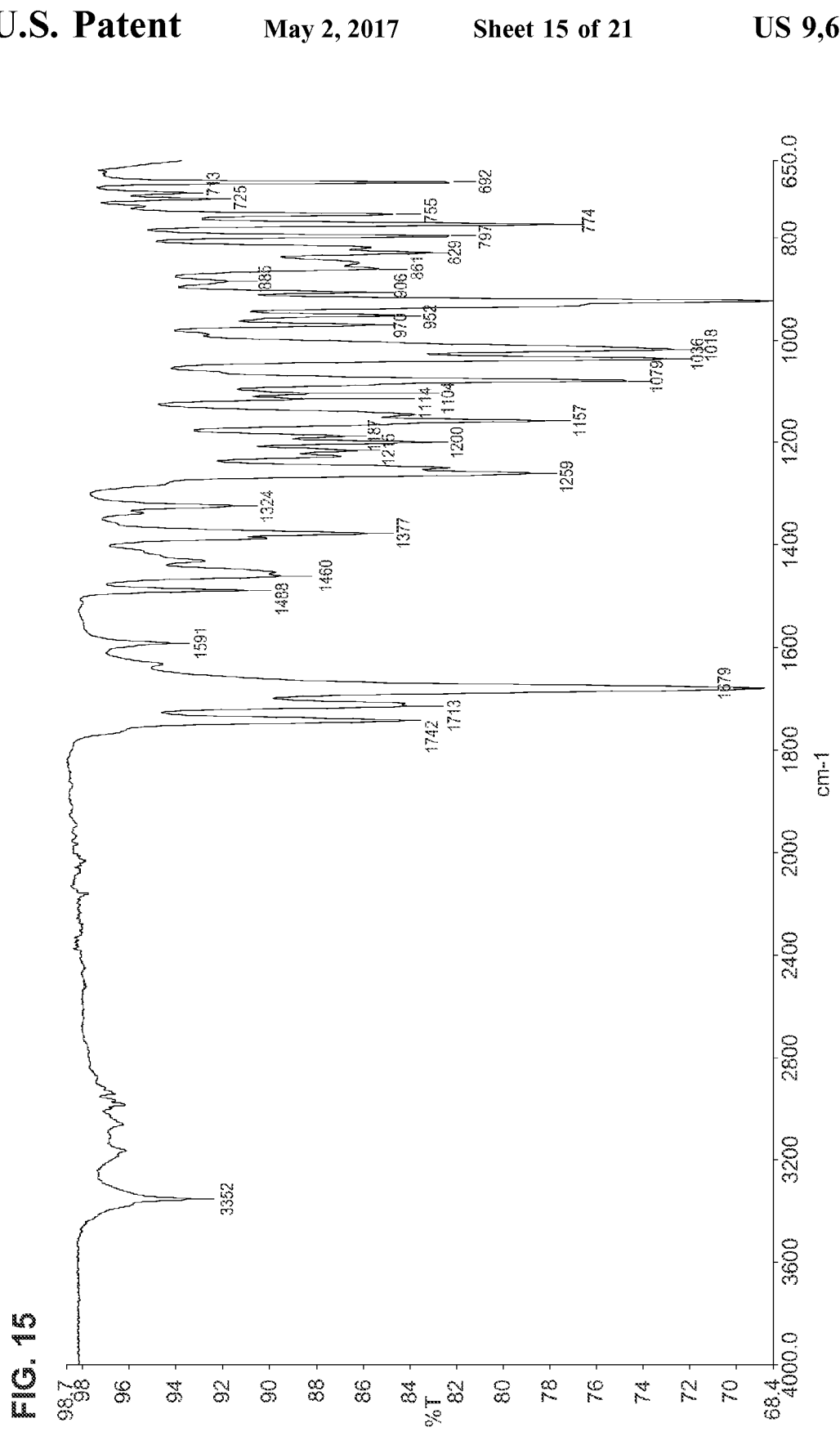
FIG. 15. FT-IR spectrum of $R_P$-4.

A sixth aspect of the second embodiment is directed to $R_P$-4 having an FT-IR spectrum substantially as that shown in FIG. 15.

A seventh aspect of the second embodiment is directed to substantially pure $R_P$-4.

An eighth aspect of the second embodiment is directed to substantially pure crystalline $R_P$-4.

A ninth aspect of the second embodiment is directed to substantially pure amorphous $R_P$-4.

A third embodiment is directed to a compound represented by formula $S_P$-4:

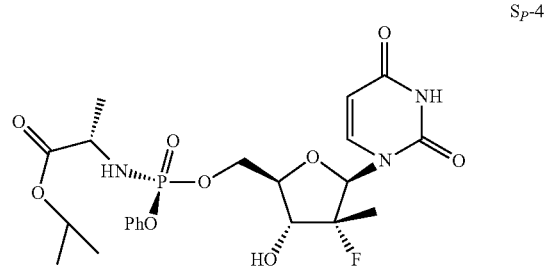 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

$S_P$-4

The compound represented by formula $S_P$-4 can also be part of a solvate, a hydrate, or a mixed solvate/hydrate. The solvate is designated as $S_P$-4.nS, while the hydrate is designated as $S_P$-4.mH$_2$O, where S is a lattice solvent, n varies in an integer or non-integer amount from about 0 to about 3 and m varies in an integer or non-integer amount from about 0 to about 5. Finally, the compound represented by formula $S_P$-4 might not exist as a solvate or hydrate, but have a certain advantageous amount of adsorbed solvent (S) or water. In which case, the amount of S or water can vary from about 0 wt. % to about 10 wt. % based on the weight of the compound represented by formula $S_P$-4. The compound represented by formula $S_P$-4 and its solvates and hydrates thereof is crystalline, crystal-like, or amorphous.

A first aspect of the third embodiment is directed to crystalline $S_P$-4.

A second aspect of the third embodiment is directed to a monoclinic crystalline $S_P$-4, preferably having the following unit cell parameters a~12.88 Å, b~6.17 Å, c~17.73 Å, and β~92.05°.

A third aspect of the third embodiment is directed to a monoclinic crystalline $S_P$-4, preferably having the following unit cell parameters a~20.09 Å, b~6.10 Å, c~23.01 Å, and β~112.29°.

A fourth aspect of the third embodiment is directed to a monoclinic crystalline $S_P$-4, preferably having the following unit cell parameters a~12.83 Å, b~6.15 Å, c~17.63 Å, and β~91.75°.

A fifth aspect of the third embodiment is directed to a monoclinic crystalline $S_P$-4, preferably having the following unit cell parameters a~12.93 Å, b~6.18 Å, c~18.01 Å, and β~96.40°.

A sixth aspect of the third embodiment is directed to a crystalline $S_P$-4 having XRPD 2θ-reflections (°) at about: 5.2, 7.5, 9.6, 16.7, 18.3, 22.2.

A seventh aspect of the third embodiment is directed to a crystalline $S_P$-4 having XRPD 2θ-reflections (°) at about: 5.0, 7.3, 9.4, and 18.1.

An eighth aspect of the third embodiment is directed to a crystalline $S_P$-4 having XRPD 2θ-reflections (°) at about: 4.9, 6.9, 9.8, 19.8, 20.6, 24.7, and 26.1.

A ninth aspect of the third embodiment is directed to a crystalline $S_P$-4 having XRPD 2θ-reflections (°) at about: 6.9, 9.8, 19.7, 20.6, and 24.6.

A ninth aspect of the third embodiment is directed to a crystalline $S_P$-4 having XRPD 2θ-reflections (°) at about: 5.0, 6.8, 19.9, 20.6, 20.9, and 24.9.

A tenth aspect of the third embodiment is directed to a crystalline $S_P$-4 having XRPD 2θ-reflections (°) at about: 5.2, 6.6, 7.1, 15.7, 19.1, and 25.0.

An eleventh aspect of the third embodiment is directed to crystalline $S_P$-4 having an XRPD diffraction pattern substantially as that shown in any one of FIG. 3, FIG. 4, FIG. 5, FIG. 6, FIG. 7, and FIG. 8.

A twelfth aspect of the third embodiment is directed to $S_P$-4 having the following FT-IR peaks (cm$^{-1}$) at about: 1743, 1713, 1688, 1454, 1378, 1208, and 1082.

Figure 7:
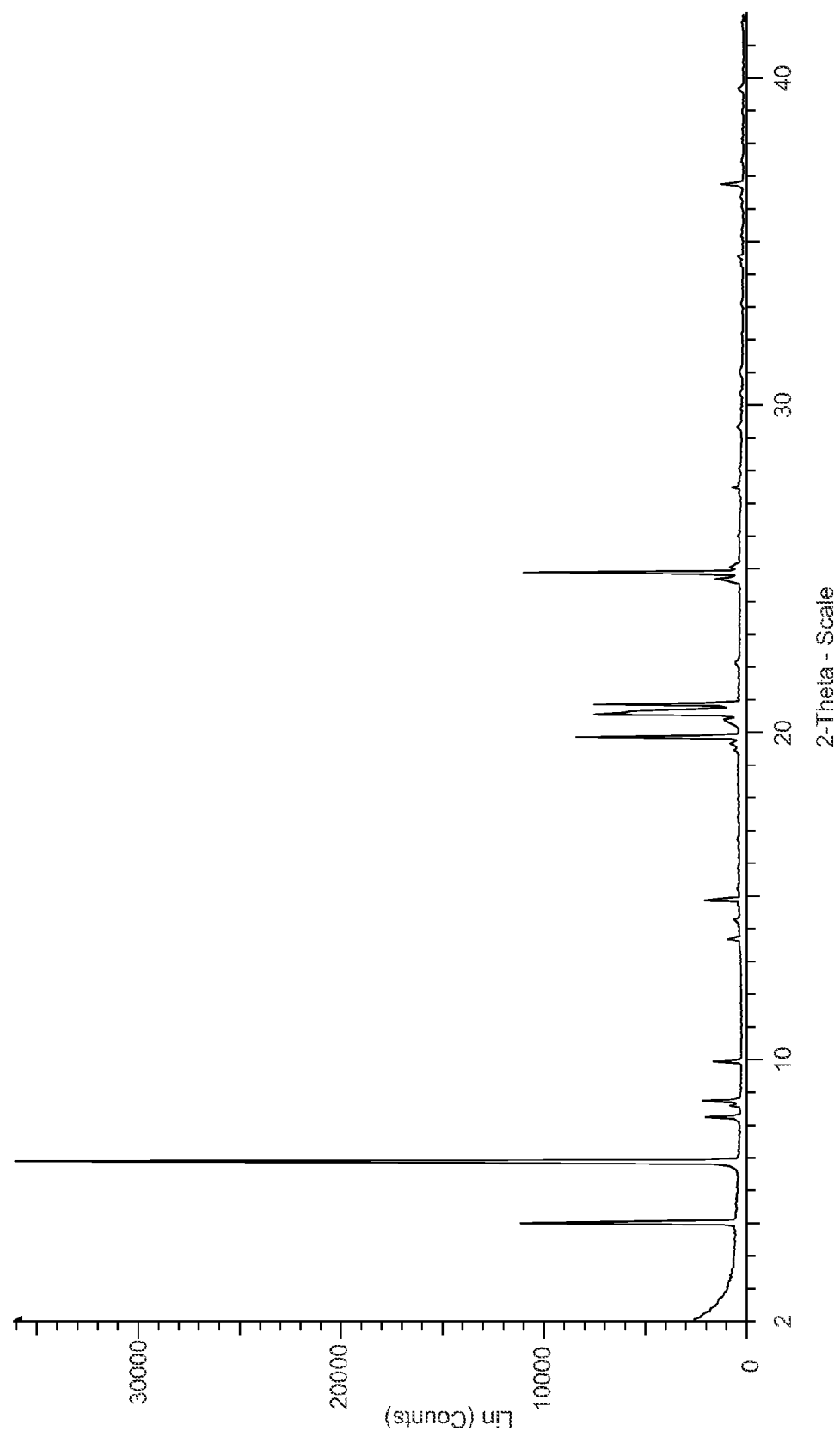
FIG. 7. High resolution XRD diffractogram of $S_P$-4 (Form 4).

A thirteenth aspect of the third embodiment is directed to $S_P$-4 having an FT-IR spectrum substantially as that shown in FIG. 7.

A fourteenth aspect of the third embodiment is directed to substantially pure $S_P$-4.

A fifteenth aspect of the third embodiment is directed to substantially pure crystalline $S_P$-4.

A sixteenth aspect of the third embodiment is directed to substantially pure amorphous $S_P$-4.

Dosage, Administration, and Use

A fourth embodiment is directed to a composition for the treatment and/or prophylaxis of any of the viral agents using any of compounds 4, $R_P$-4, or $S_P$-4. Possible viral agents include, but are not limited to: hepatitis C virus, hepatitis B virus, Hepatitis A virus, West Nile virus, yellow fever virus, dengue virus, rhinovirus, polio virus, bovine viral diarrhea virus, Japanese encephalitis virus, or those viruses belonging to the groups of Pestiviruses, hepaciviruses, or flavaviruses.

An aspect of this embodiment is directed to a composition for the treatment of any of the viral agents disclosed herein said composition comprising a pharmaceutically acceptable medium selected from among an excipient, carrier, diluent, and equivalent medium and any of compounds 4, $R_P$-4, or $S_P$-4, that is intended to include its hydrates, solvates, and any crystalline forms of any of compounds 4, $R_P$-4, or $S_P$-4 or its hydrates and solvates thereof.

The compounds 4, $R_P$-4, or $S_P$-4 may be independently formulated in a wide variety of oral administration dosage forms and carriers. Oral administration can be in the form of tablets, coated tablets, hard and soft gelatin capsules, solutions, emulsions, syrups, or suspensions. The compounds 4, $R_P$-4, or $S_P$-4 are efficacious when administered by suppository administration, among other routes of administration. The most convenient manner of administration is generally oral using a convenient daily dosing regimen which can be adjusted according to the severity of the disease and the patient's response to the antiviral medication.

The compounds 4, $R_P$-4, or $S_P$-4 together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as suspensions, emulsions, or filled capsules for oral use; or in the form of suppositories for rectal or vaginal administration. A typical preparation will contain from about 5% to about 95% active compound or compounds (w/w).

The compounds 4, $R_P$-4, or $S_P$-4 can be administered alone but will generally be administered in admixture with one or more suitable pharmaceutical excipients, diluents or carriers selected with regard to the intended route of administration and standard pharmaceutical practice.

Solid form preparations include, for example, powders, tablets, pills, capsules, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like. Examples of solid formulations are exemplified in EP 0524579; US 2002/0142050; US 2004/0224917; US 2005/0048116; US 2005/0058710; US 2006/0034937; US 2006/0057196; US 2006/0188570; US 2007/0026073; US 2007/0059360; US 2007/0077295; US 2007/0099902; US 2008/0014228; U.S. Pat. No. 6,267,985; U.S. Pat. No. 6,294,192; U.S. Pat. No. 6,383,471; U.S. Pat. No. 6,395,300; U.S. Pat. No. 6,569,463; U.S. Pat. No. 6,635,278; U.S. Pat. No. 6,645,528; U.S. Pat. No. 6,923,988; U.S. Pat. No. 6,932,983; U.S. Pat. No. 7,060,294; and U.S. Pat. No. 7,462,608, each of which is incorporated by reference.

Liquid formulations also are suitable for oral administration include liquid formulation including emulsions, syrups, elixirs and aqueous suspensions. These include solid form preparations which are intended to be converted to liquid form preparations shortly before use. Examples of liquid formulation are exemplified in U.S. Pat. Nos. 3,994,974; 5,695,784; and 6,977,257. Emulsions may be prepared in solutions, for example, in aqueous propylene glycol solutions or may contain emulsifying agents such as lecithin, sorbitan monooleate, or acacia. Aqueous suspensions can be prepared by dispersing the finely divided active component in water with viscous material, such as natural or synthetic gums, resins, methylcellulose, sodium carboxymethylcellulose, and other well known suspending agents.

The compounds 4, $R_P$-4, or $S_P$-4 may be independently formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds 4, $R_P$-4, or $S_P$-4 may be independently formulated for vaginal administration. Pessaries, tampons, creams, gels, pastes, foams or sprays containing in addition to the active ingredient such carriers as are known in the art to be appropriate. Certain of these formulations may also be used in conjunction with a condom with or without a spermicidal agent.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa., which is hereby incorporated by reference. A skilled formulation scientist may modify the formulations within the teachings of the specification to provide numerous formulations for a particular route of administration without rendering compositions containing the compounds contemplated herein unstable or compromising their therapeutic activity.

Additionally, the purified compounds 4, $R_P$-4, or $S_P$-4 may be independently formulated in conjunction with liposomes or micelles. As to liposomes, it is contemplated that the purified compounds can be formulated in a manner as disclosed in U.S. Pat. Nos. 4,797,285; 5,013,556; 5,077,056; 5,077,057; 5,154,930; 5,192,549; 5,213,804; 5,225,212; 5,277,914; 5,316,771; 5,376,380; 5,549,910; 5,567,434; 5,736,155; 5,827,533; 5,882,679; 5,891,468; 6,060,080; 6,132,763; 6,143,321; 6,180,134; 6,200,598; 6,214,375; 6,224,903; 6,296,870; 6,653,455; 6,680,068; 6,726,925; 7,060,689; and 7,070,801, each of which is incorporated by reference. As to micelles, it is contemplated that the purified compounds can be formulated in a manner as disclosed in U.S. Pat. Nos. 5,145,684 and 5,091,188, both of which are incorporated by reference.

The fifth embodiment is directed to a use of any of compounds 4, $R_P$-4, or $S_P$-4 in the manufacture of a medicament for the treatment of any condition the result of an infection by any one of the following viral agents: hepatitis C virus, West Nile virus, yellow fever virus, degue virus, rhinovirus, polio virus, hepatitis A virus, bovine viral diarrhea virus and Japanese encephalitis virus.

The term "medicament" means a substance used in a method of treatment and/or prophylaxis of a subject in need thereof, wherein the substance includes, but is not limited to, a composition, a formulation, a dosage form, and the like, comprising any of compounds 4, $R_P$-4, or $S_P$-4. It is contemplated that the use of any of compounds 4, $R_P$-4, or $S_P$-4 in the manufacture of a medicament, for the treatment of any of the antiviral conditions disclosed herein, either alone or in combination with another compound disclosed herein. A medicament includes, but is not limited to, any one of the compositions contemplated by the fourth embodiment disclosed herein.

A sixth embodiment is directed to a method of treatment and/or prophylaxis in a subject in need thereof said method comprises administering a therapeutically effective amount of any of compounds 4, $R_P$-4, or $S_P$-4 to the subject.

It is intended that a subject in need thereof is one that has any condition the result of an infection by any of the viral agents disclosed herein, which includes, but is not limited to, hepatitis C virus, West Nile virus, yellow fever virus, degue virus, rhinovirus, polio virus, hepatitis A virus, bovine viral diarrhea virus or Japanese encephalitis virus, flaviviridae viruses or pestiviruses or hepaciviruses or a viral agent causing symptoms equivalent or comparable to any of the above-listed viruses.

The term "subject" means a mammal, which includes, but is not limited to, cattle, pigs, sheep, chicken, turkey, buffalo, llama, ostrich, dogs, cats, and humans, preferably the subject is a human. It is contemplated that in the method of treating a subject thereof of the ninth embodiment can be any of the compounds contemplated herein, either alone or in combination with another compound disclosed herein.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.001 and about 10 g, including all values in between, such as 0.001, 0.0025, 0.005, 0.0075, 0.01, 0.025, 0.050, 0.075, 0.1, 0.125, 0.150, 0.175, 0.2, 0.25, 0.5, 0.75, 1, 1.5, 2, 2.5, 3, 3.5, 4, 4.5, 5, 5.5, 6, 6.5, 7, 7.5, 8, 8.5, 9, and 9.5, per day should be appropriate in monotherapy and/or in combination therapy. A particular daily dosage is between about 0.01 and about 1 g per day, including all incremental values of 0.01 g (i.e., 10 mg) in between, a preferred daily dosage about 0.01 and about 0.8 g per day, more preferably about 0.01 and about 0.6 g per day, and most preferably about 0.01 and about 0.25 g per day, each of which including all incremental values of 0.01 g in between. Generally, treatment is initiated with a large initial "loading dose" to rapidly reduce or eliminate the virus following by a decreasing the dose to a level sufficient to prevent resurgence of the infection. One of ordinary skill in treating diseases described herein will be able, without undue experimentation and in reliance on knowledge, experience and the disclosures of this application, to ascertain a therapeutically effective amount of the compound disclosed herein for a given disease and patient.

Therapeutic efficacy can be ascertained from tests of liver function including, but not limited to protein levels such as serum proteins (e.g., albumin, clotting factors, alkaline phosphatase, aminotransferases (e.g., alanine transaminase, aspartate transaminase), 5'-nucleosidase, γ-glutaminyltranspeptidase, etc.), synthesis of bilirubin, synthesis of cholesterol, and synthesis of bile acids; a liver metabolic function, including, but not limited to, carbohydrate metabolism, amino acid and ammonia metabolism. Alternatively the therapeutic effectiveness may be monitored by measuring HCV-RNA. The results of these tests will allow the dose to be optimized.

A first aspect of the sixth embodiment is directed to a method of treatment and/or prophylaxis in a subject in need thereof said method comprises administering to the subject a therapeutically effective amount of a compound represented by any of compounds 4, $R_P$-4, or $S_P$-4 and a therapeutically effective amount of another antiviral agent; wherein the administration is concurrent or alternative. It is understood that the time between alternative administration can range between 1-24 hours, which includes any subrange in between including, 2, 3, 4, 5, 6, 7, 8, 9, 10, 11, 12, 13, 14, 15, 16, 17, 18, 19, 20, 21, 22, and 23 hours.

Examples of "another antiviral agent" include, but are not limited to: HCV NS3 protease inhibitors (see EP 1881001, US 2003187018, US 2005267018, WO 2003006490, WO 200364456, WO 2004094452, WO 2005028502, WO 2005037214, WO 2005095403, WO 2007014920, WO 2007014921, WO 2007014922, WO 2007014925, WO 2007014926, WO 2007015824, WO 2008010921, and WO 2008010921); HCV NS5B Inhibitors (see US 2004229840, US 2005154056, US 2005-98125, US 20060194749, US 20060241064, US 20060293306, US 2006040890, US 2006040927, US 2006166964, US 2007275947, U.S. Pat. No. 6,784,166, US20072759300, WO 2002057287, WO 2002057425, WO 2003010141, WO 2003037895, WO 2003105770, WO 2004000858, WO 2004002940, WO 2004002944, WO 2004002977, WO 2004003138, WO 2004041201, WO 2004065367, WO 2004096210, WO 2005021568, WO 2005103045, WO 2005123087, WO 2006012078, WO 2006020082, WO 2006065335, WO 2006065590, WO 2006093801, WO 200702602, WO 2007039142, WO 2007039145, WO 2007076034, WO 2007088148, WO 2007092000, and WO2007095269); HCV NS4 Inhibitors (see WO 2005067900 and WO 2007070556); HCV NS5a Inhibitors (see US 2006276511, WO 2006035061, WO 2006100310, WO 2006120251, and WO 2006120252); Toll-like receptor agonists (see WO 2007093901); and other inhibitors (see WO 2000006529, WO 2003101993, WO 2004009020, WO 2004014313, WO 2004014852, and WO 2004035571); and compounds disclosed in U.S. patent application Ser. No. 12/053,015, filed Mar. 21, 2008 (US 2010/0016251) (the contents of which are incorporated by reference), interferon-α, interferon-β, pegylated interferon-α, ribavirin, levovirin, viramidine, another nucleoside HCV polymerase inhibitor, a HCV non-nucleoside polymerase inhibitor, a HCV protease inhibitor, a HCV helicase inhibitor or a HCV fusion inhibitor.

When any of compounds 4, $R_P$-4, or $S_P$-4 are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

Preparation

A seventh embodiment is directed to a process for preparing any one of compounds 4, $R_P$-4, or $S_P$-4, which comprises: a) reacting an isopropyl-alanate, A, a di-LG-phenylphosphate, B, 2'-deoxy-2'-fluoro-2'-C-methyluridine, 3, and a base to obtain a first mixture comprising at least one of $S_P$-4 and $R_P$-4

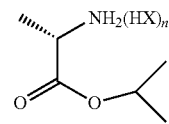

A

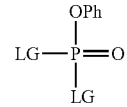

B

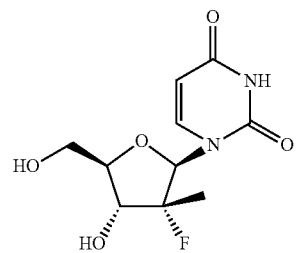

3 wherein X is a conjugate base of an acid, n is 0 or 1, and LG is a leaving group; b) reacting the first mixture with a protecting compound to obtain a second mixture comprising at least one of protected $S_P$-4 and protected $R_P$-4; and c) optionally subjecting the second mixture to crystallization, chromatography, or extraction in order to obtain 4, $S_P$-4, or $R_P$-4.

In a first aspect of the seventh embodiment, the isopropyl alanate is present as its hydrochloric acid salt, which is preferably, substantially anhydrous.

In a second aspect of the seventh embodiment, the base is N-methylimidazole.

In a third aspect of the seventh embodiment, the mole ratio of A-to-B-to-3 is about 1.6-to-1.3-to-1.

In a fourth aspect of the seventh embodiment, the protecting compound is tert-butyl dimethylsilyl chloride.

An eighth embodiment is directed to a process for preparing $S_P$-4 or $R_P$-4, which comprises: a) reacting an isopropyl-alanate, A, a di-LG-phenylphosphate, B, 2'-deoxy-2'-fluoro-2'-C-methyluridine, 3, and a base to obtain a first mixture comprising at least one of $S_P$-4 and $R_P$-4

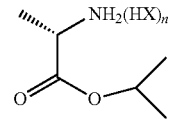

A

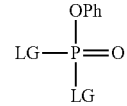

B

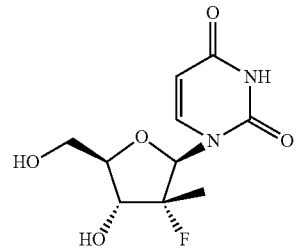

3 wherein X is a conjugate base of an acid, n is 0 or 1, and LG is a leaving group; and b) optionally subjecting the second mixture to crystallization, chromatography, or extraction in order to obtain purified $S_P$-4 or $R_P$-4.

A first aspect of the eighth embodiment for preparing $R_P$-4 additionally includes further purifying the second mixture or the purified $R_P$-4 by dissolving or suspending the second mixture or the purified $R_P$-4 mixture in a solvent; optionally followed by seeding with crystalline $R_P$-4; and adding sufficient anti-solvent to obtain crystalline $R_P$-4.

A second aspect of the eighth embodiment for preparing $S_P$-4 additionally includes further purifying the second mixture or the purified $S_P$-4 by d) dissolving or suspending the second mixture or the purified $S_P$-4 in a solvent followed by seeding with crystalline $S_P$-4 at about room temperature; collecting a first solid the majority of which comprises $S_P$-4; dissolving the first solid in a solvent at its reflux temperature; and cooling or adding an anti-solvent to obtain a second solid.

A third aspect of the eighth embodiment for the preparation of $S_P$-4, additionally includes further purifying $S_P$-4 by d) dissolving or suspending the second mixture or the purified $S_P$-4 mixture in a first solvent followed by adding an anti-solvent so as to obtain a first composition in which the residual solvent/anti-solvent is removed by decanting to obtain a residue; treating the residue with a solution containing the first solvent and anti-solvent to yield a second composition whereby upon reducing the pressure affords a first solid; dissolving or suspending the first solid using a second solvent so as to obtain a third composition; adding seed crystals of $S_P$-4 to the third composition; collecting a second solid; dissolving or suspending the second solid in a third solvent, optionally heated to the reflux temperature of the third solvent to obtain a fourth composition, and, if necessary, cooling the fourth composition to obtain a third solid comprising $S_P$-4 which is collected by filtration.

In a fourth aspect of the eighth embodiment for the preparation of $S_P$-4, $S_P$-4 is further purified by the second mixture or the purified $S_P$-4 by d) adding silica gel to the second mixture or the purified $S_P$-4 followed by solvent evaporation to afford a dry slurry; stirring the dry slurry in a first solvent/anti-solvent combination to obtain a first wet slurry; decanting the first solvent/anti-solvent combination from the first wet slurry to obtain a second wet slurry and a first composition; adding to the second wet slurry a second solvent/anti-solvent combination followed by stirring; decanting the second solvent/anti-solvent combination from the second wet slurry to obtain a third wet slurry and a second composition; optionally repeating steps g)-h) on the third wet slurry or additional wet slurries; evaporating the solvent from the second composition, and optionally any additional composition obtained from optional step i) to obtain a first solid; dissolving or suspending the first solid in a solution containing a third solvent and optionally a fourth solvent to obtain a third composition; optionally adding seed crystals of $S_P$-4 to the third composition; obtaining from the third composition a second solid comprising $S_P$-4; and optionally recrystallizing the second solid using a third solvent to obtain a third solid comprising $S_P$-4.

One of ordinary skill will appreciate that the compounds can be separated by traditional extraction, traditional crystallization or traditional chromatographic techniques. Traditional chromatographic techniques include, but are not limited to, chromatography on silica gel (using, e.g., 3-5% methanol in DCM or 4-6% isopropanol in DCM) to produce enhanced levels of one isomer (50-100%) and then crystallize it. Alternatively, one could use reversed phase chromatography (using, e.g., 1-30% acetonitrile-aqueous mobile phase). Furthermore the compounds can be isolated by supercritical fluid chromatography SFC with carbon dioxide as the main solvent and alcohols such as methanol as a modifier, preferably using the appropriate chiral media, such as, Daicel Chiralpack IA. Alternatively, SMB chromatography may be employed using the appropriate chiral media, such as, Daicel ChiralPack IA, using a mixture of solvents such as hexanes/isopropanol or single solvents such as ethyl acetate.

A ninth embodiment is directed to a process for preparing $S_P$-4, which comprises: a) reacting an isopropyl-alanyl-phosphoramidate with a 3'-O-protected or unprotected 3, and a basic reagent to obtain a composition comprising protected or unprotected $S_P$-4

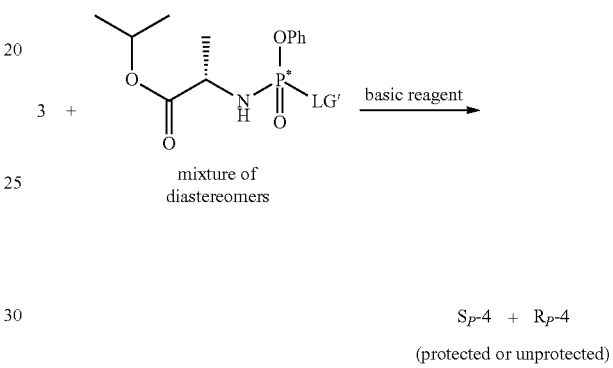

wherein the isopropyl-alanyl-phosphoramidate is comprised of a mixture of diastereomers represented by the following structures:

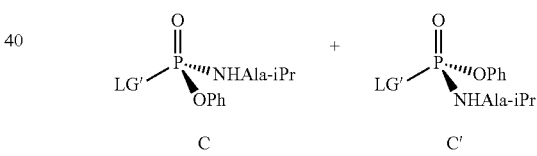

wherein the ratio of C:C' is about 1:1.

In a first aspect, the basic reagent is t-butylmagnesium chloride and the ratio of C:C' is greater than or equal to about 1:1.

In a second aspect, the basic reagent is t-butylmagnesium chloride and the ratio of C:C'; is greater than about 1:1.

In a third aspect, the basic reagent is t-butylmagnesium chloride and the ratio of C:C' is at least about 1.5:1, about 2.3:1, about 4:1, about 5.7:1, about 9:1, about 19:1, about 32.3:1, about 49:1, or about 99:1.

A fourth aspect the LG' is p-nitrophenoxide, the basic reagent is t-butylmagnesium chloride, and the ratio of C:C' is at least about 1.5:1, about 2.3:1, about 4:1, about 5.7:1, about 9:1, about 19:1, about 32.3:1, about 49:1, or about 99:1.

A fifth aspect for preparing $S_P$-4, comprises: a) reacting an isopropyl-alanyl-phosphoramidate (C) with a 3'-O-protected or unprotected 3, and a basic reagent to obtain a composition comprising protected or unprotected $S_P$-4

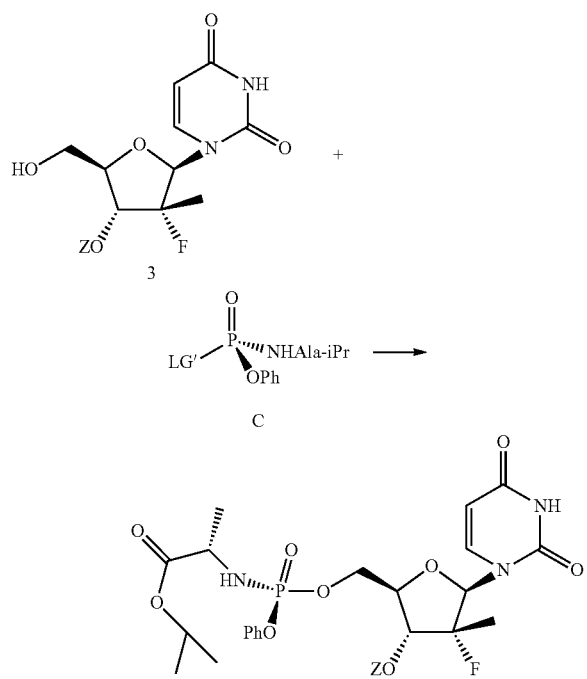

and subjecting the mixture to chromatography or crystallizing the mixture to obtain C. In an aspect of the ninth embodiment, the isopropyl alanate is present as its hydrochloric acid salt, which is preferably, substantially anhydrous.

A tenth embodiment is directed to a process for preparing $R_P$-4, which comprises: a) reacting an isopropyl-alanyl-phosphoramidate with a 3'-O-protected or unprotected 3, and a basic reagent to obtain a composition comprising protected or unprotected $R_P$-4

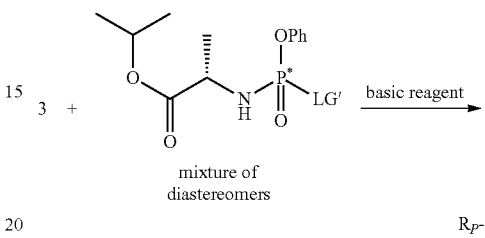

wherein Z is a protecting group or hydrogen; LG' is a leaving group; and b) optionally subjecting the obtained protected or unprotected $S_P$-4 to chromatography, extraction, or crystallization in order to obtain purified protected or unprotected $S_P$-4. In a sub-embodiment, LG' is tosylate, camphorsulfonate, or an aryloxide substituted with at least one electron withdrawing group; more preferably, LG' is selected from among p-nitrophenoxide, 2,4-dinitrophenoxide, and pentafluorophenoxide. In a further sub-embodiment, when $S_P$-4 is protected, i.e., Z is not hydrogen, the process of the ninth embodiment is further directed to deprotecting protected $S_P$-4. In a further sub-embodiment, the reaction is conducted in a polar aprotic solvent, such as, tetrahydrofuran or another etheral solvent either one being alone or in combination with each other or with a $C_2$ to $C_7$ nitrile, such as acetonitrile.

The process of the ninth embodiment further comprises 1) reacting (LG')P(O)(LG)$_2$, wherein LG, independent of LG', is a leaving group, with (i) isopropyl-alanate and a first base to obtain (LG')P(O)(LG)(NHAla-$^i$Pr) followed by reacting (LG')P(O)(LG)(NHAla-$^i$Pr) with phenol and a second base to obtain a mixture comprising C and C', (ii) phenol and a first base to obtain (LG')P(O)(LG)(OPh) followed by reacting (LG')P(O)(LG)(OPh) with isopropyl-alanate and a second base to obtain a mixture comprising C and C', or (iii) combining isopropyl-alanate, phenol, and at least one base to obtain a mixture comprising C and C'; or 2) reacting (PhO)P(O)(LG)$_2$, wherein LG', independent of LG, is a leaving group, with (i) isopropyl-alanate and a first base to obtain (PhO)P(O)(LG)(NHAla-$^i$Pr) followed by reacting (PhO)P(O)(LG)(NHAla-$^i$Pr) with a leaving group precursor and a second base to obtain a mixture comprising C and C',

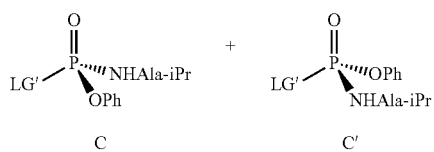

wherein the isopropyl-alanyl-phosphoramidate is comprised of a mixture of diastereomers represented by the following structures:

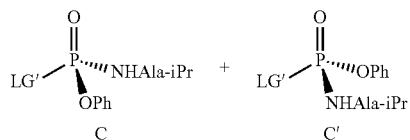

wherein the ratio of C':C is about 1:1.

In a first aspect, the basic reagent is t-butylmagnesium chloride and the ratio of C':C is greater than or equal to about 1:1.

In a second aspect, the basic reagent is t-butylmagnesium chloride and the ratio of C':C; is greater than about 1:1.

In a third aspect, the basic reagent is t-butylmagnesium chloride and the ratio of C':C is at least about 1.5:1, about 2.3:1, about 4:1, about 5.7:1, about 9:1, about 19:1, about 32.3:1, about 49:1, or about 99:1.

A fourth aspect the LG' is p-nitrophenoxide, the basic reagent is t-butylmagnesium chloride, and the ratio of C':C is at least about 1.5:1, about 2.3:1, about 4:1, about 5.7:1, about 9:1, about 19:1, about 32.3:1, about 49:1, or about 99:1.

A fifth aspect for preparing $R_P$-4, comprises: a) reacting an isopropyl-alanyl-phosphoramidate (C') with a 3'-O-protected or unprotected 3, and a basic reagent to obtain a composition comprising protected or unprotected $R_P$-4

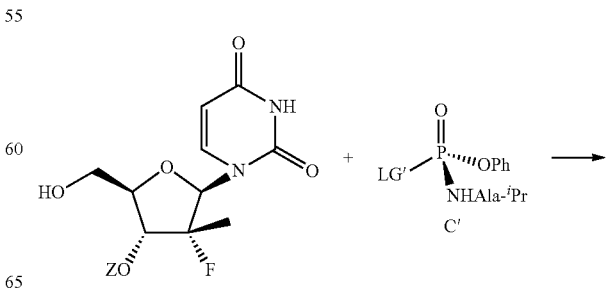

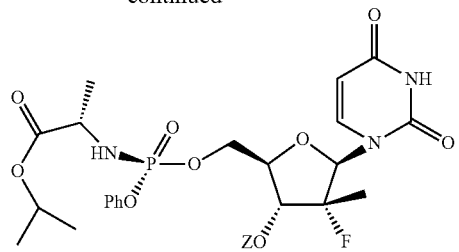

wherein Z is a protecting group or hydrogen; LG' is a leaving group; and b) optionally subjecting the obtained protected or unprotected $R_P$-4 to chromatography, extraction, or crystallization in order to obtain purified protected or unprotected $R_P$-4. In a sub-embodiment, LG' is tosylate, camphorsulfonate, or an aryloxide substituted with at least one electron withdrawing group; more preferably, LG' is selected from among p-nitrophenoxide, 2,4-dinitrophenoxide, and pentafluorophenoxide. In a further sub-embodiment, when $R_P$-4 is protected, i.e., Z is not hydrogen, the process of the ninth embodiment is further directed to deprotecting protected $R_P$-4. In a further sub-embodiment, the reaction is conducted in a polar aprotic solvent, such as, tetrahydrofuran or another etheral solvent either one being alone or in combination with each other or with a $C_2$ to $C_7$ nitrile, such as acetonitrile.

The process of the tenth embodiment further comprises 1) reacting (LG')P(O)(LG)$_2$, wherein LG, independent of LG', is a leaving group, with (i) isopropyl-alanate and a first base to obtain (LG')P(O)(LG)(NHAla-$^i$Pr) followed by reacting (LG')P(O)(LG)(NHAla-$^i$Pr) with phenol and a second base to obtain a mixture comprising C and C', (ii) phenol and a first base to obtain (LG')P(O)(LG)(OPh) followed by reacting (LG')P(O)(LG)(OPh) with isopropyl-alanate and a second base to obtain a mixture comprising C and C', or (iii) combining isopropyl-alanate, phenol, and at least one base to obtain a mixture comprising C and C'; or 2) reacting (PhO)P(O)(LG)$_2$, wherein LG', independent of LG, is a leaving group, with (i) isopropyl-alanate and a first base to obtain (PhO)P(O)(LG)(NHAla-$^i$Pr) followed by reacting (PhO)P(O)(LG)(NHAla-$^i$Pr) with a leaving group precursor and a second base to obtain a mixture comprising C and C',

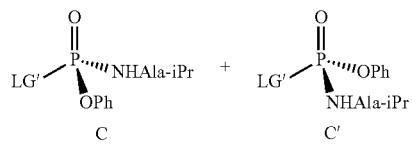

and subjecting the mixture to chromatography or crystallizing the mixture to obtain C'. In an aspect of the ninth embodiment, the isopropyl alanate is present as its hydrochloric acid salt, which is preferably, substantially anhydrous.

An eleventh embodiment is directed to a composition obtained by the processes recited in the seventh embodiment, the eighth embodiment, the ninth embodiment or the tenth embodiment as well as their respective aspects. An aspect of the eleventh embodiment is directed to a composition obtained by any one of the exemplified embodiments disclosed below. The so obtained composition can be crystalline, crystal-like, amorphous, or a combination thereof.

A twelfth embodiment is directed to a compound 3

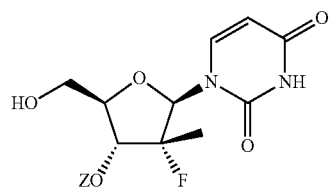

wherein Z is a protecting group or hydrogen; which is useful for the preparation of $R_P$-4 or $S_P$-4.

A first aspect of the twelfth embodiment is selected from among a compound having the following structure

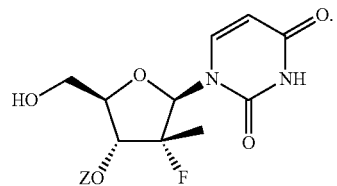

3a: Z = ——C(O)CH$_2$CH$_2$C(O)CH$_3$
3b: Z = ——C(O)OCH$_2$Ph
3c: Z = ——Si(Me)$_2^t$Bu
3d: Z = ——Si($^i$Pr)$_2$OSi($^i$Pr)$_2$OH

A thirteenth embodiment is directed to a compound, its salt, hydrate, solvate, or combination thereof, represented by the following structures

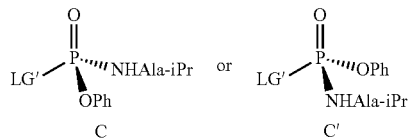

where LG' is a leaving group, which is useful for the preparation of $R_P$-4 or $S_P$-4.

In a first aspect of the thirteenth embodiment, LG' is tosylate, camphorsulfonate, an aryloxide, or an aryloxide substituted with at least one electron withdrawing group.

In a second aspect of the thirteenth embodiment, LG' is selected from among p-nitrophenoxide, 2,4-dinitrophenoxide, and pentafluorophenoxide.

A fourteenth embodiment is directed to an isotopically-labeled analog of $R_P$-4 or $S_P$-4. The term "isotopically-labeled" analog refers to an analog of $R_P$-4 or $S_P$-4 that is a "deuterated analog", a "$^{13}$C-labeled analog," or a "deuterated/$^{13}$-C-labeled analog." The term "deuterated analog" means a compound described herein, whereby a $^1$H-isotope, i.e., hydrogen (H), is substituted by a $^2$H-isotope, i.e., deuterium (D). Deuterium substitution can be partial or complete. Partial deuterium substitution means that at least one hydrogen is substituted by at least one deuterium. For instance, for $R_P$-4 or $S_P$-4, one of ordinary skill can contemplate at least the following partial deuterated analogs (where "d$_n$" represents n-number of deuterium atoms, such as, for an isopropyl group n=1-7, while for a phenyl group, n=1-5), as well as those depicted below.

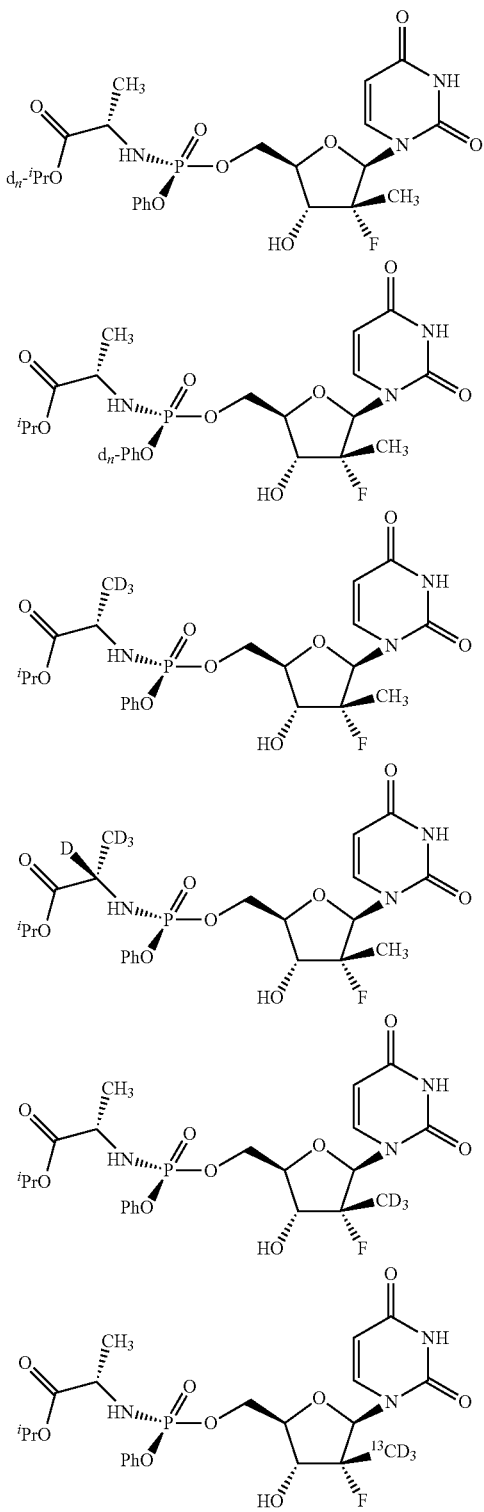

Although the methyl groups depicted above are shown as being completely deuterated, one will recognize that partial-deuterated variations are also possible, such as, —CDH$_2$ and —CD$_2$H. Isotopic labels on the furanose and base are also contemplated. Likewise, the terms "$^{13}$C-labeled analog" and "deuterated/$^{13}$-C-labeled analog" refers to a compound described herein, whereby carbon atom is enriched with a $^{13}$C-isotope meaning that the extent of enrichment exceeds the usual natural abundance of about 1.1%.

EXAMPLES

Not to be limited by way of example, the following examples serve to facilitate a better understanding of the disclosure.

Synthetic Aspects

In order to prepare the uridine nucleoside, one could take advantage of an advanced tribenzoylated cytidine intermediate in the synthesis of certain 3',5'-diacylated analogs of 3 (see below) already produced efficiently on a pilot plant scale (see WO 2006/031725 or US 2006/0122146, both of which are incorporated by reference in their entirety). The following method was found to be scalable and cost-efficient.

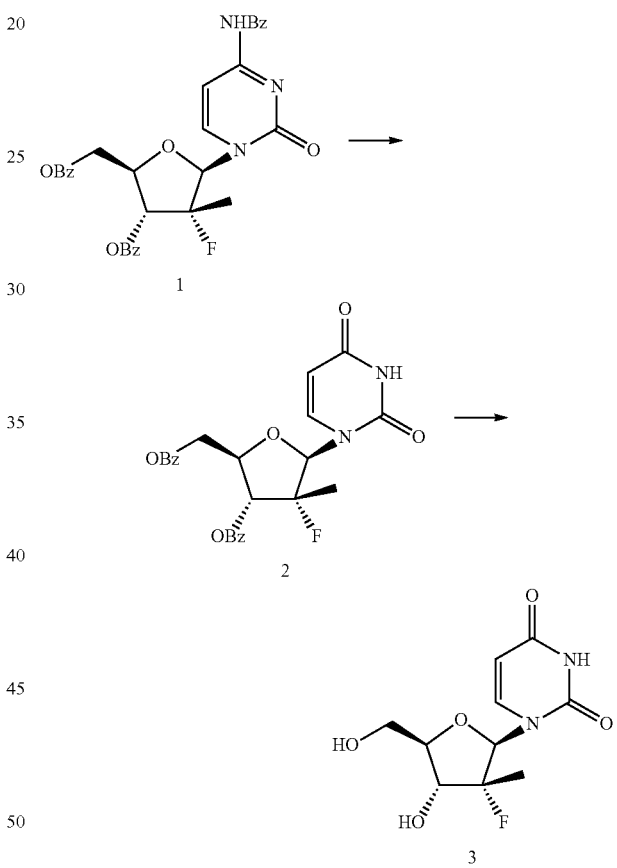

3',5'-O-dibenozyl-2'-deoxy-2'-fluoro-2'-C-methyl-N$^4$-benzoylcytidine (1) is obtained by a method disclosed in WO 2006/031725 and WO 2008/045419 both of which are hereby incorporated by reference in its entirety. 1 is treated with 70% aqueous acetic acid to form 3',5'-O-dibenozyl-2'-deoxy-2'-fluoro-2'-C-methyl-uridine (2). The benzoyl esters can be hydrolyzed by a number of methods as well, e.g., alkoxides in alcoholic solvent, such as sodium methoxide in methanol, potassium carbonate in methanol, or ethanol analogs, alkylamines such as methylamine in methanol, butylamine etc. Methanolic ammonia was chosen for the larger scale work. The uridine product (3) can be purified by crystallization to afford a 70% yield from the tribenzoylated cytidine (1).

Numerous literature procedures detail different routes and conditions to make phosphoramidates using several fold equivalents of reagents. See, for example, McGuigan et al. *J. Med. Chem.* 2005, 48, 3504-3515 and McGuigan et al. *J. Med. Chem.* 2006, 49, 7215. For process scale work, there is only one presently known example, which is disclosed in Lehsten et al., *Org. Process Res. Dev.* 2002, 6, 819-822 ("Lehsten"). In this reference, the authors introduce the concept of a "one-pot procedure" in which an amino acid hydrochloride salt and phenyl dichlorophosphate are reacted together with N-methylimidazole in dichloromethane. Later the nucleoside is added to form the desired 5'-O-phosphoramidate product, which in the present case would yield a compound represented by formula 4. Unfortunately, the Lehsten procedure suffered from drawbacks. For example, the Lehsten procedure utilized a far larger excess of reagents than was necessary which added to the cost and difficulty of chromatographic purification. Furthermore, Lehsten suggested that one could control the reaction selectivity on the 5'-hydroxyl over the 3'-hydroxyl compared to a literature reference through using lower temperatures and slow addition of the nucleoside.

4

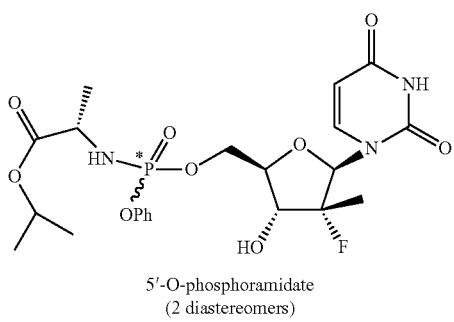

5'-O-phosphoramidate
(2 diastereomers)

5

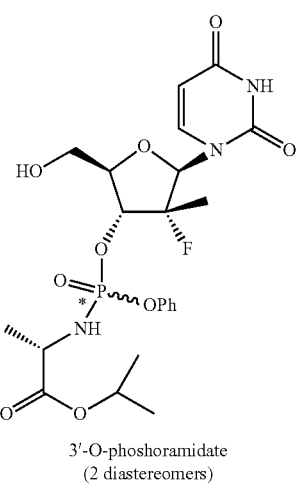

3'-O-phoshoramidate
(2 diastereomers)

6

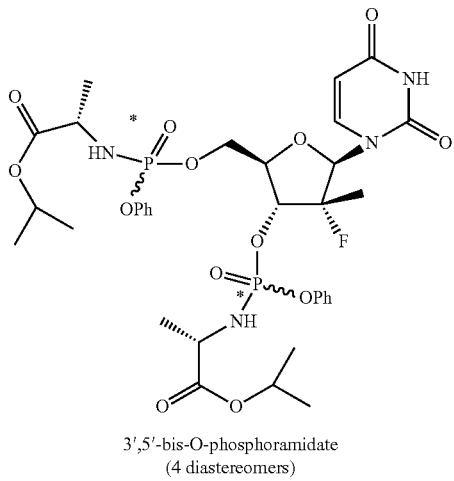

3',5'-bis-O-phosphoramidate
(4 diastereomers)

Using the Lehsten procedure for the compounds disclosed herein provided for about 1-5% of mono-substituted 3'-O-phosphoramidate diastereomers (5) and about 10-30% of the bis-substituted product (6). As the polarity of the 3'-diastereomers was very similar to the desired 5'-diastereomers (4), chromatographic separation was very challenging. Scaling up the process was nearly impossible without discarding a substantial portion of the less polar 5'-diastereomers (4) or accepting a higher level of contamination of the 3'-diastereomers (5). In an initial 50 g scale-up, the resultant product contained a 3'-diastereomer (5) contamination of about 3%, which co-eluted with the less polar of the 5'-diastereromer (4).

Disclosed herein are reaction conditions which use lesser amounts of reagents and a method to selectively remove the impurity 3'-O-phosphoramidate diastereomers (5) with an easier chromatographic separation thereby affording the desired 5'-β-phosphoramidate diastereomers in much higher purity (4).

For the reagent stoichiometry, a study was made in which the stoichiometry of the reagents was systematically changed and the results were monitored by phosphorus NMR of the crude reaction as Lehsten had reported. In the more successful runs, the isolated yield and purity of the desired product were compared. It was observed that the primary 5'-hydroxyl reacts at a faster rate than the secondary 3'-hydroxyl. This creates a competing situation between the reaction progress of consuming all the starting nucleoside and converting 5'- and 3'-monosubstituted products (4 and 5) to the 5',3'-bis substituted products (6). The 3'-monosubstituted product converts to the bis product at a faster rate than the 5'-monosubstituted product, so it is possible to reduce the 3'-diastereomer contamination level by pushing the reaction more to the bis-substituted products. However, with an effective way to remove the 3'-diastereomers, the reaction can be optimized to produce more of the desired 5'-diastereomer without having to sacrifice as much of the 5'-diastereomer being converted to the bis-substituted (6). It was also observed that the amino acid hydrochloride is very hygroscopic. As any water present would consume an equivalent amount of the phenyl dichlorophosphate reagent, care must be taken to keep the amino acid substantially anhydrous or it should be made substantially anhydrous prior to use. In short, Lehsten had reported that the optimum ratio of amino acid to phenyl dichlorophosphate to nucleoside was 3.5:

2.5:1 respectively. It was found that the optimum ratio of amino acid to phenyl dichlorophosphate to nucleoside of about 1.6 to about 1.3 to about 1 is optimal under conditions in which the 3'-diastereomer can be efficiently removed and when the amino acid hydrochloride is substantially anhydrous. By using a smaller amount of the reagents, a cost savings is realized coupled with a simplification of the chromatographic separation of the desired product from reagent by-products and from the reduced level of bis diastereomers. In one alternative procedure, a 3'-hydroxy-blocked derivative of 3 was prepared using a t-butyldimethylsilyl blocking group in two steps. This was then converted to its 5'-phosphoramidate derivative. The desire being that the silyl group could then be removed and there would be no 3' isomers (5) or 3',5'-bis phosphoramidates (6). A similar approach was demonstrated by Borch and Fries (U.S. Pat. No. 5,233,031) in a low overall yield on an alkyl phosphoramidate.

Another alternative approach was to use the direct synthesis and then use chemistry to help differentiate the 3'-diastereomer impurities 5 from the desired 5'-diastereomers 4 to help the separation. A group was desired that would selectively react with the free primary hydroxyl of the 3'-O-phosphoramidate impurity 5 over the free secondary hydroxyl of the desired 5'-O-phosphoramidate 4. It was also desired that the blocking group significantly change the polarity of the resulting 5'-O-blocked 3'-O-phosphoramidate product from the desired 5'-O-phosphoramidate 4. There would be no extra step needed to remove the blocking group as the desired 5'-diastereomers 4 would not be changed. The chemically altered 3'-diastereomers would then allow easier chromatographic separation or separation by special scavenging supports or by extractions.

Specifically, the blocking group tert-butyldimethylsilyl (tBDMS) met these criteria and was the first one to be demonstrated and subsequently used on a multi-kilogram scale. Under certain conditions such as in pyridine as solvent and base, the tBDMS group reacts with high selectivly at the primary hydroxyl position over the 3' secondary hydroxyl position. The phosphoramidate reaction uses N-methylimidazole (NMI) as a base. In the presence of NMI, the silylation is less selective. Preferably, the amount of NMI should be reduced. This can be accomplished easily after the phosphoramidate reaction by washing the reaction solution with 1 N hydrochloric acid. The NMI and the remaining starting nucleoside are removed, leaving a crude mixture of mono and bis substituted products and reagent by-products. This is then dissolved in pyridine and treated with tert-butyldimethylsilyl chloride. The 3'-monosubstituted product 5 is converted in a few hours or less to the 5'-O-tBDMS-3'-O-phosphoramidate 7. The reaction progress can be monitored by HPLC. The polarity of this silylated product 7 is less than the bis-phosphoramidate 6 and is readily removed by chromatography. Using this method, it was possible to reduce the level of 3'-monophosphoramidate 5 to less than 0.1% of the 5'-product 4 compared to 1-3% without the silyl treatment. Similarly, treatment with dimethoxytriphenylmethyl chloride (DMT-Cl) under the same conditions worked just as well. It was also easier to identify the DMT reaction product by TLC as DMT containing molecules stain bright orange on heating or exposure to acid. One can also envision many other blocking groups, as noted above.

Both the reaction conditions and the scavenging of the 3'-impurity are general methods and could be applied to most nucleoside phosphoramidates with a free 3' hydroxyl. The phosphoramidate moiety could be any combination of amino acid ester and aromatic alcohol. The nucleoside moiety could be any nucleoside in which a 5' phosphoramidate would lead to a 5'-monophosphate and could be further metabolized to the 5'-triphosphate form.

The following scheme is the main reaction scheme illustrated for making isopropyl L-alanate phenyl phosphoramidate of 2'-deoxy-2'-fluoro-2'-C-methyluridine with the major product as the desired 5'-O-phosphoramidate (4, two diastereomers) and the minor product as the 3'-O-phosphoramidate (5, two diastereomers) and the 3',5'-bis-O-phosphoramidate (6, four diastereomers). The reagents are added in the stoichiometric ratios as described in the method of preparation section. The reaction is allowed to proceed until about 5% of the starting material remains as judged by UV visualization on thin layer chromatography (TLC). Also UPLC/MS showed approximately 10% of the 3',5' bis-phosphoramidate 6 had formed compared to the desired 5'-product. After quenching and an acidic aqueous workup, the crude residue from the organic layer was prepared for the silylation. Under the described reaction conditions, the silyl group preferentially reacted with the free 5'-hydroxyl of the 3'-O-phosphoramidate to form 7. The reaction was continued until the 3'-O-phosphoramidate was no longer detectable by UPLC/MS.

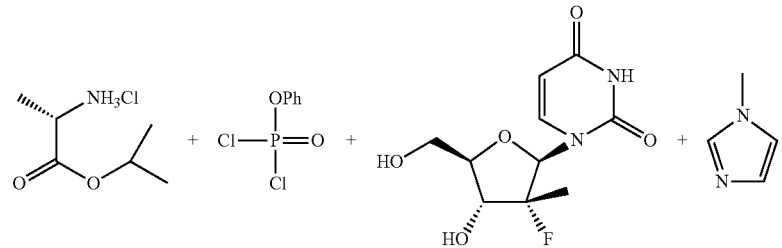

3

↓

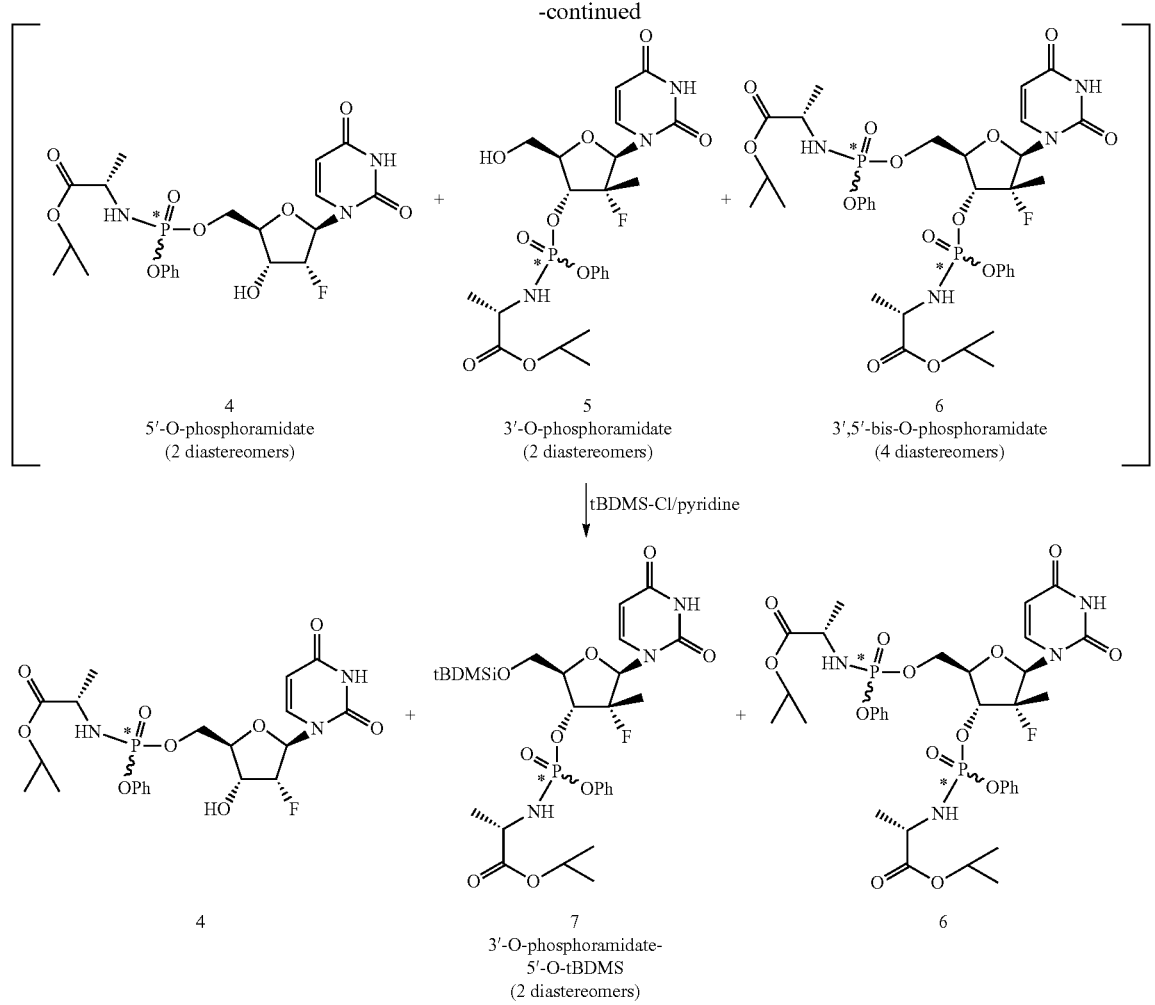

4
5'-O-phosphoramidate
(2 diastereomers)

5
3'-O-phosphoramidate
(2 diastereomers)

6
3',5'-bis-O-phosphoramidate
(4 diastereomers)

4

7
3'-O-phosphoramidate-
5'-O-tBDMS
(2 diastereomers)

6

After working up the silylation reaction, the desired product is subjected to chromatography on silica gel and is eluted with a gradient of methanol in dichloromethane (1-4%). The desired 5'-monophosphoramidate 4 elutes last.

Method of Preparation

Example 1

Preparation of 2'-deoxy-2'-fluoro-2'-C-methyluridine (3)

In a 10 L flask, was added 3',5'-O-dibenozyl-2'-deoxy-2'-fluoro-2'-C-methyl-N4-benzoylcytidine (500 g, 0.874 mol) and 70% aqueous acetic acid (7.5 L). The solution was heated to reflux (110° C.) for 20 h. TLC indicated a complete reaction (Rf 0.6 in 5% methanol in dichloromethane (DCM)). The mixture was cooled to ambient temperature and diluted with water (2 L). After stirring for 2 h, the resulting precipitate was collected by filtration and the solid was rinsed with water (5 L) and dried in the atmosphere at ambient temperature for 12 h to afford 360 g (88%). This dibenzoyluridine intermediate was used directly in the next step by adding it all to freshly prepared methanolic ammonia (5.4 L, ca 25%) at 0° C. This temperature was maintained for 3 h and then allowed to warm to 15° C. for 24 h. TLC indicated a complete reaction ($R_f$ 0.4 in 10% methanol in DCM). The reaction mixture was filtered through a Celite bed and concentrated under reduced pressure to give the crude product (216 g). The crude product was stirred with ethyl acetate (325 mL) for 3 h at ambient temperature. The resulting solid was collected by filtration and washed with ethyl acetate (216 mL). The solid was dried under vacuum at ambient temperature for 4 h to afford 160 g (78%) of the desired product in 98.7% HPLC purity. $^1$H-NMR (DMSO-$d_6$) δ 11.44 (br s, 1H, NH), 7.95 (d, 1H, C-6H), 5.97 (d, 1H, C-1'H), 5.64 (d, 1H, C-5H), 3.84-3.77 (m, 3H, C-5'-Ha, C-3'H. C-4'H), 3.63-3.60 (m, 1H, C5'-Hb), 1.23 (d, 3H, C-2'-CH$_3$). ES-MS M-1 259.

Example 2

Preparation of (S)-2-{[(1R,4R,5R)-5-(2,4-Dioxo-3,4-dihydro-2H-pyrimidin-1-yl)-4-(R)-fluoro-3-hydroxy-4-methyl-tetrahydro-furan-2-ylmethoxy]-phenoxy-phosphorylamino}-propionic acid isopropyl ester (4)

Synonym: 5'-O-(Isopropyl-L-alanate, phenyl phosphoramidyl)-2'-deoxy-2'-fluoro-2'-C-methyl-uridine diastereomeric mixture.

A 5 L 3-necked flask was fitted with a mechanical stirrer, brine ice bath, internal thermometer, and a nitrogen atmosphere. The flask was charged with L-alanine isopropyl ester hydrochloride (82.0 g, 0.490 moles) and anhydrous dichloromethane (0.80 L). While this was stirring, phenyl dichlorophosphate (85.0 g, 0.40 moles) was added in one lot and stirred. While maintaining the internal temperature between −5 to 5° C., a solution of N-methylimidazole (NMI, 250 g, 3.07 moles) in dichloromethane (250 mL) was added over a period of a half hour. The solution was allowed to stir for 1 h in this temperature range. 2'-Deoxy-2'-fluoro-2'-C-methyl-uridine (3, 80.0 g, 0.307 moles) was added at 0° C. in one portion and then the reaction flask was allowed to warm up slowly in the brine bath. At 1 h, the internal temperature was up to −2° C. TLC (5% Methanol in DCM) at 1 h showed that more than 50% of nucleoside was consumed. The bath was removed and the reaction flask reached ambient temperature over 1 h more. TLC after 3 h and at 5 h total showed 95% of the starting nucleoside was consumed. The reaction mixture was quenched by adding methanol (100 mL) and stirring the reaction for 5 minutes.

The reaction mixture was washed with 1N HCl (2×500 mL) followed by saturated sodium bicarbonate solution (2×500 mL). The separated organic layer was dried over anhydrous sodium sulfate (50 g) and filtered. The solution was evaporated under reduced pressure and then under high vacuum to dryness to give the crude product as a viscous oil (170 g). NMRs of the crude product ($^{31}$P and $^1$H) were taken. The $^{31}$P-NMR indicated about 1% of the total phosphorus integration was due to the presence of the 3' isomer 5.

To the crude product was added anhydrous pyridine (1700 mL). The solvent was evaporated under reduced pressure and then under high vacuum in order to reduce the water content of the crude mixture through co-evaporation. The resulting oil was re-dissolved in anhydrous pyridine (500 ml) and then was added excess t-butyldimethylsilyl chloride (9.0 g, 60 mM). The reaction was stirred at ambient temperature. Reaction progress was monitored by UPLC/MS. After 3 hours, the 3' impurity 5 could no longer be detected and the reaction was quenched by the addition of methanol (50 mL).

The reaction was evaporated under reduced pressure to an oil. The residue was dissolved in ethyl acetate (1.5 L) and washed with 1N HCl (2×500 mL), followed by saturated sodium bicarbonate solution (2×500 mL). The organic layer was dried over anhydrous sodium sulfate (50 g), filtered and evaporated under reduced pressure to give the crude product as a pale yellow oil.

The crude oil was diluted with the same volume of dichloromethane and loaded onto a 2.5 Kg silica gel cartridge in a radial compression module at 100 psi of air pressure. Using a gradient pump at 60 psi and a flow rate of 400 mL/min, the cartridge was washed with methylene chloride (4 L) followed by a gradient 1-4% methanol in methylene chloride (48 L). Most of the major impurities (di-(isopropylalanyl)phenyl phosphate, 3',5'-bis phosphoramidate (6), 3'-phosphoramidate-5'-TBDMS adduct (7)) eluted with ~3% gradient. The desired product eluted between 3 and 4% methanol. The product containing fractions were sorted into two lots. The first contained small amounts of upper impurities and the latter was pure product. The first set of fractions contained small amounts of less polar impurities (upper impurities) such as the 3',5'-bis phosphoramidate and the di-alanylphenyl phosphate and a mostly the Rp diastereomer and required a second column purification. (The relative terminology, upper vs. lower refers to the elution on normal-phase silica-gel chromatography, where the "upper isomer" means the first eluting isomer.) The second set of fractions did not have a significant amount of impurities—just the remaining $R_P$ and mostly the $S_P$ diasterereomers. It was later recombined with the twice-columned fractions. The solvent was evaporated under reduced pressure and the resulting white foam was further dried (0.20 mmHg) for 1 h to give 42 g of the impure lot (4:1 upper vs lower isomer based of $^{31}$P-NMR) and 38 g of the pure lot (1:3 upper vs lower isomer). The impure lot was recolumned in a similar manner to give 3.8 g of 97% pure upper isomer (fraction set aside) and 36 g of pure product in a 4:1 ratio. The two main lots were dissolved in DCM, combined, evaporated under reduced pressure and dried (50° C., 0.2 mmHg, 24 h) to get 74 g (45.7%) of pure product 4 with a diastereomeric ratio of 48:51, as a white foam, mp about 75-85° C.

In order to produce an amorphous solid of the diastereomeric mixture, 74 g of the white foam was stirred in with t-butyl methyl ether (750 mL) resulting in a partial solution and a gummy solid residue. While stirring, heptanes (750 mL) was added slowly and the suspension was mechanically stirred for 1 hour until most of the gum was converted to a white solid. The solid was scraped up with a spatula and the resulting slurry was filtered. The solid was washed with heptanes (4×50 mL) and dried under vacuum (50° C., 0.2 mmHg, 24 h) to give a white, amorphous powder (64 g) with a broad melting range of ca 70-80° C. $^1$H and $^{31}$P NMR conformed to structure and HPLC showed a purity of 99.8% with a diastereomeric ratio of 46:54 (also confirmed by $^{31}$P NMR).

Alternative method to make solid mixture of 4. After chromatography, the residue was co-evaporated with dichloromethane twice (5 mL/g) and dried for 24 h at 35-40° C. at 35-45 mTorr. The foam residue was sieved through a 250 micron screen and further dried under the same conditions until the residual dichloromethane fell below 400 ppm as measured by headspace GC. The resulting fine off-white to white amorphous powder has a glass transition temperature range of 53.7 to 63.5° C.

Characterization of the mixture of isomers (4): $^1$H-NMR (CDCl$_3$) δ 10.05 (br s, 1H, NH, $S_P$), 10.00 (br s, 1H, NH, $R_P$), 7.49 (d, 1H, C6-H, $S_P$), 7.36 (m, 5H, C6-H, $R_P$, aromatic), 7.23-7.14 (m, 6H, $R_P/S_P$, aromatic), 6.18 (br d, 2H, C1'-H, $R_P/S_P$), 5.63 (d, 1H, C5-H, $S_P$), 5.58 (d, 1H, C5-H, $R_P$), 5.01 (m, 2H, CH—(CH$_3$)$_2$, $R_P/S_P$), 4.46-4.33 (m, 8H, C-5'-H$_2$, ala-NH, C3'-OH, $R_P/S_P$), 4.12 (m, 2H, ala-CH—CH$_3$, $R_P/S_P$), 4.01-3.85 (m, 4H, C3'-H, C4'-H, $R_P/S_P$), 1.39-1.22 (m, 12H, all CH$_3$, $R_P/S_P$).

$^{31}$P-NMR (CDCl$_3$) δ 3.60 ($R_P$), 3.20 Sp relative to triphenylphosphate at −17.80 ppm. ES-MS M+1 530.2. Elemental Analysis: Calculated % (including 0.29% water as found by Karl Fisher analysis) C, 49.75; H, 5.54; N, 7.90; F, 3.58; P, 5.84. Found %: C, 49.50; H, 5.44; N, 7.85; F, 3.62; P, 6.05.

Discussion on Separation of Isomers

Compound 4 due to the chirality at phosphorus is comprised of two diastereomers, which are designated as $S_P$-4 and $R_P$-4. The stereochemical assignment was made based on single crystal X-ray analysis of $S_P$-4. Both $R_P$-4 and $S_P$-4 gave crystalline product.

The procedures for crystallization are outlined below.

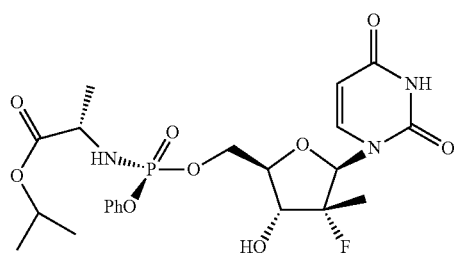

S$_P$-4

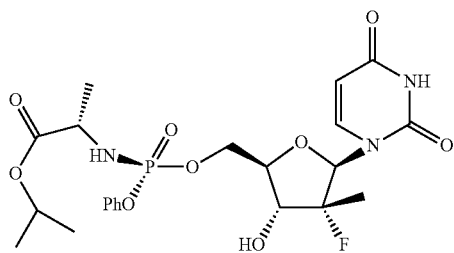

R$_P$-4

Example 3

Crystallization of the R$_P$-4 isomer. The chromatographed fraction of containing the first eluting, less polar R$_P$-4 isomer (3.8 g, 97% pure) was dissolved in isopropanol (36 g) and diluted with heptanes until cloudy (72 g). The solution was seeded and stirred at ambient temperature for 5 h. The resulting solid was collected by vacuum filtration, washed with heptanes (2×20 mL) and dried (50° C., 0.2 mm, 24 h) to 2.3 g of very small white needles mp 136.2-137.8° C. HPLC purity of the resultant material was found to be 99.02%.

R$_P$-4: $^1$H-NMR (CDCl$_3$) δ 9.10 (br s, 1H, NH), 7.36 (m, 2H, o-aromatic), 7.26-7.16 (m, 4H, C6-H, m,p-aromatic), 6.16 (br d, 1H, C1'-H), 5.58 (d, 1H, C5'-H), 5.01 (sept, 1H, CH—(CH$_3$)$_2$), 4.52-4.47 (m, 2H, C-5'-H$_2$), 4.10 (d, 1H, C3'-H), 4.02-3.76 (m, 4H, ala-NH, C3'-OH, C4'-H, ala-CH—CH$_3$), 1.37-1.20 (m, 12H, all CH$_3$).

Example 4

Preparation and Crystallization of S$_P$-4

Method 1: Direct precipitation from crude 4: To a stirred solution of L-alanine isopropyl ester hydrochloride (10.5 g, 61.5 mmol, azeotropically dried, two times, with 50 mL of toluene each time) in dichloromethane (100 mL) was added phenydichlorophosphate (7.5 mL, 50 mmol) at room temperature. The mixture was cooled to −10° C. and then was added a solution of NMI (30.5 mL, 384.3 mmol) in 30 mL of dichloromethane over a period of 30 min. After completion of the addition, the mixture was stirred between −10 and −15° C. for 1 h. To the above mixture was added 2'-deoxy-2'-fluoro-2'-C-methyluridine (3) (10 g, 38.4 mmol) in one lot and the mixture was stirred below −10° C. for 3 h and then slowly allowed to warm to 20° C. (6 h). The mixture was stirred at this temperature over night (15 h) and then quenched with 10 mL of methanol. The solvent was evaporated and the residue was re-dissolved in EtOAc (200 mL). The EtOAc layer was washed with water (100 mL), 1N HCl (3×75 mL), 2% aqueous NaHCO$_3$ solution (50 mL) and brine (50 mL). The organic layer was dried over Na$_2$SO$_4$, filtered and concentrated. The residue was dried under high vacuum for 2 h to give white foam (22 g).

The above foam was dissolved in 33 mL of DCM and then was added 65 mL of IPE (isopropyl ether) to give a saturated solution. The solution was filtered though a small pad of Celite and the filtrate was stirred with S$_P$-4 seeds for 72 h at ambient temperature (about 22° C.—note that cooling the suspension to 0° C. led to oiling out the crude product). The white solid was filtered, washed with IPE (20 mL) and dried to give 4.58 g (~85:15 mixture of S$_P$-4:R$_P$-4 respectively as determined by $^{31}$P NMR) of a white powder. The above solid was suspended in 23 mL of DCM and then refluxed for 3 h. The mixture was cooled to room temperature and stirred for 15 h. The white solid was filtered, washed with 4.5 mL of cold DCM and dried under high vacuum at 45° C. to give pure S$_P$-4, mp 93.9-104.7° C., HPLC purity 99.74% (3.11 g, 15.2% from the uridine nucleoside).

S$_P$-4 $^1$H-NMR (CDCl$_3$) δ 8.63 (br s, 1H, NH), 7.47 (d, 1H, C6-H), 7.30 (m, 2H, o-aromatic), 7.26-7.18 (m, 3H, m,p-aromatic), 6.18 (br d, 1H, C1'-H), 5.70 (d, 1H, C5-H), 5.02 (sept, CH—(CH$_3$)$_2$), 4.53 (m, 2H, C-5'-H$_2$), 4.11 (d, 1H, C3'-H), 3.97 (m, 3H, C3'-OH, C4'-H, ala-CH—CH$_3$), 3.77 (br s, 1H, ala-NH), 1.39 (d, 3H, C2'-CH$_3$), 1.37 (d, 3H, ala-CH$_3$), 1.24 (d, 6H, CH—(CH$_3$)$_2$).

Method 2: Oiling out from crude 4: To a stirred solution of L-alanine isopropyl ester hydrochloride (20.6 g, 123 mmol, azeotropically dried, two times, with 75 mL of toluene each time) in dichloromethane (200 mL) was added phenydichlorophosphate (14.9 mL, 100 mmol) at room temperature. The mixture was cooled to −10° C. and then was added a solution of NMI (61.3 mL, 769 mmol) in 60 mL of dichloromethane over a period of 30 min. After completion of the addition, the mixture was stirred between −10° C. and −15° C. for 1 h. To the above mixture was added 2'-deoxy-2'-fluoro-2'-C-methyluridine (3) (20 g, 76.9 mmol) in one lot and the mixture was stirred below −10° C. for 3 h and then slowly allowed to warm to 20° C. (6 h). The mixture was stirred at this temperature over night (15 h) and then quenched with 10 mL of methanol. The solvent was evaporated and the residue was re-dissolved in EtOAc (400 mL). The EtOAc layer was washed with water (200 mL), 1N HCl (3×100 mL), 2% aqueous NaHCO$_3$ solution (100 mL) and brine (50 mL). The organic layer was dried over Na$_2$SO$_4$, filtered and concentrated. The residue was dried under high vacuum for 2 h to give white foam (43 g). The above foam was dissolved in 86 mL of EtOAc in a two neck round bottom flask equipped with a mechanical stirrer. While stirring, 100 mL of heptane was added slowly and the suspension was stirred for 1 h. The top layer was decanted and the residue was again stirred with 50 mL of 2:3 EtOAc/heptane solutions for 10 min and then decanted. The residue was dried under high vacuum to give white foam (31 g).

The above foam was dissolved in 46 mL of DCM and then was added 95 mL of IPE to give a saturated solution. The solution was filtered though a small pad of Celite and the filtrate was stirred with S$_P$-4 seeds for 72 h at ambient temperature. The white solid was filtered, washed with IPE (30 mL) and dried to give 7.33 g (~85:15 mixture of S$_P$-4:R$_P$-4 respectively as determined by $^{31}$P NMR) of white powder. The above solid was suspended in 36 mL of DCM and then refluxed for 3 h. The mixture was cooled to room temperature and stirred for 15 h. The white solid was filtered, washed with 7.5 mL of cold DCM and dried under high vacuum at 45° C. to give >99% pure S$_P$-4, (4.78 g, 11.6% from the uridine nucleoside).

Method 3: Silica gel loading of crude 4: 5.0 g of crude 4 was produced as in the same manner as the mixture of diastereomers just before the column chromatography step starting with approximately 2.5 g of 2'-deoxy-2'-fluoro-2'-C-methyluridine (3). The crude was dissolved in 10 mL of DCM and 10 g of silica gel was added to the solution. The solvent was evaporated to give dry slurry. The slurry was stirred with 40 mL of 50% EtOAc/hexanes for 15 min and then filtered. The silica gel was washed with additional 10 mL of 50% EtOAc/hexanes. The silica gel was then washed with 15% MeOH/DCM (100 mL) and collected separately. The solvent was evaporated and dried under high vacuum to give 4.0 g of residue (foam). The residue was dissolved in DCM (6 mL) and then was added ~9 mL of IPE to make a saturated solution. The mixture was then gently stirred overnight with $S_P$-4 seeds at ambient temperature. The white solid was filtered and washed with IPE (5 mL) to give 1.28 g of product. $^{31}$P NMR revealed that the above product contains 77:23 mixture of $S_P$-4: $R_P$-4 respectively. This was recrystallized from 20 mL of DCM to obtain 0.75 g of >99% pure $S_P$-4 (about 12% from the uridine nucleoside). This preparation of $S_P$-4 does not require the silylation step as done for the mixture, so the entire reaction procedure is shown above. Aspects of single crystalline and polymorphic forms of $S_P$-4 are presented below.

Method 4: 40.0 g of 1:1 mixture of 4 was dissolved in 90 mL of dichloromethane. Diisopropylether (70 mL) was added to the above solution to give a saturated solution. (The quantity of diisopropyl ether may vary based on the purity of the product.) The solution was seeded with pure $S_P$-4 (>99%) and the mixture was gently stirred with a stir bar at room temperature for 20 h (formation of solid was observed after 2 h). The solid was filtered, washed with 40 mL of the mixture of diisopropylether/dichloromethane (1:1) and dried to give white solid (16.6 g, 89.35% pure $S_P$-4 by NMR). This solid was suspended in 83 mL dichloromethane and refluxed for 3 h. The suspension was cooled to room temperature and stirred over night. The solid was filtered and washed with 10 mL of cold DCM. The solid was dried under vacuum to give $S_P$-4 (13.1 g, 99.48% pure by HPLC). 11 g of this solid was redissolved in 330 mL of DCM under hot conditions. The solution was cooled to room temperature and left at this temperature over night. The crystalline product was filtered and dried to give 10.5 g of $S_P$-4 (99.74% by HPLC).

Compounds $S_P$-4 and $R_P$-4 may alternatively be prepared, in accordance with the ninth or tenth embodiment, by reacting nucleoside (protected or unprotected) 3 with an isopropyl-alanyl-phosphoramidate (mixture of C and C', C or C'), as shown in the following equation.

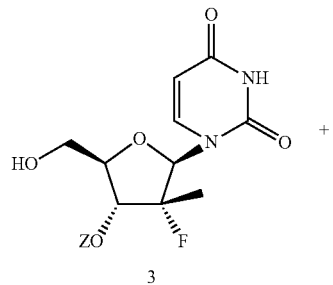

3

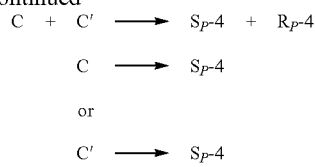

C + C' ⟶ $S_P$-4 + $R_P$-4

C ⟶ $S_P$-4 or

C' ⟶ $S_P$-4

P. D. Howes et al. *Nucleosides, Nucleotides & Nucleic Acids* 2003, Vol. 22, Nos. 5-8, pp. 687-689 ("Howes") discloses 2'- and 5'-phosphoramidates obtained by a reaction with t-butylmagnesium chloride. There, Howes discloses that when a 3'-deoxy-cytidine nucleoside is reacted with (S)-2-[chloro-phenoxy-phosphorylamino]propionic acid methyl ester in the presence of 1.2 equivalents of t-butyl-magnesium chloride, selective phosphorylation on the 2'-position occurred, but that with an additional equivalent of t-butylmagnesium chloride selective phosphorylation on the 5'-position occurred. This disclosure should be contrasted to that which is disclosed in Howes' Scheme 1.

Example 5-1

Preparation of (S)-2-[(4-nitro-phenoxy)-phenoxy-phosphorylamino]propionic acid isopropyl ester

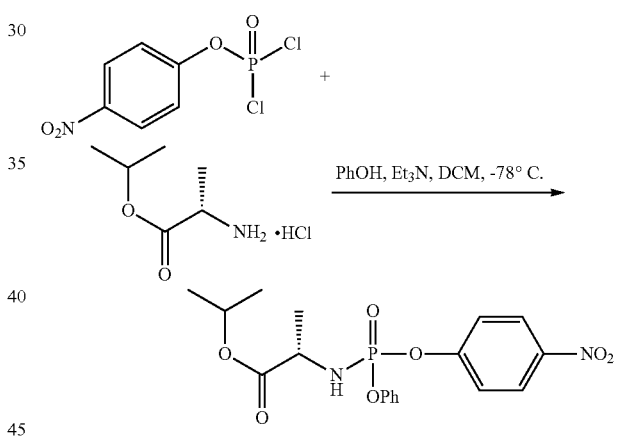

To a stirred solution of 4-nitrophenyl phosphorodichloridate 12.8 g, 50 mmol) in dichloromethane (100 mL) was added a solution of phenol and triethylamine (7.7 mL, 55 mmol) in dichloromethane (100 mL) at −78° C. over a period of 20 min. The mixture was stirred at this temperature for 30 min and then transferred to another round bottom flask containing L-alanine isopropyl ester hydrochloride (8.38 g, 50 mmol) in dichloromethane (100 mL) at 0° C. To the mixture was added second portion of triethylamine (14.6 mL, 105 mmol) over a period of 15 min. The mixture was stirred at 0° C. for 1 h and then the solvent was evaporated. The residue was triturated with ethyl acetate (150 mL) and the white solid was filtered off. The filtrate was concentrated under reduced pressure to give pale yellow oil. The crude compound was chromatographed using 0-20% ethyl acetate/hexanes gradient to give product (17 g, 83% yield) as a mixture of diastereomers in about 1:1 ratio. $^{31}$P NMR (162 MHz, DMSO-d6): δ −0.31, −0.47; $^1$H NMR (400 MHz, DMSO-d6): δ 8.31-8.27 (m, 2H), 7.51-7.37 (m, 4H), 7.27-7.19 (m, 3H), 6.70-6.63 (m, 1H), 4.85-4.78 (m, 1H), 3.97-3.86 (m, 1H), 1.21-1.19 (m, 3H), 1.11-1.09 (m, 6H); MS (ESI) m/z 407 (M−1)+. 31P NMR (162 MHz, CDCl3): δ −2.05, −2.10; 1H NMR (400 MHz, CDCl3): δ 8.22 (d, J=9.2 Hz, 2H), 7.41-7.33 (m, 4H), 7.26-7.18 (m, 3H), 5.05-4.96 (m, 1H), 4.14-4.05 (m, 1H), 3.93-3.88 (m, 1H), 1.38 (d, J=6.8 Hz, 3H), 1.22 (dd, J=6.2 & 3.0 Hz, 6H); MS (ESI) m/z 407 (M−1)+.

Example 5-2

Preparation of S$_P$-4/R$_P$-4

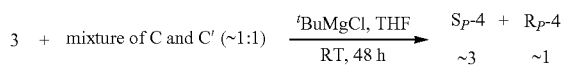

To a stirred solution of 1-((2R,3R,4R,5R)-3-Fluoro-4-hydroxy-5-hydroxymethyl-3-methyl-tetrahydro-furan-2-yl)-1H-pyrimidine-2,4-dione (130 mg, 0.5 mmol) in dry THF (1.5 mL) was added a 1.0M solution of tert-butylmagnesium chloride (1.05 mL, 1.05 mmol, 2.1 equiv)) at room temperature over a period of 5 min. After 30 min, a solution of (S)-2-[(4-nitro-phenoxy)-phenoxy-phosphorylamino] propionic acid isopropyl ester (1:1 mixture of isomers, 408 mg, 1 mmol) in THF (1.5 mL) was added drop-wise over a period of 5 min. The mixture was allowed to stir at room temperature for 48 h and then quenched with saturated aqueous NH4Cl (20 mL). The mixture was partitioned between ethyl acetate (50 mL) and water (20 mL). The combined organic extract was dried over anhydrous sodium sulfate, filtered and concentrated under reduced pressure to give a pale yellow residue. Column chromatography of the residue using 0-2% MeOH/dichloromethane gradient gave a white foamy solid (125 mg, 47% yield, mixture of S$_P$-4/R$_P$-4 in about 3.05:1.0 ratio).

Example 6

Preparation and non-chromatographic isolation of (S)-2-[(S)-(4-nitro-phenoxy)-phenoxy-phosphorylamino]propionic acid isopropyl ester

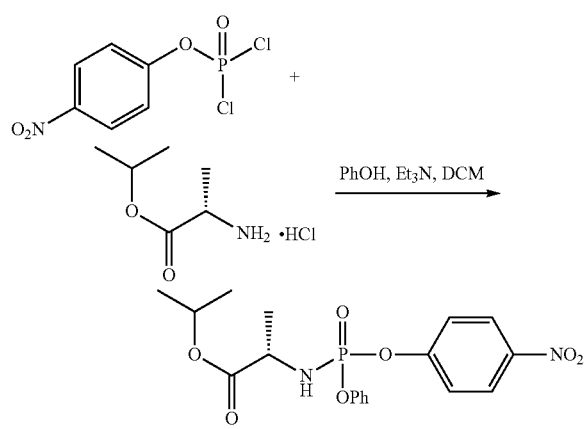

L-alanine isopropyl ester hydrochloride (330 g, 1.97 mol) was pre-dried by co-evaporation with toluene (2×400 mL) under reduced pressure and then dried in a vacuum oven (50° C., 0.2 mmHg, 17 h). To a stirred solution of 4-nitrophenyl phosphorodichloridate (500.0 g, 1.953 mol) in anhydrous dichloromethane (3.0 L) was added a solution of phenol (183.8 g, 1.953 mol) and triethylamine (300 mL, 2.15 mol) in dichloromethane (900 mL) at −60° C. internal temperature over a period of 3 hours. The mixture was stirred at this temperature for additional 30 min and then allowed to warm up to −5° C. over 2.5 hours. The pre-dried amino acid ester was added at −5-0° C. under an atmosphere of nitrogen over 10 mins. The residue of aminoester salt in the addition flask was transferred to the reaction mixture via rinsing with dichloromethane (2×100 mL). The mixture was stirred at 0° C. for 40 mins and a second portion of triethylamine (571 mL, 4.10 mol) was added over a period of 40 mins at 0° C. The mixture was stirred at 0~10° C. for 3 h and then the white solid (triethylamine hydrochloride) was filtered off and rinsed with dichloromethane (3×300 mL). The filtrate was concentrated under reduced pressure and the residue was triturated with methyl t-butyl ether (MTBE, 4 L). The additional solid salt thus formed was filtered off and rinsed with MTBE (3×150 mL). The filtrate was concentrated under reduced pressure to give clear light brown color oil. The residue was co-evaporated with hexanes (2×140 mL) to remove any residual MTBE and further dried under vacuum at 40° C. for 2 hours. The dry residue was mixed with diisopropyl ether (IPE, 1.1 L) and stirred at 5° C. in an ice-water bath. Small amount of crystal seeds of the desired S$_P$-isomer of the product was added to the solution and the mixture was stirred at 5° C. for over 22 h to form a medium thick slurry. This was allowed to stand in a freezer (−10° C.) for 44 h. The precipitated product was collected via filtration and rinsed with pre-cooled mixed solvents of IPE and hexanes (1:1, 3×190 mL). The solid was dried under vacuum (0.5 mm Hg) at ambient temperature until a constant weight was obtained to give 227.23 g (yield: 28.5%) as a white powder solid. The ratio of two diastereomers S$_P$:R$_P$ was 9.65:1 based on 31P NMR (162 MHz, DMSO-d6, δ −0.31 (S$_P$), −0.47 (R$_P$). The product was recrystallized by dissolving in IPE (840 mL) while heating in a 60° C. bath. The above solution was stirred at room temperature for 1 h and then a small amount of crystal Sp isomer seeds was added. White powder solid was formed within 2 hours and the flask was stored in a freezer (−10° C.) for 16 hours. A white and fine crystalline solid obtained was filtered, washed with pre-cooled IPE (3×50 mL) and dried under vacuum (ambient, 0.5 mm Hg) to a constant weight to give white fluffy solid (177.7 g, 22% overall yield or 44% overall yield based on theoretical yield of the Sp isomer) with diastereomeric ratio of 48/1 based on P-NMR. Mp 62-66° C.

31P NMR (162 MHz, DMSO-d6): δ −0.31; 1H NMR (400 MHz, DMSO-d6): δ 8.30-8.27 (m, 2H), 7.49 (d, J=8.8 Hz, 2H), 7.41-7.37 (m, 2H), 7.23-7.19 (m, 3H), 6.66 (dd, J=13.6, 10.0 Hz, 1H), 4.86-4.78 (m, 1H), 3.97-3.86 (m, 1H), 1.19 (d, J=7.2 Hz, 3H), 1.10 (d, J=6.4 Hz, 6H);

31P NMR (162 MHz, CDCl3): δ −2.05; (162 MHz, DMSO-d6): δ −0.31; 1H NMR (400 MHz, CDCl3): δ 8.22 (d, J=9.2 Hz, 2H), 7.41-7.33 (m, 4H), 7.26-7.18 (m, 3H), 5.05-4.96 (m, 1H), 4.14-4.05 (m, 1H), 3.93-3.88 (m, 1H), 1.38 (d, J=6.8 Hz, 3H), 1.22 (dd, J=6.2 & 3.0 Hz, 6H); 1H NMR (400 MHz, DMSO-d6): δ 8.30-8.27 (m, 2H), 7.49 (d, J=8.8 Hz, 2H), 7.41-7.37 (m, 2H), 7.23-7.19 (m, 3H), 6.66 (dd, J=13.6, 10.0 Hz, 1H), 4.86-4.78 (m, 1H), 3.97-3.86 (m, 1H), 1.19 (d, J=7.2 Hz, 3H), 1.10 (d, J=6.4 Hz, 6H)

MS (ESI) m/z 407 (M−1)+.

The stereochemistry of 8 (S$_P$-isomer) has been confirmed by single crystal X-ray crystallography, see details provided below.

Example 7

Separation of the diastereomeric mixture (S)-2-[(4-nitro-phenoxy)-phenoxy-phosphorylamino]propionic acid isopropyl ester by SFC A sample of the mixture of diastereomers (4.8 g) enriched with the $R_P$-isomer was subjected to SFC using a ChiralPak AD-H (2×15 cm) column and eluted with 35% isopropanol in carbon dioxide at 100 bar. An injection loading of 4 mL of sample at a concentration of 17 mg/mL of methanol was used. The $R_P$-isomer [(S)-2-[(R)-(4-nitro-phenoxy)-phenoxy-phosphorylamino]propionic acid isopropyl ester] eluted first. The appropriate fractions of the multiple runs were combined and concentrated under reduced pressure to give 2.9 g of the $R_P$-isomer [(S)-2-[(R)-(4-nitro-phenoxy)-phenoxy-phosphorylamino]propionic acid isopropyl ester] as a light yellow viscous oil and 1.9 g of the $S_P$-isomer [(S)-2-[(S)-(4-nitro-phenoxy)-phenoxy-phosphorylamino]propionic acid isopropyl ester] as a white solid. Analytical data of $R_P$-isomer is similar to the product isolated by the above crystallization method.

Analytical Data for (S)-2-[(R)-(4-nitro-phenoxy)-phenoxy-phosphorylamino]propionic acid isopropyl ester (8, $R_P$-isomer)

$^{31}$P NMR (162 MHz, DMSO-d6): δ −0.47; $^1$H NMR (400 MHz, DMSO-d6): δ 8.30-8.27 (m, 2H), 7.46-7.38 (m, 4H), 7.27-7.20 (m, 3H), 6.68 (dd, J=13.8, 10.2 Hz, 1H), 4.86-4.77 (m, 1H), 3.97-3.86 (m, 1H), 1.20 (d, J=7.2 Hz, 3H), 1.10 (dd, J=6.2, 2.2 Hz, 6H); MS (ESI) m/z 407 (M−1)$^+$.

Example 8-1

Preparation of racemic 2-[(4-chloro-phenoxy)-phenoxy-phosphorylamino]propionic acid isopropyl ester (±)

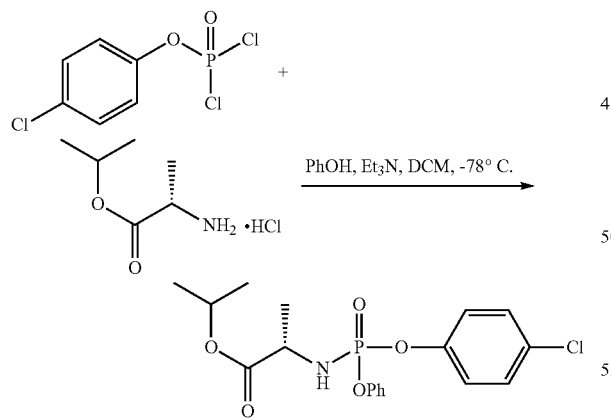

To a stirred solution of 4-chloro-phenyl phosphorodichloridate (2.45 g, 10.0 mmol) in dichloromethane (20 mL) was added a solution of phenol (0.94 g, 10 mmol) and triethylamine (1.56 mL, 11 mmol) in dichloromethane (20 mL) at −78° C. over a period of 20 min. The mixture was stirred at this temperature for 30 min and then transferred to another round bottom flask containing L-alanine isopropyl ester hydrochloride (1.67 g, 10 mmol) in dichloromethane (50 mL) at 0° C. To the mixture was added second lot of triethylamine (2.92 mL, 21 mmol) over a period of 15 min. The mixture was stirred at 0° C. for 1 h and then the solvent was evaporated. The residue was triturated with ethyl acetate (30 mL) and the white solid was filtered off. The filtrate was concentrated under reduced pressure to give pale yellow oil. The crude compound was chromatographed using 10-20% ethyl acetate/hexanes gradient to give product (2.0 g, 50% yield) as a mixture of diastereomers in about 1:1 ratio. $^{31}$P NMR (162 MHz, CDCl$_3$): δ −1.58, −1.62; $^1$H NMR (400 MHz, CDCl$_3$): δ 7.06-7.51 (m, 8H), 7.15-7.28 (m, 2H), 7.29-7.47 (m, 2H), 4.0-4.10 (m, 1H), 3.82-3.88 (m, 3H), 1.35-1.36 (dd, 6H); 1.19-1.22 (m, 3H). MS (ESI) m/z 398 (M−1)$^+$. The resultant product is purified by extraction, crystallization, or chromatography, as noted above.

Example 8-2

Preparation of (S)-Isopropyl 2-((2R,3R,4R,5R)-5-(2,4-dioxo-3,4-dihydropyrimidin-1(2H)-yl)-4-fluoro-3-hydroxy-4-methyltetrahydrofuran-2 yl)methoxy)(phenoxy)-phosphorylamino)propanoate (4)

To a stirred solution of 1-((2R,3R,4R,5R)-3-Fluoro-4-hydroxy-5-hydroxymethyl-3-methyl-tetrahydro-furan-2-yl)-1H-pyrimidine-2,4-dione (3, 2.6 g, 10 mmol) in dry THF (50 mL) was added a 1.7 M solution of tert-butylmagnesium chloride (12.4 mL, 21 mmol, 2.1 equiv)) at room temperature over a period of 15 min. After 30 min, a solution of racemic (2-[(4-chloro-phenoxy)-phenoxy-phosphorylamino]propionic acid isopropyl ester (4.08 g, 10 mmol) in THF (15 mL) was added drop wise over a period of 10 min. The mixture was allowed to stir at room temperature for 72. TLC co-spot with authentic product showed around 5% of the desired product had formed compared to the starting nucleoside.

Example 9-1

Preparation of racemic 2-[(2-chloro-phenoxy)-phenoxy-phosphorylamino]propionic acid isopropyl ester (±)

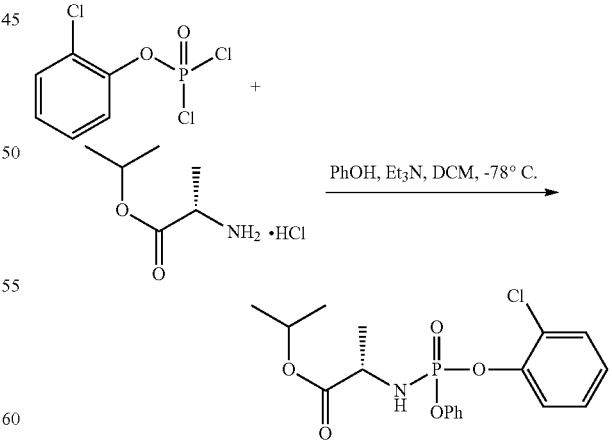

To a stirred solution of 2-chloro-phenyl phosphorodichloridate (9.8 g, 40 mmol) in dichloromethane (80 mL) was added a solution of phenol (3.76 g, 40 mmol) and triethylamine (6.16 mL, 44 mmol) in dichloromethane (80 mL) at −78° C. over a period of 20 min. The mixture was stirred at this temperature for 30 min and then transferred to another round bottom flask containing L-alanine isopropyl ester hydrochloride (6.7 g, 40 mmol) in dichloromethane (150 mL) at 0° C. To the mixture was added second portion of triethylamine (11.6 mL, 84 mmol) over a period of 15 min. The mixture was stirred at 0° C. for 1 h and then the solvent was evaporated. The residue was triturated with ethyl acetate (100 mL) and the white solid was filtered off. The filtrate was concentrated under reduced pressure to give pale yellow oil. The crude compound was chromatographed using 10-20% ethyl acetate/hexanes gradient to give product (11.3 g, 72% yield) as a mixture of diastereomers in about 1:1 ratio. $^{31}$P NMR (162 MHz, CDCl$_3$): δ −1.58, −1.61; $^1$H NMR (400 MHz, CDCl$_3$): δ 7.06-7.51 (m, 8H), 5.02-5.94 (m, 1H), 4.10-4.16 (m, 1H), 3.31-3.94 (m, 1H), 1.18-1.35 (m, 3H), 1.38-1.40 (dd, 6H); MS (ESI) m/z 398 (M−1)$^+$. The resultant product is purified by extraction, crystallization, or chromatography, as noted above.

Example 9-2

Preparation of (S)-isopropyl 2-((2R,3R,4R,5R)-5-(2, 4-dioxo-3,4-dihydropyrimidin-1(2H)-yl)-4-fluoro-3-hydroxy-4-methyltetrahydrofuran-2 yl)methoxy) (phenoxy)-phosphorylamino)propanoate To a stirred solution of 1-((2R,3R,4R,5R)-3-Fluoro-4-hydroxy-5-hydroxymethyl-3-methyl-tetrahydro-furan-2-yl)-1H-pyrimidine-2,4-dione (3, 2.6 g, 10 mmol) in dry THF (50 mL) was added a 1.7 M solution of tert-butylmagnesium chloride (12.4 mL, 21 mmol, 2.1 equiv)) at room temperature over a period of 15 min. After 30 min, a solution of (2-[(2-chloro-phenoxy)-phenoxy-phosphorylamino]propionic acid isopropyl ester (racemic 4.08 g, 10 mmol) in THF (15 mL) was added drop wise over a period of 10 min. The mixture was allowed to stir at room temperature for 72 h. TLC co-spot with authentic product showed around 5-10% of the desired product had formed compared to the starting nucleoside.

Example 10-1

Preparation of racemic 2-[(2,3,4,5,6-pentafluoro-phenoxy)-phenoxy-phosphorylamino]propionic acid isopropyl ester (±)

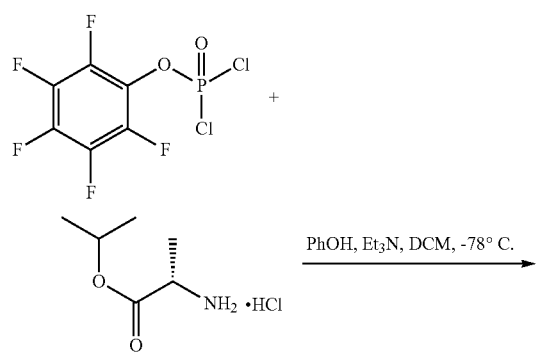

PhOH, Et$_3$N, DCM, -78° C.

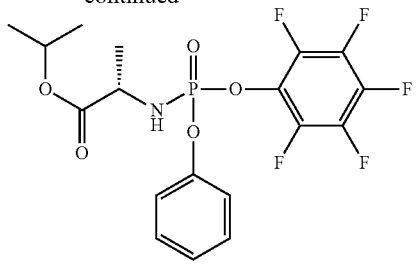

To a stirred solution of pentafluorophenyl phosphorodichloridate (6.0 g, 20 mmol) in dichloromethane (40 mL) was added a solution of phenol and triethylamine (3.08 mL, 22 mmol) in dichloromethane (40 mL) at −78° C. over a period of 20 min. The mixture was stirred at this temperature for 30 min and then transferred to another round bottom flask containing L-alanine isopropyl ester hydrochloride (3.35 g, 20 mmol) in dichloromethane (100 mL) at 0° C. To the mixture was added second lot of triethylamine (5.84 mL, 42 mmol) over a period of 15 min. The mixture was stirred at 0° C. for 1 h and then the solvent was evaporated. The residue was triturated with ethyl acetate (60 mL) and the white solid was filtered off. The filtrate was concentrated under reduced pressure to give pale yellow oil as a mixture of diastereomers in about 1:1 ratio. $^{31}$P NMR (162 MHz, CDCl$_3$): δ −0.49, −0.58. The resultant product is purified by extraction, crystallization, or chromatography, as noted above.

Example 10-2

Preparation of (S)-isopropyl 2-((2R,3R,4R,5R)-5-(2, 4-dioxo-3,4-dihydropyrimidin-1(2H)-yl)-4-fluoro-3-hydroxy-4-methyltetrahydrofuran-2 yl)methoxy) (phenoxy)-phosphorylamino)propanoate To a stirred solution of 1-((2R,3R,4R,5R)-3-Fluoro-4-hydroxy-5-hydroxymethyl-3-methyl-tetrahydro-furan-2-yl)-1H-pyrimidine-2,4-dione (3, 2.6 g, 10 mmol) in dry THF (50 mL) was added a 1.7M solution of tert-butylmagnesium chloride (12.4 mL, 21 mmol, 2.1 equiv)) at room temperature over a period of 15 min. After 30 min, a solution of crude racemic (2-[(2,3,4,5,6-pentafluoro phenoxy)-phenoxy-phosphorylamino]propionic acid isopropyl ester (4.08 g, 10 mmol) in THF (15 mL) was added drop wise over a period of 10 min. The mixture was allowed to stir at room temperature for 72 h. TLC co-spot with authentic product showed around 40-50% of the desired product had formed compared to the starting nucleoside.

The preparation and purification of C or C' provides for direct access to either S$_P$-4 or R$_P$-4, as illustrated in the following examples.

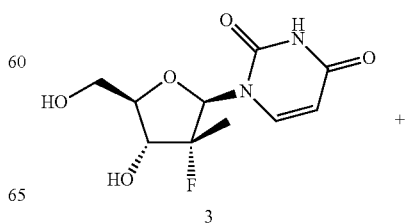

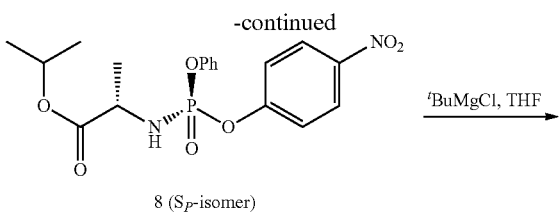

8 (S$_P$-isomer)

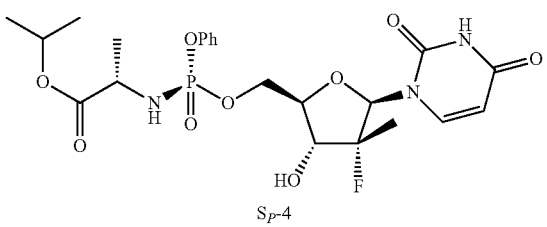

S$_P$-4

Example 11

Preparation of S$_P$-4 (32 mg-scale)

To a stirred solution of 1-((2R,3R,4R,5R)-3-Fluoro-4-hydroxy-5-hydroxymethyl-3-methyl-tetrahydro-furan-2-yl)-1H-pyrimidine-2,4-dione 3 (32 mg, 0.12 mmol) in dry THF (1 mL) was added a 1M solution of tButylmagnesium chloride (0.26 mL, 0.26 mmol, 2.1 equiv)) at room temperature over a period of 3 min. After 30 min, a solution of (S)-2-[(S)-(4-nitro-phenoxy)-phenoxy-phosphorylamino] propionic acid isopropyl ester (8, S$_P$-isomer) in THF (0.5 mL) was added drop wise over a period of 3 min. The mixture was allowed to stir at room temperature for 42 h and then quenched with saturated aqueous NH$_4$Cl (10 mL). The mixture was partitioned between ethyl acetate and water. The combined organic extract was dried over anhydrous sodium sulfate and concentrated. The residue was chromatographed using 0-4% methanol/dichloromethane gradient to give S$_P$-4 as foamy solid (29 mg, 44.5% yield). $^1$H and $^{31}$P NMR agree to that which is disclosed herein.

Example 12

Preparation of S$_P$-4 (2.6 g-scale, without chromatography)

To a stirred solution of 1-((2R,3R,4R,5R)-3-Fluoro-4-hydroxy-5-hydroxymethyl-3-methyl-tetrahydro-furan-2-yl)-1H-pyrimidine-2,4-dione (2.6 g, 10 mmol) in dry THF (50 mL) was added a 1.7 M solution of tert-butylmagnesium chloride (12.4 mL, 21 mmol, 2.1 equiv)) at room temperature over a period of 15 min. After 30 min, a solution of (S)-2-[(S)-(4-nitro-phenoxy)-phenoxy-phosphorylamino] propionic acid isopropyl ester (8, Sp-isomer, 4.08 g, 10 mmol) in THF (15 mL) was added drop wise over a period of 10 min. The mixture was allowed to stir at room temperature for 60 h and then quenched with saturated aqueous NH$_4$Cl (20 mL). The mixture was partitioned between ethyl acetate (150 mL) and sequentially, 10% aqueous Na$_2$CO$_3$ (3×20 mL) and water (20 mL). The combined organic extract was dried over anhydrous sodium sulfate, filtered and concentrated under reduced pressure to give a pale yellow residue (3.8 g). The residue was dissolved in dichloromethane (7.6 mL) and then stirred for 20 h at room temperature. The white solid was filtered, washed with 1:1 IPE/dichloromethane (5 mL) and dried under vacuum to give pure product as white solid (1.85 g, 35% yield).

Example 13

Preparation of S$_P$-4 using NaHMDS

To a stirred solution of 1-((2R,3R,4R,5R)-3-Fluoro-4-hydroxy-5-hydroxymethyl-3-methyl-tetrahydro-furan-2-yl)-1H-pyrimidine-2,4-dione (71 mg, 0.27 mmol) in dry THF (2.0 mL) was added a 2.0 M solution of sodium bis(trimethylsilyl)amide (NaHMDS) in THF (270 µL, 0.54 mmol) at −78° C. over a period of 2 min. After 30 min, a solution of (S)-2-[(S)-(4-Nitro-phenoxy)-phenoxy-phosphorylamino]-propionic acid isopropyl ester (8, S$_P$-isomer, 111 mg, 0.27 mmol) in THF (1 mL) was added to the mixture. The reaction mixture was allowed stir at this temperature for 2 h and then warmed to −20° C. at which temperature it was stirred for additional 20 h. TLC indicated ~30% of unreacted nucleoside starting material. Hence, additional 0.5 equivalents of the reagent (55 mg, 0.14 mmol) in THF (0.5 mL) was added to the reaction mixture and stirred for another 6 h. The reaction mixture was quenched with saturated aqueous ammonium chloride solution and then partitioned between ethyl acetate and water. The combined organic extract was dried over anhydrous sodium sulfate and concentrated to give a light brown residue. Column chromatography of the crude product using 0-5% methanol/dichloromethane gradient gave S$_P$-4 (22 mg, 15% yield), 3'-phosphoramidate (5, S$_P$-isomer, 11.5 mg, 16% yield) and bis phosphoramidate (6, Sp, S$_P$-isomer, 12.6 mg).

Example 14

Preparation of R$_P$-4 (260 mg-scale)

To a stirred solution of 1-((2R,3R,4R,5R)-3-Fluoro-4-hydroxy-5-hydroxymethyl-3-methyl-tetrahydro-furan-2-yl)-1H-pyrimidine-2,4-dione (260 mg, 1 mmol) in dry THF (6 mL) was added a 1.7 M solution of tert-butylmagnesium chloride (1.23 mL, 2.1 mmol, 2.1 equiv)) at room temperature over a period of 5 min. After 30 min, a solution of (S)-2-[(R)-(4-nitro-phenoxy)-phenoxy-phosphorylamino] propionic acid isopropyl ester (8, R$_P$-isomer) in THF (3 mL) was added drop wise over a period of 3 min. The mixture was allowed to stir at room temperature for 96 h and then quenched with saturated aqueous NH$_4$Cl (10 mL). The mixture was partitioned between ethyl acetate (50 mL) and water (2×20 mL). The combined organic extract was dried over anhydrous sodium sulfate, filtered and concentrated under reduced pressure to give a pale yellow residue (490 mg). The residue was chromatographed using 0-5% methanol/dichloromethane gradient to give product as a white solid (160 mg, 30% yield).

The preparation of S$_P$-4 or R$_P$-4 may also be achieved by reacting 3'-protected 3 with the appropriate reagent C or C' or a mixture containing C and C', as illustrated in the following examples.

Example 15
Preparation of S$_P$-4 with 3a as a Synthetic Intermediate
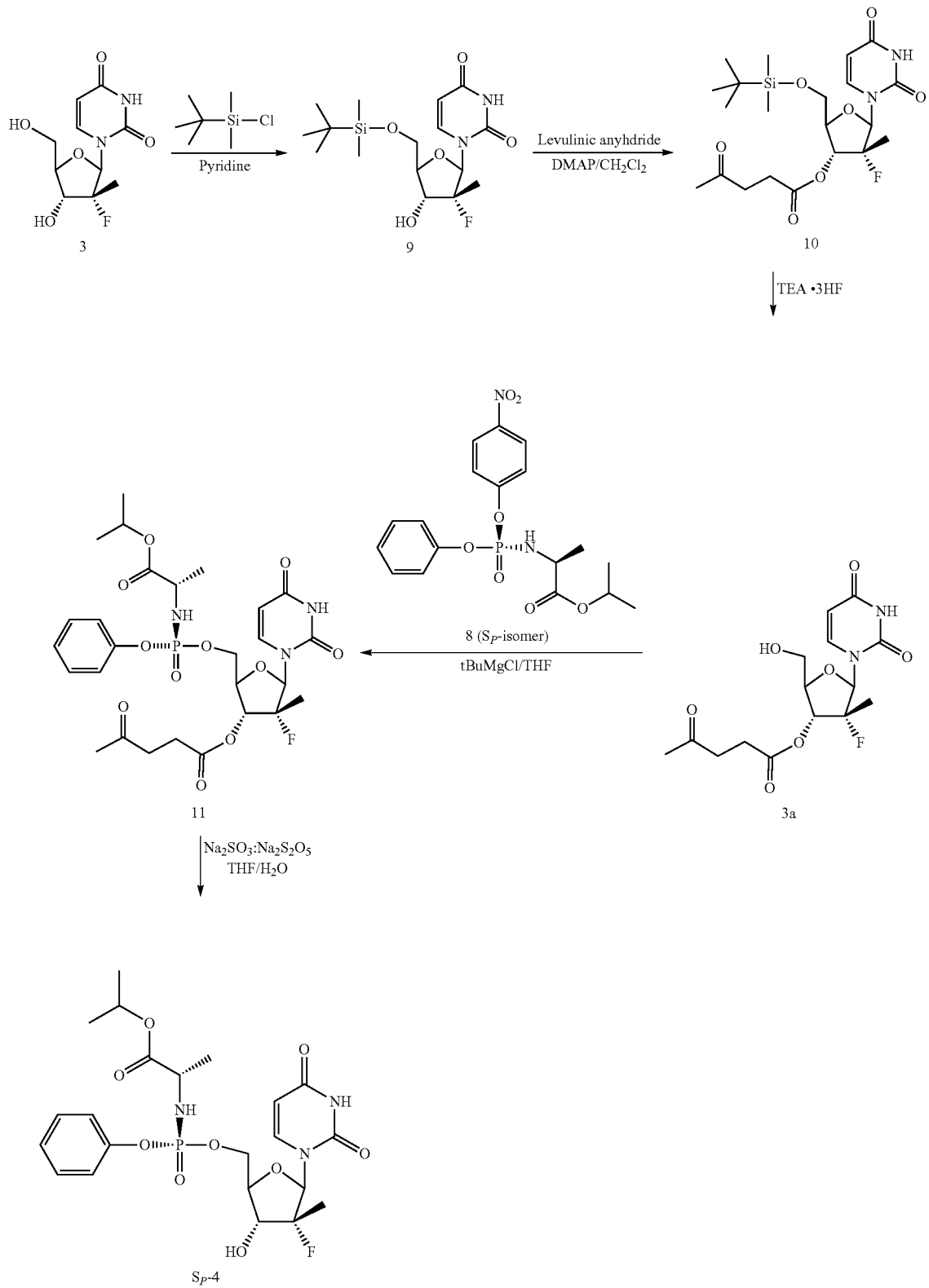

Example 15-1

Synthesis of 5'-O-tert-Butyldimethylsilyl-2'-deoxy-2'-fluoro-2'-C-methyluridine (9)

To a stirred solution of 2'-deoxy-2'-fluoro-2'-C-methyluridine (3, 81.1 g, 312 mmol) in dry pyridine (750 mL) was added drop-wise a solution of TBDMSCl (103.19 g, 685.6 mmol) in dry pyridine (500 mL) over a period of 45 min at ambient temperature. The reaction was allowed to stir at ambient temperature for 24 h. Methanol (85 mL) was added to the reaction mixture and it was allowed to stir for 10 min and then the solvents were distilled off under reduced pressure. Hot water (45° C.) (1 L) was added to the reaction mass and the mixture extracted with ethyl acetate (2×500 mL), washed with water (1×500 mL). The organic layer was dried over anhydrous sodium sulfate. Ethyl acetate was distilled off and the residue obtained was co-evaporated with toluene (2×500 mL) to give crude 9 as a white foam. Yield=116.9 g (quantitative). $^1$H NMR (CDCl$_3$, 300 MHz): δ 0.1 (s, 6H), 0.91 (s, 9H), 1.22 (d, 3H, J=21 Hz), 2.50 (s, 2H), 3.75-4.05 (m, 4H), 5.54 (d, 1H, J=9 Hz), 5.73 (s, 1H), 6.0 (d, 1H, J=18 Hz), 7.81 (d, 1H, J=9 Hz), 8.57 (br, s, 1H), 11.1 (s, 1H).

Example 15-2

Synthesis of 5'-O-(tert-Butyldimethylsilyl)-3'-O-levulinyl-2'-deoxy-2'-fluoro 2'-C-methyl-uridine (10)

To a stirred solution of nucleoside 9 (116.9 g, 312.1 mmol) in DCM (1 L) was added DMAP (30.5 g, 249.7 mmol) and this was allowed to stir at RT for 20 min. A soln. of levulinic anhydride (133.6 g, 642.3 mmol) in DCM (200 mL) was added to the mixture and allowed to stir for 24 h. TLC of the mixture indicated completion of reaction. Cold water (500 mL) was added and the mixture stirred for 20 min. Layers were separated and the organic layer was washed with sat. sodium bicarbonate solution (2×250 mL), dried over anhydrous sodium sulfate and then the solvent was distilled under reduced pressure to give yellow oil. Crude yield: 197.6 g (135%). The material was used as is for the next step. $^1$H NMR (CDCl$_3$, 300 MHz) δ 0.11 (s, 6H), 0.94 (s, 9H), 1.34 (d, 3H, J=21 Hz), 2.22 (s, 3H), 2.6-2.89 (m, 4H), 3.72 (m, 1H), 4.01 (d, 1H, J=12 Hz), 4.23 (d, 1H, J=9 Hz), 5.33 (dd, 1H, J=15 Hz), 5.73 (d, 1H, J=6 Hz), 6.26 (d, 1H, J=15 Hz), 8.12 (d, 1H, J=12 Hz), 8.72 (br, s, 1H).

Example 15-3

Synthesis of 3'-O-levulinyl-2'-deoxy-2'-fluoro 2'-C-methyl-uridine (3a)

Crude 10 (197.6 g, 312.1 mmol) was dissolved in DCM (1 L) to which was added TEA.3HF (50.3 g, 312.1 mmol) and allowed to stir overnight at ambient temperature. TLC of the mixture indicated about 50% completion of reaction. Another equivalent of TEA.3HF (50.3 g, 312.1 mmol) was added and the reaction mixture was allowed to stir for 6 h. TLC at this point indicated about 10% of unreacted starting material. Another 0.25 eq of TEA.3HF (12.5 g, 78.0 mmol) was added and the reaction mixture was allowed to stir overnight. Reaction mixture was concentrated to dryness to give yellow oil. Crude from all the batches was purified by column chromatography on silica gel (0-2% MeOH in DCM) to give 124.1 g of 3'-levulinate as a white foam solid (90% purified yield over three steps from 2'-deoxy-2'-fluoro-2'-C-methyluridine). $^1$H NMR: (CDCl$_3$, 400 MHz) δ 1.55 (d, 3H, CH$_3$, J=20 Hz), 2.36 (s, 3H, CH3), 2.8-3.03 (m, 5H, CH2CH3), 3.91-3.96 (dd, 1H, CH"), 4.2-4.25 (m, 1H, CH'), 4.34 (dd, 1H, CH, J=8 Hz), 5.25 (dd, 1H, J=16 Hz), 5.93 (d, 1H, J=8 Hz), 8.20 (d, 1H, J=8 Hz), 9.18 (s, 1H).

Example 15-4

Stereoselective synthesis of (S)-2-{[(1R,4R,5R)-5-(2,4-Dioxo-3,4-dihydro-2H-pyrimidin-1-yl)-4-(R)-fluoro-3-(4-oxopentanoyl)-4-methyl-tetrahydro-furan-2-ylmethoxy]-phenoxy-phosphorylamino}-propionic acid (S)-isopropyl ester (11)

To a solution of the nucleoside (3a, 1.00 mmol, 358 mg) in 5 ml anhydrous THF that was cooled to 0° C. was added tBuMgCl (1.7 M in THF, 2 eq) and allowed it to warm to ambient temperature and stirred for half hour. To this mixture was added the reagent (ca. 97% chiral purity) (S)-2-[(S)-(4-nitro-phenoxy)-phenoxy-phosphorylamino]propionic acid isopropyl ester (8, S$_P$-isomer) (408 mg, 1.00 mmol, 1.00 eq.) in one lot and allowed to stir at rt. After 16 h, there was ~30% starting material left. The reaction mixture was quenched with saturated NH$_4$Cl solution 10 ml, and the aqueous phase was extracted with ethyl acetate (3×25 ml). The combined organic layer was washed with brine and dried over anhydrous sodium sulfate and evaporated to dryness to give a pale yellow foam (500 mg). This was purified by silica gel chromatography using 2-5% methanol in methylene chloride to give the product as a white foam (275 mg) of about 97% P chiral purity and unreacted starting material (162 mg). Based on consumed starting material, the yield was 76%. $^{31}$P NMR (CDCl$_3$, 162 MHz): 3.7 ppm; $^1$H NMR (CDCl$_3$, 400 MHz): δ 1.22 (dd, 6H, J=6.4 Hz), 1.37 (s, 3H), 1.58 (s, 3H), 2.18 (s, 3H), 2.63-2.9 (m, 4H), 4.0 (d, 1H, J=8 Hz), 4.2-4.33 (m, 1H), 4.57 (d, 1H, J=8 Hz), 4.96-5.00 (sept, 1H), 5.2 (dd, 1H, J=9 Hz), 5.42 (d, 1H, J=8 Hz), 6.19 (d, 1H, J=18 Hz), 7.15-7.35 (m, 5H), 7.5 (d, 1H, J=5.6 Hz), 8.2 (br, s, 1H).

Example 15-5

Synthesis of (S)-2-{[(1R,4R,5R)-5-(2,4-Dioxo-3,4-dihydro-2H-pyrimidin-1-yl)-4-(R)-fluoro-3-hydroxy-4-methyl-tetrahydro-furan-2-ylmethoxy]-phenoxy-phosphorylamino}-propionic acid (S)-isopropyl ester (S$_P$-4)

A solution of sodium sulfite was prepared by adding Na$_2$S$_2$O$_3$ (1.51 g) and Na$_2$S$_2$O$_5$ (0.57 g) in water (25 mL). To a solution of the levulinate (11, 250 mg, 0.40 mmol) in anhydrous THF (2.5 mL) was added 1.0 ml of the sodium sulfite solution. This was allowed to stir at room temperature for 4 h. The reaction mixture was poured in to water (15 mL) and extracted with ethyl acetate (3×25 mL) dried and evaporated to give quantitatively a white solid product with about 97% P chiral purity which matched the physical and spectral properties of S$_P$-4 produced directly from the unprotected nucleoside.

Example 16

Alternative Procedure for Preparing S$_P$-4 from 3a

To a stirred solution of 4-oxo-pentanoic acid (2R,3R,4R,5R)-5-(2,4-dioxo-3,4-dihydro-2H-pyrimidin-1-yl)-4-fluoro- 2-hydroxymethyl-4-methyl-tetrahydro-furan-3-yl ester (3a, 210 mg, 0.59 mmol) in dry THF (1.5 mL) was added a 1.7 M solution of tert-butylmagnesium chloride (1.07 mL, 1.82 mmol) at room temperature over a period of 2 min. Initially, a white precipitate was observed and after 10 min the reaction mixture turned to dark yellow solution. After 30 min, a solution of (S)-2-[(S)-(4-nitrophenoxy)-phenoxyphosphorylamino]-propionic acid isopropyl ester (8 ($S_P$-isomer), 382 mg, 0.94 mmol) in THF (1.5 mL) was added drop wise over a period of 3 min. The mixture was heated at 40° C. for 5 h at which time TLC and $^1$H NMR indicated less than 2% of unreacted starting material. The reaction was quenched with saturated aqueous ammonium chloride and then partitioned between ethyl acetate and water. The combined organic layer was washed with 10% aqueous $Na_2CO_3$ solution (3×10 mL), followed by water. The organic layer was dried over anhydrous sodium sulfate and concentrated to give brown color residue (410 mg). The crude product was dissolved in tetrahydrofuran (1.0 mL) and then was added an aqueous solution of the mixture of sodium sulfite (37 mg, 0.295 mmol) and sodium metabisulfite (224 mg, 1.18 mmol) in 1 mL of water. The mixture was heated at 45° C. for 20 h at which stage only about 10% conversion was observed by TLC, hence the additional sodium sulfite (74 mg) and sodium metabisulfite (448 mg) was added and the heating was continued for additional 52 h. At this time, about 40% conversion observed by TLC. The reaction mixture was partitioned between water and ethyl acetate. The combined organic layer was dried over anhydrous sodium sulfate and concentrated to give a brown residue (210 mg). Column chromatography of the residue using 0-5% MeOH/DCM gradient gave unreacted starting material (89 mg) and $S_P$-4 (57 mg, 18% yield, 24% based on recovered starting material).

Example 17

Preparation of $S_P$-4 with 3c as a Synthetic Intermediate

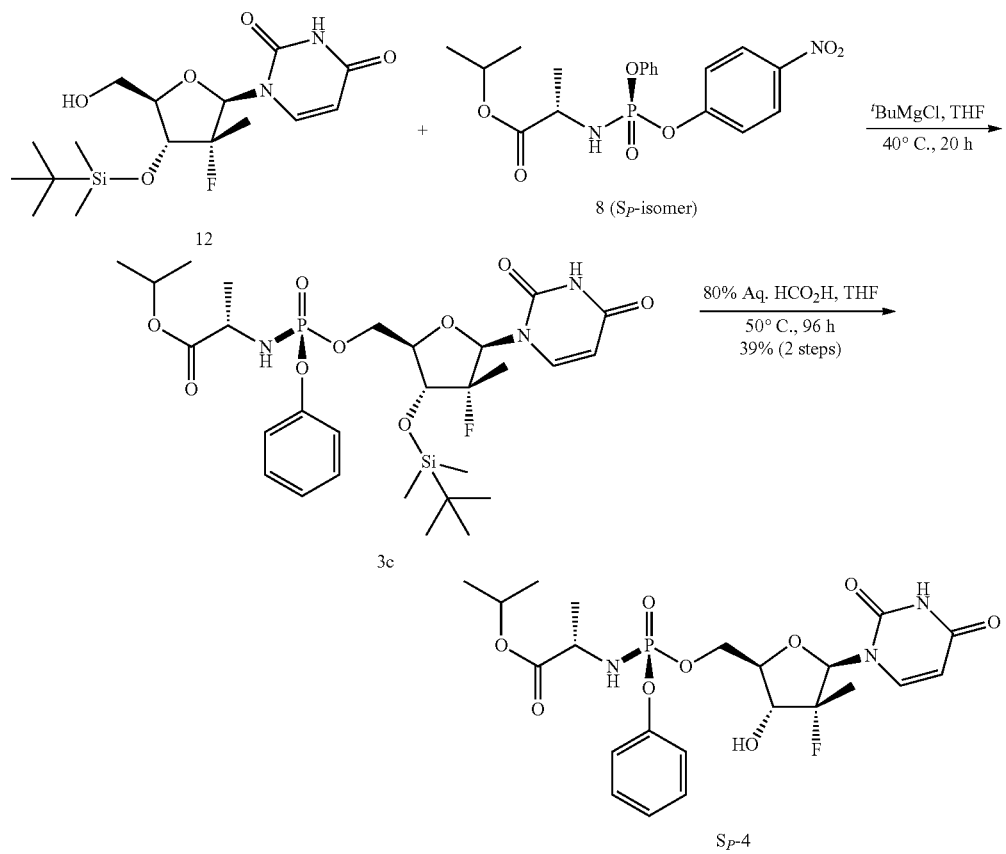

Example 17-1

Preparation of 1-[(2R,3R,4R,5R)-4-(tert-butyldimethylsilanyloxy)-3-fluoro-5-hydroxymethyl-3-methyl-tetrahydro-furan-2-yl]-1H-pyrimidine-2,4-dione, 12

To a solution of 3 (10.0 g, 38.43 mmol) in pyridine (50 mL) were added dichloromethane (50 mL). The solution was cooled to 0° C. To the solution was added 4,4'-dimethoxytrityl chloride (14.32 g, 42.27 mmol) and the solution was stirred at 0° C. for 5 h. Methanol (5 mL) was added to quench the reaction. The solution was concentrated to dryness under reduced pressure and the residue was partitioned between ethyl acetate (500 mL) and water (50 mL). The organic solution was washed with brine (50 mL) and dried (sodium sulfate, 4 g). The solvent was removed under reduced pressure and the residue was dissolved in dichloromethane (100 mL). To the solution were added imidazole (7.83 g, 115 mmol) and t-butyldimethylsilyl chloride (8.68 g, 57.6 mmol). The solution was stirred at ambient temperature for 16 h. Methanol was added to quench the reaction (5 mL) and the solvent was removed under reduced pressure and the residue was partitioned between ethyl acetate (500 mL) and water (50 mL). The organic solution was dried (sodium sulfate, 4 g) and evaporated under reduced pressure. The residue was purified by column chromatography (10-40% EtOAc in Hexane) to give 5'-O-DMT-3'-O-tBDMS intermediate product. This is turn was treated with 1% trifluoroacetic acid in dichloromethane (200 mL). The solution was stirred at ambient temperature for 1 h. Water (20 mL) was added and the solution was stirred at ambient for another 1 h. Methanol (5 mL) was slowly added and the solution was stirred at ambient for another 1 h. Ammonium hydroxide was added to adjust the solution pH to 7. The organic solution was separated, dried (sodium sulfate, 4 g) and evaporated to dryness under reduced pressure. The residue was purified by silica gel column chromatography (1-5% methanol in dichloromethane) to give 12 as a white solid 7.5 g in 50% yield over the three steps. $^1$H NMR (DMSO-d6) δ (ppm) 11.48 (br s, 1H, NH), 7.94 (d, 1H, H-6), 6.00 (d, 1H, H-1'), 5.69 (d, 1H, H-5), 4.06 (dd, 1H, 3'-H), 3.85 (m, 2H, H-5' a, H-4'), 3.58 (br d, 1H, H-5' b), 1.27 (d, 3H, 2-CH$_3$), 0.89 (s, 9H, C(CH$_3$)$_3$), 0.12 (s, 6H, Si(CH$_3$)$_2$).

Example 17-2

Preparation of S$_P$-4 using 1-[(2R,3R,4R,5R)-4-(tert-butyldimethylsilanyloxy)-3-fluoro-5-hydroxymethyl-3-methyl-tetrahydro-furan-2-yl]-1H-pyrimidine-2,4-dione (3c)

To a stirred solution of 1-[(2R,3R,4R,5R)-4-(tert-butyldimethylsilanyloxy)-3-fluoro-5-hydroxymethyl-3-methyl-tetrahydro-furan-2-yl]-1H-pyrimidine-2,4-dione (12, 374 mg, 1 mmol) in dry THF (3 mL) was added a 1.7 M solution of tert-butylmagnesium chloride (1.8 mL, 3.1 mmol)) at room temperature over a period of 2 min. Initially, a white precipitate was observed and after 10 min the reaction mixture turned to clear dark yellow solution. After 30 min, a solution of (S)-2-[(S)-(4-nitrophenoxy)-phenoxy-phosphorylamino]-propionic acid isopropyl ester (8, S$_P$-isomer, 653 mg, 1.6 mmol) in THF (2.5 mL) was added drop wise over a period of 3 min. The mixture was heated at 40° C. for 20 h at which time TLC and $^1$H NMR indicated less than 5% of unreacted starting material. The reaction mixture was quenched with saturated aqueous ammonium chloride and then partitioned between ethyl acetate and water. The organic layer was washed with 10% aqueous Na$_2$CO$_3$ solution (3×10 mL), followed by water (20 mL). The organic layer was dried over anhydrous sodium sulfate and concentrated to give brown residue containing 3c (850 mg). The crude product was dissolved in tetrahydrofuran (2 mL) and was added 0.8 mL of 80% aqueous formic acid at room temperature. The reaction mixture was heated at 50° C. for 96 h. About 70% conversion was observed by TLC. The reaction mixture was poured into cold saturated aqueous sodium bicarbonate and then partitioned between ethyl acetate and water. The combined organic layer was dried over anhydrous sodium sulfate and concentrated to give brown residue (220 mg). Column chromatography of the residue using 0-5% MeOH/DCM gradient gave unreacted starting material (21 mg) and S$_P$-4 (77 mg, 35% yield, 39% yield based on recovered starting material).

Example 18

Preparation of S$_P$-4 with 3d as a Synthetic Intermediate

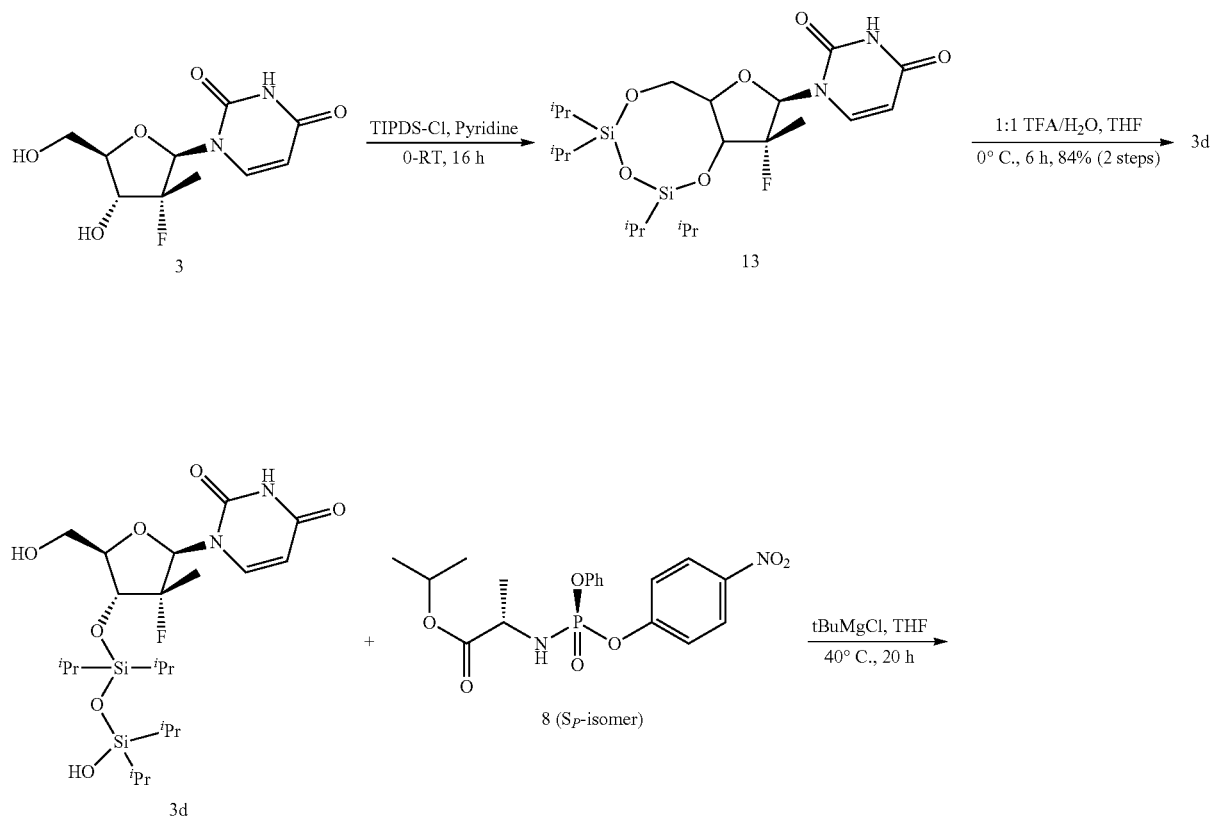

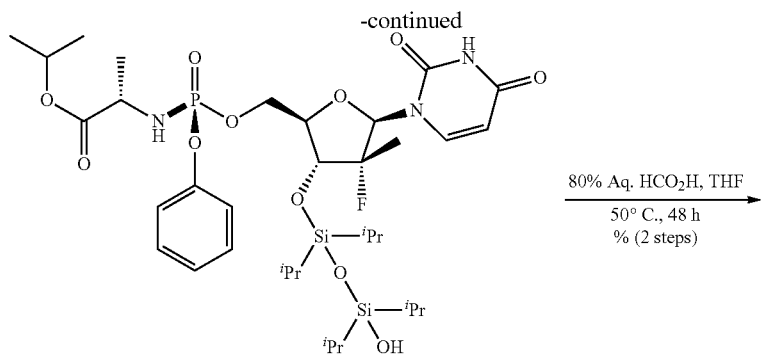

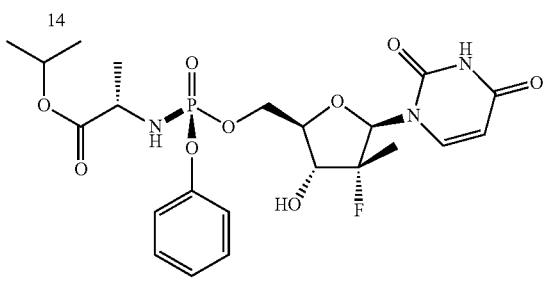

Example 18-1

Preparation of 3d

To a stirred solution of 3 in pyridine (20 mL) at 0° C. was added TIPDS-Cl drop-wise over a period of 15 min. The mixture was slowly allowed to warm to room temperature at which temperature it was stirred for 16 h. The pyridine was evaporated and the residue was co-evaporated with toluene (50 mL). The residue was then triturated with hexanes and the white precipitate was filtered off using a pad of Celite. The filtrate was concentrated under reduced pressure to give a foamy solid (12.97 g). The crude product (13) was redissolved in tetrahydrofuran (75 mL) and was added an aqueous solution of TFA (75 mL, 1:1 TFA/water) at 0° C. over a period of 20 min. The mixture was stirred at this temperature for 6 h. TLC indicated ~5% of starting material. The reaction mixture was quenched with saturated aqueous NaHCO$_3$ until pH 8 and then extracted with ethyl acetate. The combined organic extract was washed with water, dried and concentrated to give white crystalline solid. Further trituration of the solid with hexanes (30 mL) gave white solid which was filtered and dried under high vacuum to give 3d (10.1 g, 84% yield over 2 steps). $^1$H NMR (400 MHz, CDCl$_3$): δ 8.83 (bs, 1H), 7.94 (bd, J=6.0 Hz, 1H), 6.10 (bd, J=18.4 Hz, 1H), 5.71 (d, J=8.2 Hz, 1H), 4.43 (bs, 1H), 4.36 (dd, J=22.6, 9.0 Hz, 1H), 4.27 (bs, 1H), 4.10 (d, J=13.2 Hz, 1H), 4.03 (d, J=9.2 Hz, 1H), 3.92 (d, J=13.2 Hz, 1H), 1.39 (d, J=22.0 Hz, 3H), 1.11-0.92 (m, 28H).

Example 18-2

Preparation of S$_P$-4

To a stirred solution of 3d (520 mg, 1 mmol) in dry THF (5 mL) was added a 1.7M solution of tert-butylmagnesium chloride (1.8 mL, 3.1 mmol, 3.1 equiv)) at room temperature over a period of 15 min. After 30 min, a solution of (S)-2-[(S)-(4-nitro-phenoxy)-phenoxyphosphorylamino] propionic acid isopropyl ester (8, S$_P$-isomer, 653 mg, 1.6 mmol) in THF (1 mL) was added drop wise over a period of 3 min. The mixture was allowed to stir at room temperature for 60 h. $^1$H and $^{31}$P NMR of the crude sample indicated mixture of diastereomers in about 1:0.76. The reaction mixture was quenched with saturated aqueous NH$_4$Cl (20 mL). The mixture was partitioned between ethyl acetate (150 mL) and sequentially, 10% aqueous Na$_2$CO$_3$ (3×20 mL) and water (20 mL). The combined organic extract was dried over anhydrous sodium sulfate, filtered and concentrated under reduced pressure to give a pale yellow residue (14, 878 mg). The above compound, 14, was redissolved in tetrahydrofuran (3 mL) and then was added 80% aqueous formic acid. The mixture was heated at 55° C. for 20 h. The reaction mixture was cooled to 0° C., and then quenched with saturated aqueous sodium bicarbonate (pH 7.0). The reaction mixture was then partitioned between ethyl acetate and water. The combined organic layer was dried over sodium sulfate and concentrated to give 560 mg of the residue. The residue was chromatographed using 0-5% methanol/dichloromethane gradient to give unreacted starting material (14, 242 mg) and S$_P$-4 (80 mg, 15% yield) as a white solid.

Example 19

Preparation of Isotopically Labeled S$_P$-4

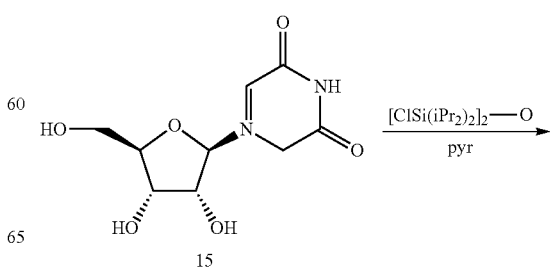

-continued

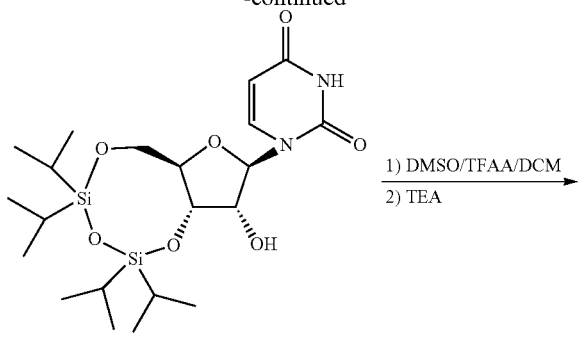
16

1) DMSO/TFAA/DCM
2) TEA
→

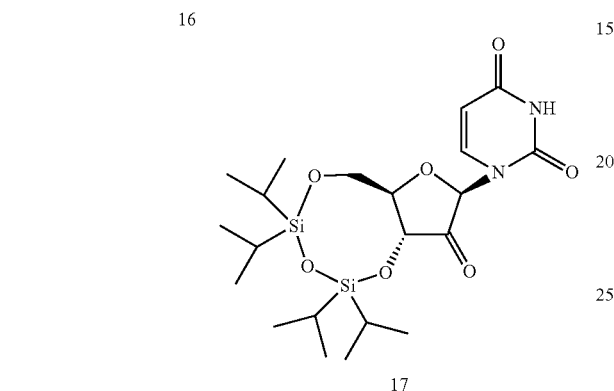
17

17
1) Mg, CD₃I, ether
2) NH₄F, THF
→

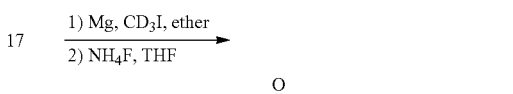
18

Ac₂O, pyridine →

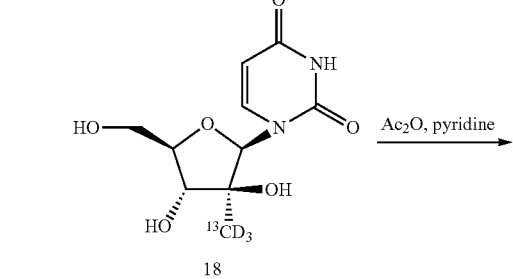
19

19
DAST, CH₂Cl₂, rt
→

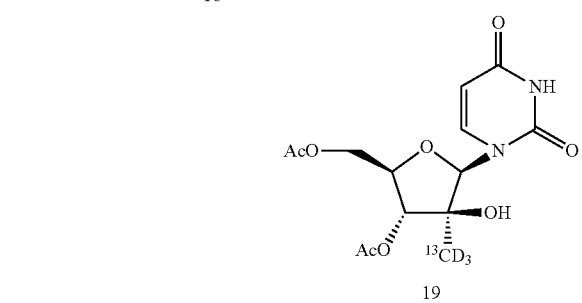
20 n-BuNH₂
MeOH
→

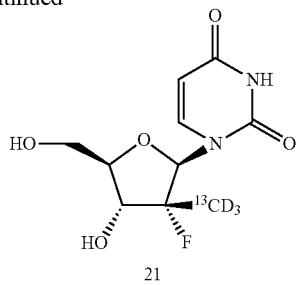
21

Example 19-1

Preparation of 1-((6aR,8R,9R,9aS)-9-hydroxy-2,2,4,4-tetraisopropyltetrahydro-6H-furo [3,2-f][1,3,5,2,4] trioxadisilocin-8-yl)pyrimidine-2,4(1H,3H)-dione, 16

Uridine (15, 100.0 g, 409.5 mmol) was co-evaporated to dryness with anhydrous pyridine (600 mL) and re-suspended in anhydrous pyridine (700 mL). To this stirred fine suspension was added 1,3-dichloro-1,1,3,3-tetraisopropyldisiloxane (135.7 g, 482.5 mmol) over 60 min at ambient temperature. After stirring the fine suspension for 17 h at ambient temperature, the reaction was quenched by adding methanol (20 mL) and then concentrated under reduced pressure. The residue was partitioned between ethyl acetate (1.5 L) and water (2 L). The organic layer was further washed with 5% hydrochloric acid (2×1 L), brine (500 mL), dried over solid sodium sulfate (50 g), filtered and concentrated under reduced pressure to the crude product, ca 250 g. The residue was subjected to a filtration column using silica gel (1.75 kg) and a gradient of ethyl acetate in hexanes 20-65%. The pure product fractions as judged by a homogenous TLC (Rf 0.55 in 1:1 hexanes-ethyl acetate) were combined and concentrated under reduced pressure and dried (40° C., 0.2 mm Hg, 24 h) to afford 145.5 g (76%) of 16 as a white foam solid. An additional fraction (35 g) of slightly impure 16 was also collected. ¹H NMR (DMSO-d₆) δ (ppm) 11.35 (s, 1H, NH), 7.66 (d, 1H, J=7.6 Hz, H-6), 5.57 (d, 1H, J=4.8 Hz, 2'-OH), 5.50-5.49 (m, 2H, 1'-H and H-5), 4.14-4.18 (m, 3H, 2', 3', 4'-H), 3.97-3.87 (m, 2H, 5'-Ha and Hb), 1.02-0.95 (m, 28H, CH(CH₃)₂).

Example 19-2

Preparation of 1-((6aR,8R,9aR)-2,2,4,4-tetraisopropyl-9-oxotetrahydro-6H-furo [3,2-f][1,3,5,2,4]trioxadisilocin-8-yl)pyrimidine-2,4(1H,3H)-dione, 17

To a dry three-necked round flask were added anhydrous DCM (600 mL) and DMSO (30.82 g, 394.5 mmol). The solution was cooled to −78° C. in a dry ice/acetone bath under an atmosphere of nitrogen. Trifluoroacetic anhydride (neat, 77.7 g, 369.8 mmol) was added via a syringe over 40 mins and afforded a cloudy mixture. To the mixture a solution of uridine derivative 16 in DCM (600 mL) was added dropwise over 75 mins at −78° C. via an addition funnel. The heterogeneous mixture was stirred for 2 h at −78~−65° C. and then anhydrous triethylamine (92 mL) was added via a syringe quickly to form a clear light yellow solution. After 1 h at low temperature, the reaction was complete as shown by TLC (30% EtOAc in hexanes). The cooling bath was removed and the reaction mixture was warmed up slowly to ambient temperature over 1 h. The reaction was quenched by addition of sat. NH₄Cl (180 mL). Water (200 mL) was added and organic layer was separated. The aqueous layer was extracted again with DCM (300 mL). The combined organic layer was washed with water (3×400 mL), brine (150 mL), and dried over Na₂SO₄. Removal of solvent afforded a sticky brown residue.

The crude oil residue (contained trace of DCM) was stored overnight in the freezer. After overnight, some crystal solid was observed in the oil. The oil was dissolved in 500 ml hexanes at ambient temperature. The solution was stored in the freezer for 24 hours and more solid was formed. Solid was collected via filtration and rinsed with cold 10% DCM in hexanes (1 L) to remove most of the orange color. The solid (17) was dried under vacuum for 2 h and then air dried for 24 h. The solid weighed 21 g after dried at 50° C. under vacuum. The filtrate was concentrated and the residue was purified via column chromatography (10-70% ethyl acetate in hexanes) to afford an additional 37 g (combined yield of 97%) of 17 as a light orange solid.

Example 19-3

Preparation of 1-((2R,3S,4R,5R)-3,4-dihydroxy-5-(hydroxymethyl)-3-$^{13}$C-perdeuteriomethyltetrahydrofuran-2-yl)pyrimidine-2,4(1H,3H)-dione, 18

Magnesium (3.53 g, 147 mmol), washed with 5% aqueous hydrochloric acid and dried (50° C., 0.2 mm Hg, 24 h), was put into a two neck round bottomed flask equipped with a magnetic stirrer and a condensor. The flask was filled with argon gas and then anhydrous ether (80 mL) was added. To the magnesium in ether was added slowly perdeuterio-$^{13}$C methyl iodide (15.06 g, 110.3 mmol), which generated an exothermic reaction. After the reaction mixture was cooled down, the supernatant was transferred to a solution of dried compound 17 (50° C., 0.2 mm Hg, 15 h) (10.0 g, 20.63 mmol) in anhydrous THF (1 L) at −50° C. over 20 min. The temperature was allowed to rise to −40° C. and the mixture was stirred at between −40 to −25° C. for 4 h. Upon completion of reaction, the mixture was diluted with EtOAc (1 L) at −50° C. and then brine (300 mL) was added slowly. The organic layer was separated and then washed with sat'd ammonium chloride solution (300 mL×2) and dried with sodium sulfate. After filtration and concentration under reduced pressure, the residue was dissolved in MeOH (250 mL). Ammonium fluoride (12 g) and TBAF (400 mg) were added. The resulting mixture was stirred at 90° C. for 7 h and then concentrated with silica gel (20 g) under reduced pressure. After thorough vacuum drying, the obtained residue was purified by flash silica gel column chromatography (MeOH:CH₂Cl₂=1:20 to 1:10) give compound 18 (5 g, 46%) as a white solid. ¹H NMR (DMSO-d₆) δ (ppm) 11.26 (s, 1H, NH), 7.65 (d, 1H, J=8.4 Hz, H-6), 5.77 (d, 1H, J=2.4 Hz, H-1'), 5.57 (d, 1H, J=8.0 Hz, H-5), 5.46 (d, 1H, J=5.2 Hz, HO-3'), 5.24 (d, 1H, J=2.4 Hz, HO-2'), 5.14 (t, 1H, J=5.6 Hz, HO-5'), 3.74-3.56 (m, 4H, H-3', 4', 5', 5").

Example 19-4

Preparation of O₂R,3R,4S,5R)-3-acetoxy-5-(2,4-dioxo-3,4-dihydropyrimidin-1(2H)-yl)-4-hydroxy-4-$^{13}$C-perdeuteriomethyltetrahydrofuran-2-yl)methyl acetate, 19

To a solution of compound 18 (5.00 g, 19.1 mmol) in anhydrous pyridine (100 mL) was added acetic anhydride (3 mL) at ambient temperature. The resulting mixture was stirred at ambient temperature for 15 h, diluted with EtOAc (250 mL), washed with water (50 mL×3), and dried with sodium sulfate. After filtration and concentration, the residue was purified by flash column chromatography (MeOH 0 to 5% in CH₂Cl₂) to give compound 19 (4.0 g, 68%) as a gray solid.

Example 19-5

Preparation of O₂R,3R,4R,5R)-3-acetoxy-5-(2,4-dioxo-3,4-dihydropyrimidin-1(2H)-yl)-4-fluoro-4-$^{13}$C-perdeuteriomethyltetrahydrofuran-2-yl)methyl acetate, 20

To a solution of compound 19 (2.33 g, 6.73 mmol) in anhydrous CH₂Cl₂ (60 mL) was added DAST (1.33 mL, 10.1 mmol) at −78° C. slowly. The resulting mixture was stirred for 30 min after exposed to ambient temperature. An additional two 2.33 g scale reactions and one 1.00 g scale reaction were conducted exactly the same way. All four reaction mixtures were combined, diluted with CH₂Cl₂ (300 mL), and washed with ice-water (100 mL×2) and then cold aqueous NaHCO₃ solution (100 mL×2). After drying, filtration, and concentration, the residue was purified by flash silica gel column chromatography (EtOAc 0% to 50% in hexanes, compound came out at around 48%) to give compound 20 (2.0 g, 24% from total 7.99 g of compound 19) as a white solid. ¹H NMR (CDCl₃) δ (ppm) 8.27 (s, 1H, NH), 7.55 (d, 1H, J=8.4 Hz, H-6), 6.17 (d, 1H, J=18.8 Hz, H-1'), 5.78 (dd, 1H, J=1.2, 8.4 Hz, H-5), 5.12 (dd, 1H, J=9.6, 21.6 Hz, H-3'), 4.40-4.31 (m, 3H, H-4', 5', 5"), 2.19 (s, 3H, CH₃), 2.15 (s, 3H, CH₃).

Example 19-6

Preparation of 1-((2R,3R,4R,5R)-3-fluoro-4-hydroxy-5-(hydroxymethyl)-3-$^{13}$C-perdeuteriomethyltetrahydrofuran-2-yl)pyrimidine-2,4(1H,3H)-dione, 21

To a solution of compound 20 (2 g, 5.74 mmol) in methanol (20 mL) was added n-butylamine (6 mL). The resulting mixture was stirred at rt for 15 h and concentrated with silica gel in vacuo. The obtained residue was purified by flash silica gel column chromatography (MeOH 0 to 10% in CH₂Cl₂) to give compound 21 (1.3 g, 85%) as a white solid. ¹H NMR (CD₃OD) δ (ppm) 8.08 (d, 1H, J=8.0 Hz, H-6), 6.13 (d, 1H, J=18.4 Hz, H-1'), 5.70 (d, 1H, J=8.0 Hz, H-5), 3.99 (d, 1H, J=13.6 Hz, H-5'), 3.97-3.91 (m, 2H, H-3', 4'), 3.80 (dd, 1H, J=2.0, 12.8 Hz, H-5"), ESMS (M+1) estimated 265, observed 265.

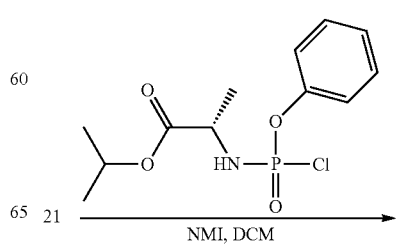

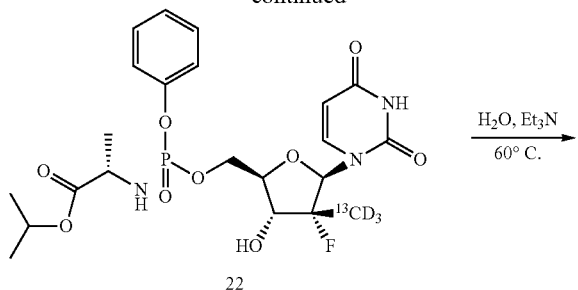

Example 19-7

Preparation of (S)-Isopropyl 2-(((((2R,3R,4R,5R)-5-(2,4-dioxo-3,4-dihydropyrimidin-1(2H)-yl)-4-fluoro-3-hydroxy-4-$^{13}$C-perdeuteriomethyltetrahydrofuran-2-yl)methoxy)(phenoxy)phosphorylamino)propanoate, 22

To a solution of the unprotected nucleoside 21 (207 mg, 0.783 mmol) and N-methylimidazole (0.4 ml, 5 mmol) in THF (4 mL) was added the pre-made phosphorochloridate in THF (1.0 M, 2.35 ml, 2.35 mmol) at 0° C. dropwise. The reaction was slowly warmed to ambient temperature over 1 h and then water (1 mL) and EtOAc (5 mL) were added. The organic solution was washed with sat. aq. mono basic sodium citrate (2×2 ml), sat. aq. $NaHCO_3$ (1×2 ml), dried ($MgSO_4$) and concentrated under reduced pressure. The crude was purified by silica column chromatography using 0 to 5% $^i$PrOH in $CH_2Cl_2$ as eluents to give the phosphoramidate, 22 (216 mg, 52%, 1:1 mixture of P-diastereomers) as a white solid: $^1$H NMR (400 MHz, DMSO-$d_6$) δ 11.54 (s, 1H), 7.56 (d, J=6.8 Hz, 1H), 7.40-7.35 (m, 2H), 7.23-7.18 (m, 3H), 6.14-5.96 (m, 2H), 5.89 (dd, J=5.6, 25.6 Hz, 1H), 5.55 (t, J=8.4 Hz, 1H), 4.85 (dq, J=1.6, 6.0 Hz, 1H), 4.44-4.32 (m, 1H), 4.25 (m, 1H), 4.06-3.98 (m, 1H), 3.86-3.70 (m, 2H), 1.30-1.08 (m, 9H); $^{31}$P NMR (162 MHz, DMSO-$d_6$) δ 4.90, 4.77; LRMS (ESI) [M+H]$^+$ calculated for $C_{21}^{13}CH_{27}D_3FN_3O_9P$, 534.5. found 534.4.

Example 19-8

Preparation of (2S)-2-(((((2R,3R,4R,5R)-5-(2,4-dioxo-3,4-dihydropyrimidin-1(2H)-yl)-4-fluoro-3-hydroxy-4-$^{13}$C-perdeuteriomethyltetrahydrofuran-2-yl)methoxy)(hydroxy)phosphoryl)amino)propanoic acid, 23

Phosphoramidate 22 (147 mg, 0.276 mmol) was suspended in triethylamine (2 mL) and water (0.5 mL), and heated at 60° C. for 30 h. Then the volatile components were evaporated under reduced pressure. The crude was purified by silica column chromatography by eluting with 50-70% $^i$PrOH in $CH_2Cl_2$ and then, 0 to 20% $NH_4OH$ in $^i$PrOH to give 23 as a white solid (95 mg, 83%): $^1$H NMR (400 MHz, DMSO-d6) δ 8.00 (d, J=8.4 Hz, 1H), 5.98 (d, J=19.2 Hz, 1H), 5.52 (d, J=8.4 Hz, 1H), 4.02-3.81 (m, 4H), 1.10 (d, J=6.8 Hz, 3H); $^{31}$P NMR (162 MHz, DMSO-d6) δ 8.12; LRMS (ESI) [M+H]$^+$ calculated for $C_{12}^{13}CH_{17}D_3FN_3O_9P$, 416.3. found 416.4.

Properties of Samples of $R_P$-4, 4, and $S_P$-4

Samples of $R_P$-4, 4, and $S_P$-4 were analyzed by X-Ray Powder Diffraction (XRPD), Nuclear Magnetic Resonance (NMR) spectrometry, Fourier Transform Infrared (FT-IR) spectroscopy, Differential Scanning calorimetry (DSC), Thermal Gravimetric Analysis (TGA), Gravimetric Vapor Sorption (GVS), Thermodynamic Aqueous Solubility, and High Performance Liquid Chromatography (HPLC).

Example 20

X-Ray Powder Diffraction

Samples of $R_P$-4, 4, and $S_P$-4 were analyzed by X-Ray Powder Diffraction (XRPD) under the following regimen.

a. Bruker AXS/Siemens D5000

X-Ray Powder Diffraction patterns were collected on a Siemens D5000 diffractometer using Cu Kα radiation (40 kV, 40 mA), θ-θ goniometer, divergence of V20 and receiving slits, a graphite secondary monochromator and a scintillation counter. The instrument is performance checked using a certified Corundum standard (NIST 1976). The software used for data collection was Diffrac Plus XRPD Commander v2.3.1 and the data were analyzed and presented using Diffrac Plus EVA v 11.0.0.2 or v 13.0.0.2.

Ambient Conditions

Samples run under ambient conditions were prepared as flat plate specimens using powder as received. Approximately 35 mg of the sample was gently packed into a cavity cut into polished, zero-background (510) silicon wafer. The sample was rotated in its own plane during analysis. The details of the data collection are: angular range: 2 to 42° 2θ; step size: 0.05° 2θ; and collection time: 4 s·step$^{-1}$.

b. Bruker AXS C2 GADDS

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Gael multilayer mirror coupled with a pinhole collimator of 0.3 mm.

The beam divergence, i.e. the effective size of the X-ray beam on the sample, was approximately 4 mm. A θ-θ continuous scan mode was employed with a sample—detector distance of 20 cm which gives an effective 2θ range of 3.2°-29.7°. Typically the sample would be exposed to the X-ray beam for 120 seconds. The software used for data collection was GADDS for WNT 4.1.16 and the data were analyzed and presented using Diffrac Plus EVA v 9.0.0.2 or v 13.0.0.2.

Ambient Conditions

Samples run under ambient conditions were prepared as flat plate specimens using powder as received without grinding. Approximately 1-2 mg of the sample was lightly pressed on a glass slide to obtain a flat surface.

X-Ray Powder Diffraction (XRPD)

4 was found by XRPD to be amorphous (see FIG. 1). High resolution XRPD analysis of $R_P$-4 prepared according to Example 3 confirmed a crystalline solid exhibiting a different powder pattern to that of $S_P$-4 (prepared according to Example 4, Method 4), which was also confirmed to be a crystalline solid. The XRPD results table for $R_P$-4 and $S_P$-4 are shown in Table 1 with all peaks exhibiting an intensity of ≤5% ($R_P$-4) and ≤3% ($S_P$-4) excluded.

TABLE 1

XRPD Data for $R_P$-4 and $S_P$-4.

| XRPD data for $R_P$-4 | | XRPD data for $S_P$-4(Form 1) | |
|---|---|---|---|
| Angle 2-Theta ° | Intensity % | Angle 2-Theta ° | Intensity % |
| 6.616 | 51.1 | 4.900 | 6.8 |
| 7.106 | 40.5 | 5.190 | 19.8 |
| 8.980 | 30.0 | 7.501 | 100.0 |
| 11.020 | 21.7 | 8.355 | 4.1 |
| 11.559 | 77.1 | 8.965 | 7.7 |
| 11.950 | 12.8 | 9.619 | 21.2 |
| 13.023 | 5.2 | 10.145 | 3.6 |
| 14.099 | 6.2 | 14.393 | 4.9 |
| 15.121 | 5.7 | 16.300 | 7.0 |
| 15.624 | 5.4 | 16.688 | 10.6 |
| 16.003 | 17.8 | 17.408 | 5.5 |
| 17.882 | 100.0 | 17.820 | 8.2 |
| 18.567 | 8.8 | 18.262 | 31.5 |
| 19.564 | 22.7 | 18.600 | 6.3 |
| 20.280 | 5.6 | 18.900 | 7.3 |
| 20.728 | 42.5 | 19.150 | 6.1 |
| 21.047 | 19.9 | 19.696 | 4.8 |
| 21.671 | 22.0 | 20.398 | 4.4 |
| 21.943 | 23.3 | 20.710 | 6.9 |
| 22.214 | 18.9 | 21.950 | 6.1 |
| 23.074 | 28.5 | 22.175 | 12.2 |
| 24.145 | 30.3 | 22.511 | 5.6 |
| 24.355 | 39.1 | 22.924 | 3.1 |
| 25.366 | 7.6 | 23.360 | 6.5 |
| 26.146 | 36.2 | 23.538 | 7.1 |
| 27.000 | 9.0 | 23.910 | 7.4 |
| 27.313 | 15.6 | 24.873 | 3.7 |
| 27.677 | 22.7 | 25.123 | 4.9 |
| 28.219 | 12.8 | 25.649 | 4.2 |
| 28.661 | 6.2 | 26.748 | 5.2 |
| 29.450 | 6.8 | 27.339 | 3.7 |
| 29.735 | 9.4 | 27.646 | 3.5 |
| 31.372 | 8.2 | 28.066 | 3.1 |
| 31.967 | 10.9 | 29.050 | 3.0 |
| 32.295 | 6.4 | 29.541 | 3.6 |
| 33.001 | 11.4 | 30.178 | 3.8 |
| 33.774 | 11.8 | 31.648 | 3.1 |
| 34.385 | 6.6 | 32.721 | 3.5 |
| 34.734 | 6.5 | 33.154 | 3.0 |
| 35.600 | 7.3 | 33.923 | 3.5 |
| 35.965 | 13.1 | 34.341 | 3.1 |
| 36.409 | 14.7 | 35.465 | 3.5 |
| 36.880 | 7.0 | 36.923 | 3.1 |
| 37.509 | 5.9 | 37.760 | 3.4 |
| 37.870 | 6.0 | 38.404 | 3.3 |
| 38.313 | 5.8 | 40.416 | 3.1 |
| 38.943 | 8.4 | | |
| 40.093 | 6.6 | | |
| 40.511 | 7.8 | | |
| 41.429 | 6.5 | | |

A sample of $S_P$-4 was ground with a pestle and mortar, and then successively passed through 500 and 250 μm sieves to yield the sample as a fine powder. This sample was reanalyzed by high resolution XRPD, confirming no form change had occurred.

Example 21

Crystallization Studies for $S_P$-4

Crystalline $S_P$-4 exhibits polymorphism. Thus, an aspect is directed to crystalline $S_P$-4 and its individual polymorphic forms. $S_P$-4 can exist in at least five polymorphic forms, designated as Forms 1-5. Furthermore, amorphous $S_P$-4 can also be prepared. A typical crystallization provides for dissolving about 100 mg of $S_P$-4 in an appropriate volume of crystallization solvent (acetonitrile (5 vol), chloroform (5 vol), n-butyl acetate (7 vol), dichloromethane (50 vol), anisole (7 vol), and 1:1 MTBE/heptane (50 vol)) and then allowing for evaporation of the solution at 5° C. Various crystalline forms were obtained, but each form, upon filtration and/or drying, afforded Form 1.

Figure 4:
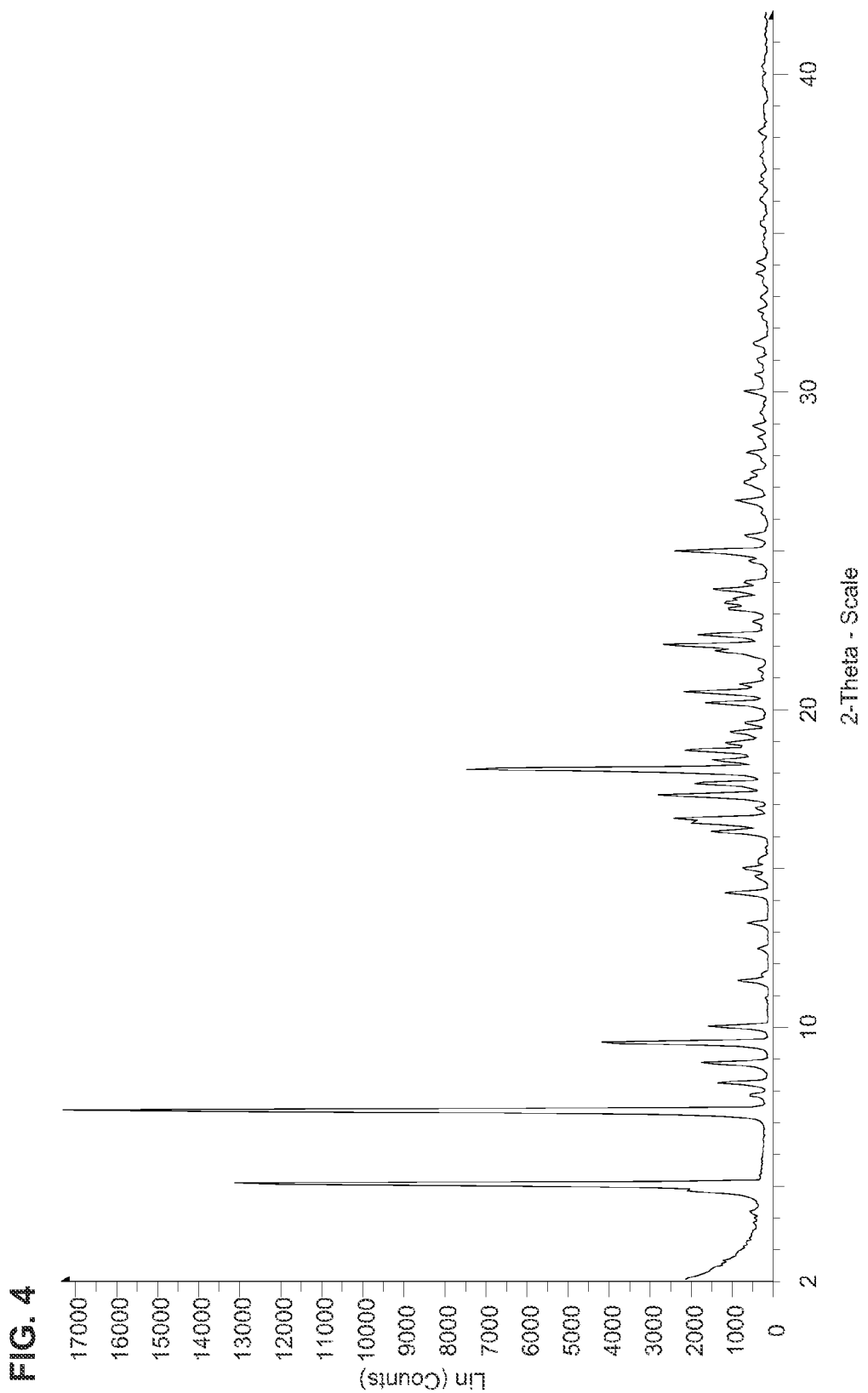
FIG. 4. High resolution XRD diffractogram of $S_P$-4 (Form 1).

Forms 1, 2 and 3 are a non-solvated form, 1:1 DCM solvate and 1:1 chloroform solvate, respectively, as was confirmed by singe crystal X-ray and XRPD analysis. Forms 4 and 5 were obtained from crystallization of $S_P$-4 from solutions of acetonitrile and anisole, respectively. Sufficient data could not be collected to determine whether Forms 4 and 5 are unsolvated, hydrated or solvated since single crystals of sufficient quality were not obtained. Forms 4 and 5 transform to Form 1 on filtration. Two additional crystalline forms are obtained upon crystallization of $S_P$-4 from n-butyl acetate ("BuAc) and a solution containing methyl-$^t$butyl ether (MTBE) and heptane; upon filtration both of these crystalline forms convert to Form 1. Forms 2 and 3 also transform to Form 1 on isolation. Form 1 is a non-solvated form that exhibits a broad melting endotherm with an onset temperature of 94.3° C. and $\Delta H_{fus}$ of 24.0 kJ mol$^{-1}$. An additional XRPD pattern of $S_P$-4 Form 1 is depicted in FIG. 4.

Example 21-1

$S_P$-4 Form 1

A peak listing of $S_P$-4 Form 1 is presented in Table 2.

| Angle 2-Theta ° | Intensity % |
|---|---|
| 5.0 | 74.8 |
| 7.3 | 100.0 |
| 7.8 | 2.2 |
| 8.2 | 6.8 |
| 8.8 | 9.3 |
| 9.4 | 23.5 |
| 10.0 | 8.4 |
| 11.4 | 4.2 |
| 13.3 | 3.0 |
| 14.2 | 6.1 |
| 14.9 | 3.5 |
| 16.1 | 7.9 |
| 16.6 | 13.2 |
| 17.3 | 15.4 |
| 17.7 | 10.1 |
| 18.1 | 42.6 |
| 18.4 | 7.6 |
| 18.7 | 11.4 |
| 18.9 | 5.7 |
| 19.3 | 5.0 |
| 19.6 | 2.9 |
| 20.2 | 8.5 |
| 20.5 | 11.5 |
| 20.8 | 3.6 |
| 21.8 | 7.2 |
| 22.0 | 14.5 |
| 22.4 | 9.6 |
| 23.2 | 5.3 |
| 23.4 | 5.8 |
| 23.5 | 4.6 |
| 23.8 | 7.4 |
| 24.0 | 3.1 |
| 24.7 | 2.5 |
| 25.0 | 13.0 |
| 25.5 | 3.1 |

-continued

| Angle 2-Theta ° | Intensity % |
|---|---|
| 26.6 | 4.5 |
| 27.2 | 3.2 |
| 27.5 | 2.2 |
| 28.1 | 2.9 |
| 30.0 | 3.2 |

Example 21-2

$S_P$-4 Form 2

Figure 5:
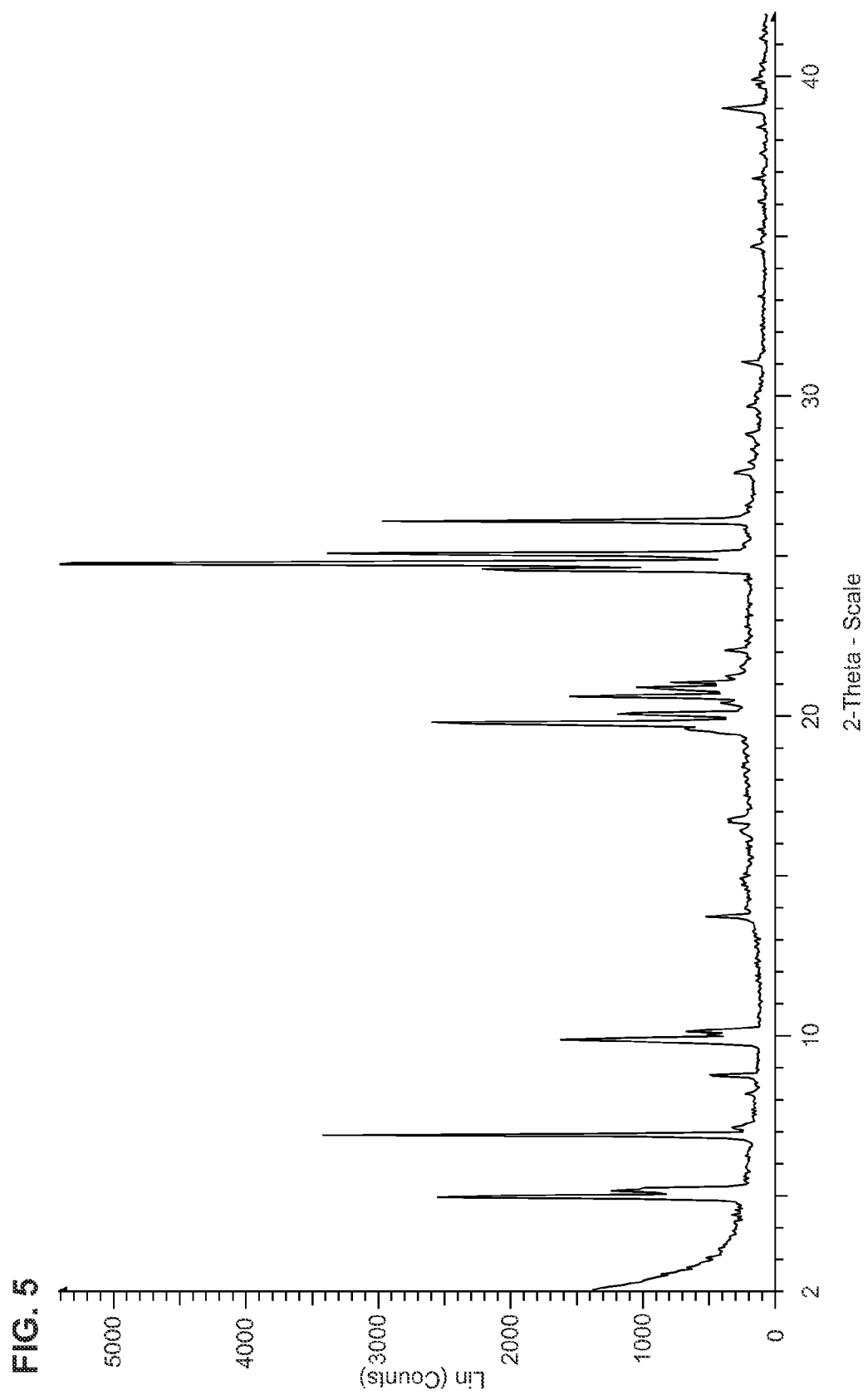
FIG. 5. High resolution XRD diffractogram of $S_P$-4.$CH_2Cl_2$ (Form 2).

An XRPD pattern of $S_P$-4 Form 2 is depicted in FIG. 5. A peak listing of $S_P$-4 Form 2 is presented in Table 3.

| Angle 2-Theta ° | Intensity % |
|---|---|
| 4.9 | 44.1 |
| 5.1 | 19.1 |
| 6.9 | 62.1 |
| 8.7 | 6.8 |
| 9.8 | 28.6 |
| 10.1 | 10.4 |
| 13.7 | 7.0 |
| 16.7 | 3.1 |
| 19.5 | 8.9 |
| 19.8 | 45.5 |
| 20.1 | 18.6 |
| 20.4 | 3.6 |
| 20.6 | 25.6 |
| 20.9 | 15.9 |
| 21.1 | 10.9 |
| 22.1 | 3.4 |
| 24.6 | 38.7 |
| 24.7 | 100.0 |
| 25.1 | 61.2 |
| 26.1 | 53.3 |
| 39.0 | 6.3 |

Example 21-3

$S_P$-4 Form 3

Figure 6:
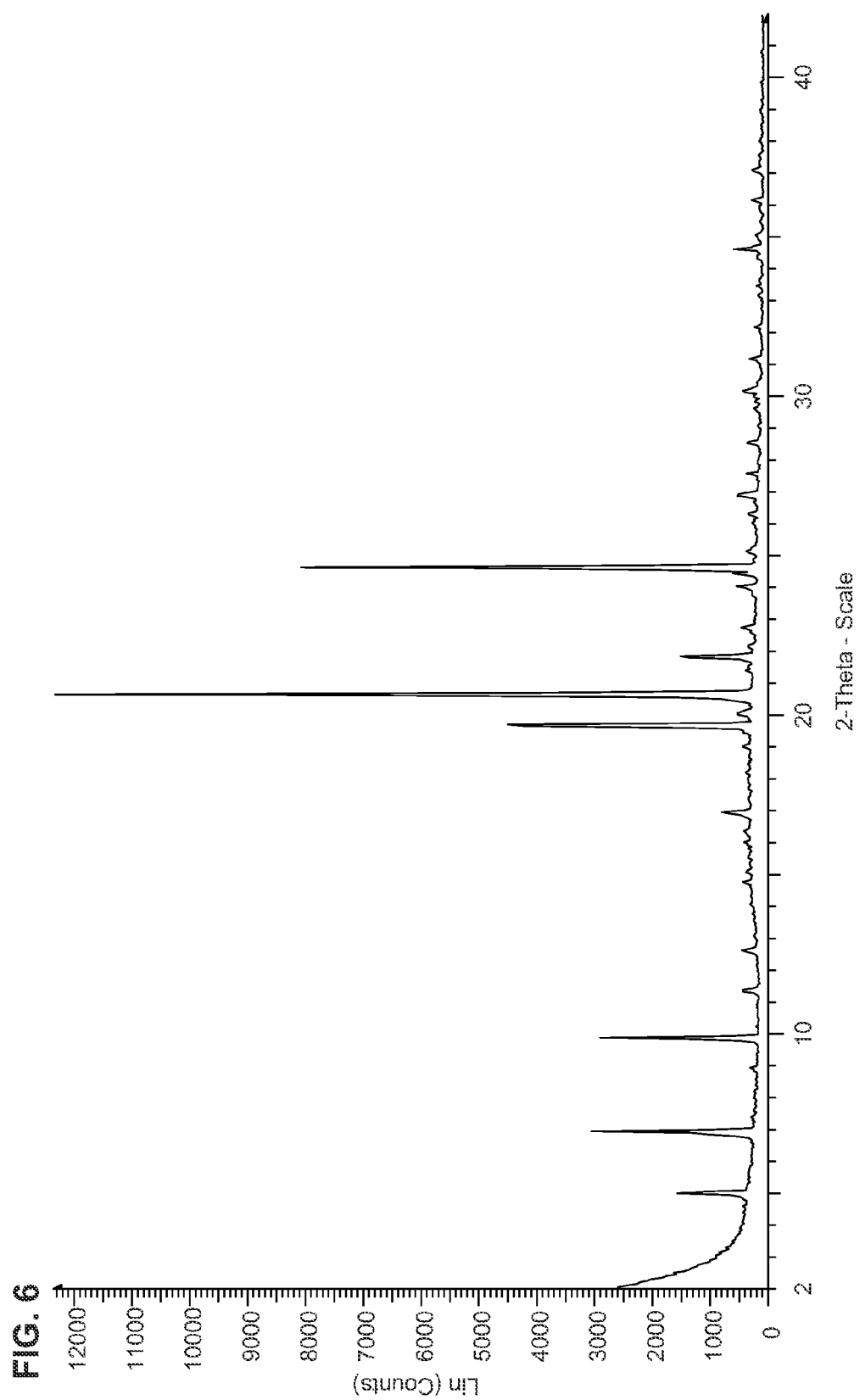
FIG. 6. High resolution XRD diffractogram of $S_P$-4.$CHCl_3$ (Form 3).

An XRPD pattern of $S_P$-4 Form 3 is depicted in FIG. 6. A peak listing of $S_P$-4 Form 3 is presented in Table 4.

| Angle 2-Theta ° | Intensity % |
|---|---|
| 5.0 | 10.0 |
| 6.9 | 23.3 |
| 9.8 | 22.6 |
| 19.7 | 34.8 |
| 20.6 | 100.0 |
| 21.8 | 10.5 |
| 24.6 | 65.3 |
| 34.7 | 4.1 |

Example 21-4

$S_P$-5 Form 4

An XRPD pattern of $S_P$-4 Form 4 is depicted in FIG. 7. A peak listing of $S_P$-4 Form 4 is presented in Table 5.

| Angle 2-Theta ° | Intensity % |
|---|---|
| 5.0 | 29.8 |
| 6.8 | 100.0 |
| 8.2 | 4.8 |
| 8.7 | 5.2 |
| 9.9 | 3.8 |
| 13.7 | 1.7 |
| 14.9 | 4.8 |
| 19.9 | 22.5 |
| 20.4 | 2.1 |
| 20.6 | 20.0 |
| 20.9 | 20.0 |
| 24.7 | 3.4 |
| 24.9 | 29.9 |
| 25.1 | 1.5 |
| 36.8 | 3.1 |

Example 21-5

$S_P$-4 Form 5

Figure 8:
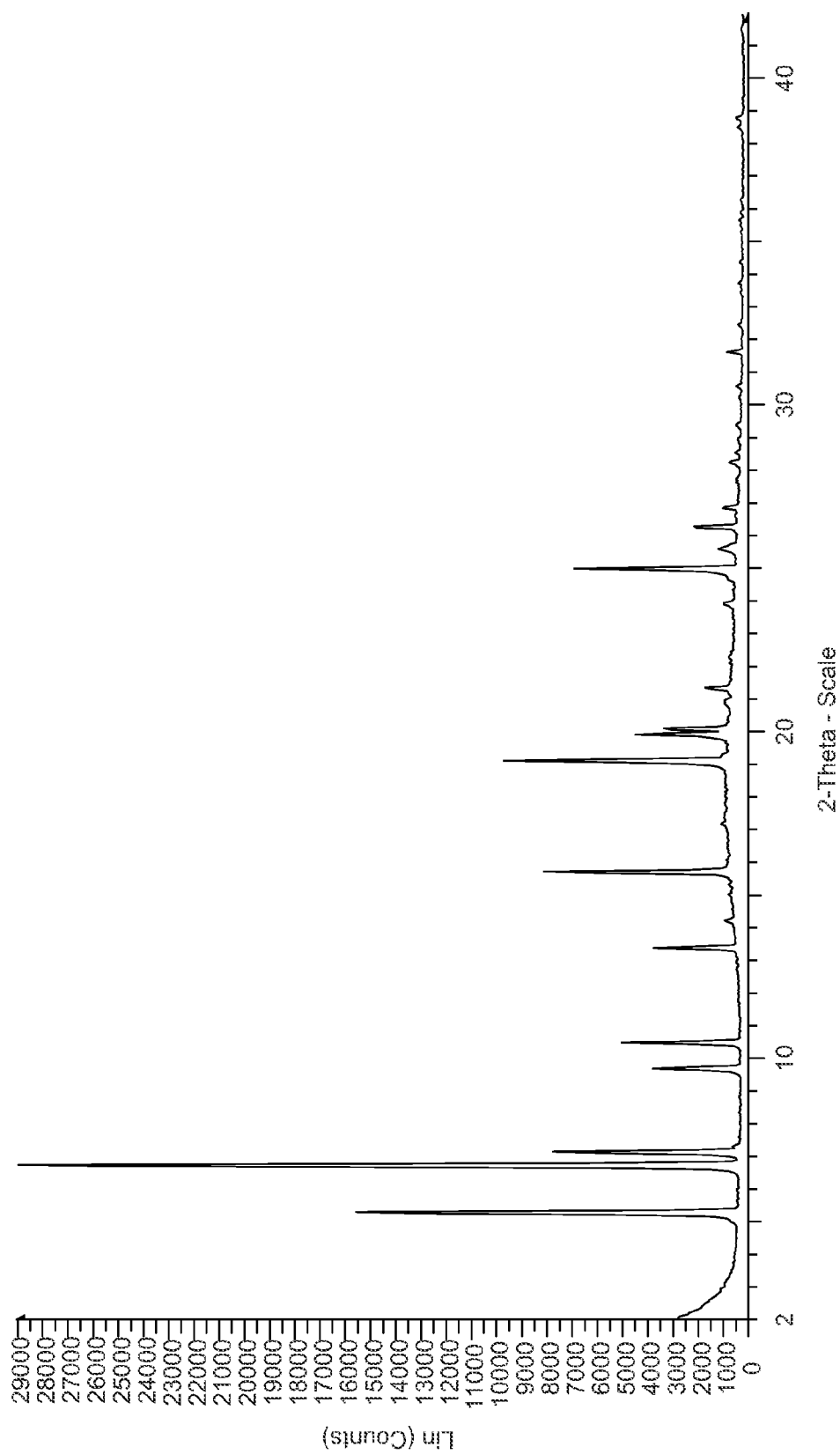
FIG. 8. High resolution XRD diffractogram of $S_P$-4 (Form 5).

An XRPD pattern of $S_P$-4 Form 5 is depicted in FIG. 8. A peak listing of $S_P$-4 Form 5 is presented in Table 6.

| Angle 2-Theta ° | Intensity % |
|---|---|
| 5.2 | 52.9 |
| 6.6 | 100.0 |
| 7.1 | 25.9 |
| 9.7 | 12.1 |
| 10.4 | 16.4 |
| 13.4 | 11.4 |
| 15.7 | 25.8 |
| 19.1 | 31.1 |
| 19.9 | 12.9 |
| 20.0 | 9.0 |
| 21.3 | 3.5 |
| 25.0 | 22.3 |
| 25.6 | 2.3 |
| 26.3 | 5.9 |
| 26.9 | 2.0 |
| 31.7 | 2.1 |

Example 21-6

$S_P$-4 (Amorphous)

Figure 9:
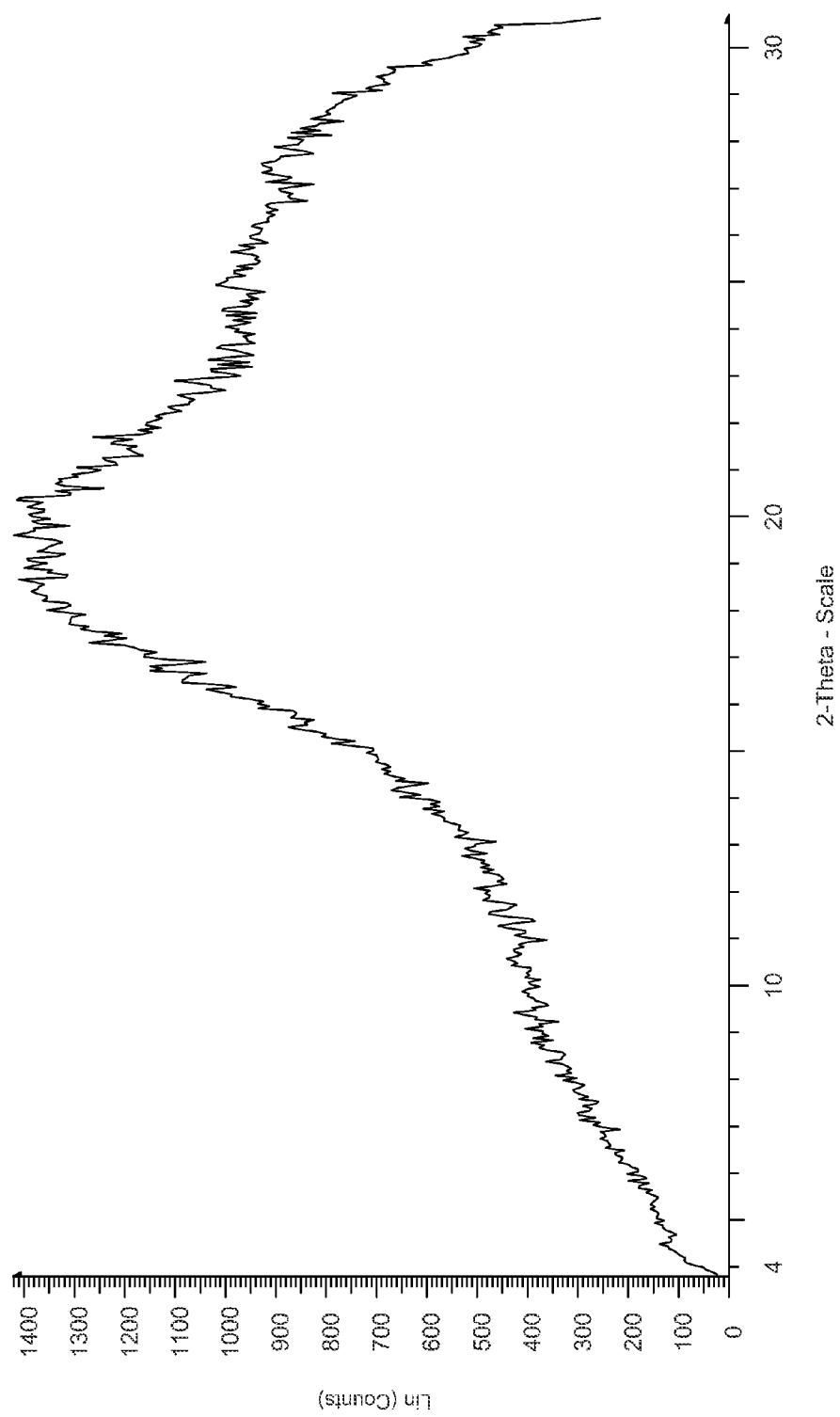
FIG. 9. High resolution XRD diffractogram of $S_P$-4 (amorphous).

An XRPD pattern for amorphous $S_P$-4 is depicted in FIG. 9.

Example 22

Single Crystal X-Ray Crystallography of $S_P$-4 and its Solvates

Example 22-1

Single Crystal X-Ray Crystallography of $S_P$-4 (Form 1)

Figure 10:
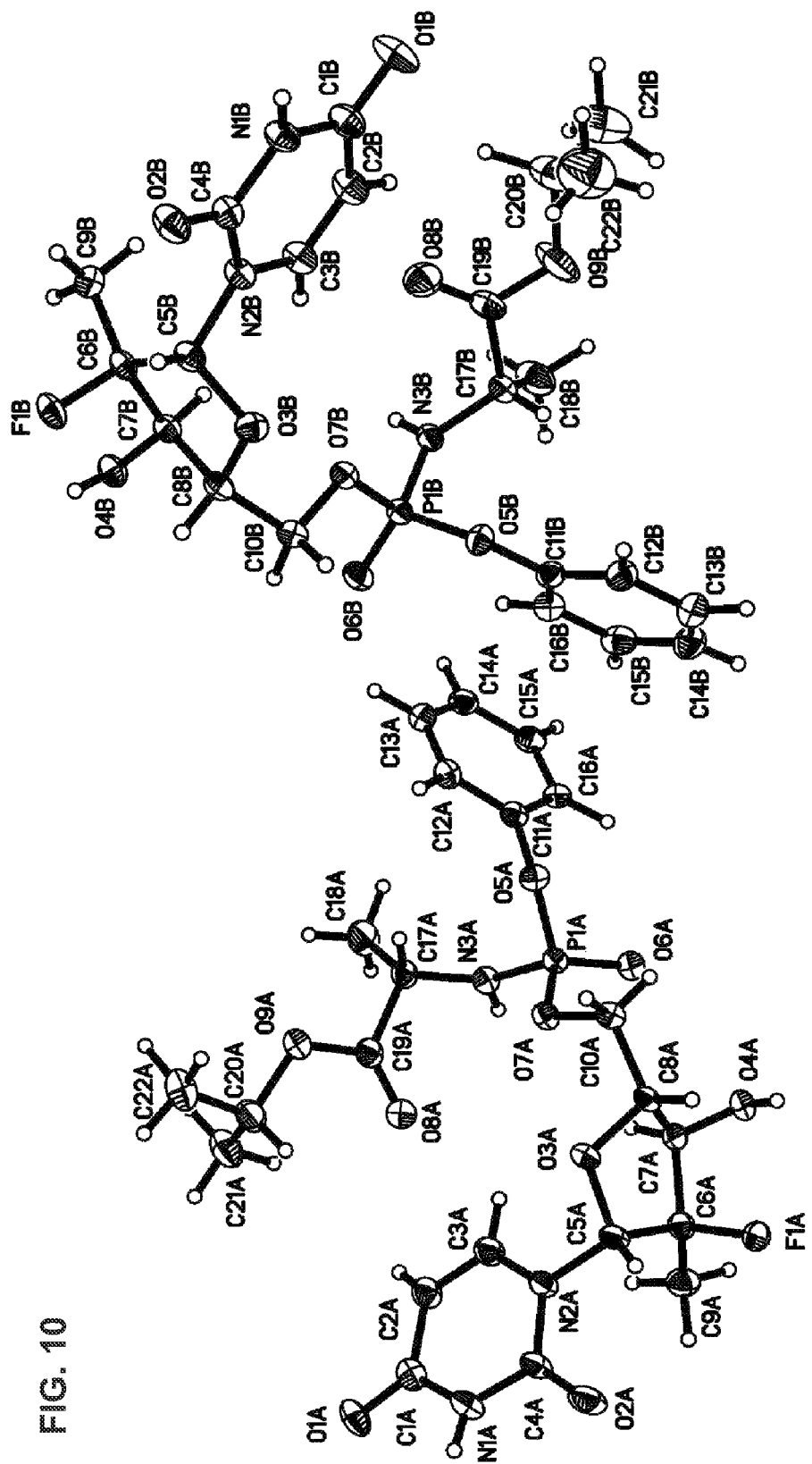
FIG. 10. X-Ray Crystal Structure for $S_P$-4 (Form 1).

FIG. 10 shows an X-ray crystal structure for $S_P$-4 Form 1. There, the figure shows a view of molecules of Form 1 from the crystal structure showing the numbering scheme employed. Anisotropic atomic displacement ellipsoids for the non-hydrogen atoms are shown at the 50% probability level. Hydrogen atoms are displayed with an arbitrarily small radius.

The structure solution was obtained by direct methods, full-matrix least-squares refinement on $F^2$ with weighting $w^{-1}=\sigma^2(F_o^2)+(0.0592P)^2+(0.6950P)$, where $P=(F_o^2+2F_c^2)/3$, anisotropic displacement parameters, empirical absorption correction using spherical harmonics, implemented in SCALE3 ABSPACK scaling algorithm. Final $wR^2=\{\Sigma[w(F_o^2-F_c^2)^2]/\Sigma[w(F_o^2)^2]^{1/2}\}=0.0871$ for all data, conventional $R_1=0.0329$ on F values of 7090 reflections with $F_o>4\sigma(F_o)$, S=1.016 for all data and 870 parameters. Final $\Delta/\sigma(\max)$ 0.001, $\Delta/\sigma(\text{mean})$, 0.000. Final difference map between +0.534 and −0.36 e Å$^{-3}$.

TABLE 7

| Single Crystal Parameters of Form 1 | | | | | |
|---|---|---|---|---|---|
| Molecular formula | $C_{22}H_{29}F_1N_3O_9P_1$ | | | | |
| Molecular weight | 529.45 | | | | |
| Crystal system | Monoclinic | | | | |
| Space group | $P2_1$ | a | 20.0898(5) Å | α | 90°, |
| | | b | 6.10290(10) Å | β | 112.290(3)°, |
| | | c | 23.0138(6) Å | γ | 90° |
| V | 2610.79(10) Å$^3$ | | | | |
| Z | 4 | | | | |
| $D_c$ | 1.347 g · cm$^{-1}$ | | | | |
| μ | 1.475 mm$^{-1}$ | | | | |
| Source, λ | Cu Kα, 1.54178 Å | | | | |
| F(000) | 1112 | | | | |
| T | 100(1) K | | | | |
| Crystal | Colorless plate, 0.12 × 0.09 × 0.03 mm | | | | |
| Data truncated to | 0.80 Å | | | | |
| $\theta_{max}$ | 74.48° | | | | |
| Completeness | 99.4% | | | | |
| Reflections | 14854 | | | | |
| Unique reflections | 7513 | | | | |
| $R_{int}$ | 0.0217 | | | | |

Example 22-2

Single Crystal X-Ray Crystallography of $S_P$-4 (Form 2)

Figure 11:
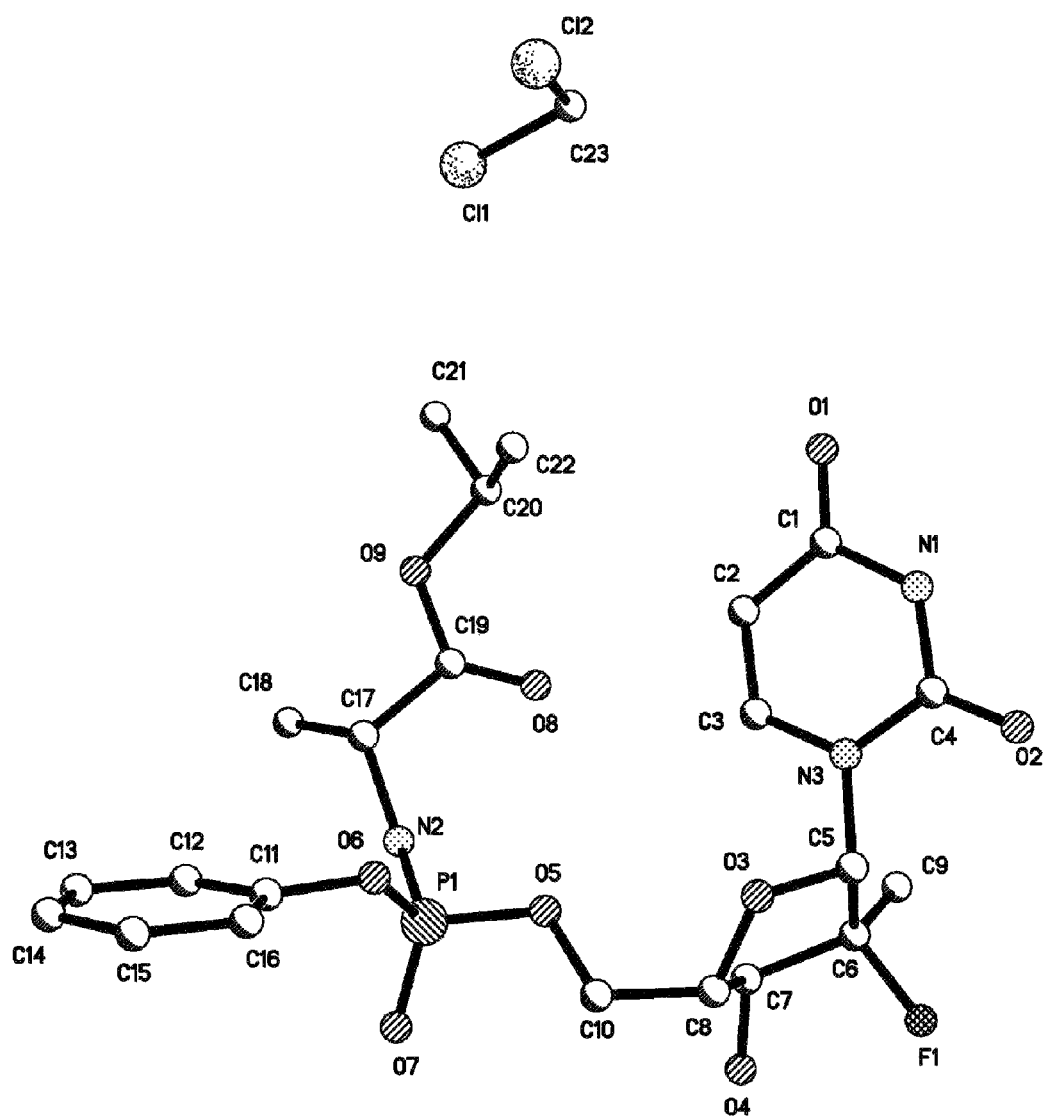
FIG. 11. X-Ray Crystal (Isotropic) Structure for $S_P$-4.$CH_2Cl_2$ (Form 2).

FIG. 11 shows an X-ray crystal structure for $S_P$-4 Form 2. There, this figure shows a view of molecules of Form 2 from the crystal structure showing the numbering scheme employed. The heteroatoms were resolved isotropically due to very weak data. Hydrogen atoms are not displayed.

The structure solution was obtained by direct methods, full-matrix least-squares refinement on $F^2$ with weighting $w^{-1}=\sigma^2(F_o^2)+(0.0975P)^2+(10.6969P)$, where $P=(F_o^2+2F_c^2)/3$, anisotropic displacement parameters, empirical absorption correction using spherical harmonics, implemented in SCALE3 ABSPACK scaling algorithm. Final $wR^2=\{\Sigma[w(F_o^2-F_c^2)^2]/\Sigma[w(F_o^2)^2]^{1/2}\}=0.1883$ for all data, conventional $R_1=0.0741$ on F values of 2525 reflections with $F_o>4\sigma(F_o)$, S=1.05 for all data and 158 parameters. Final $\Delta/\sigma(\max)$ 0.000, $\Delta/\sigma(\text{mean})$, 0.000. Final difference map between +1.388 and −0.967 e Å$^{-3}$.

TABLE 8

| Single Crystal Parameters of Form 2 | | | | | |
|---|---|---|---|---|---|
| Molecular formula | $C_{23}H_{31}Cl_2FN_3O_9P$ | | | | |
| Molecular weight | 614.38 | | | | |
| Crystal system | Monoclinic | | | | |
| Space group | $P2_1$ | a | 12.8315(3) Å | α | 90°, |
| | | b | 6.14530(10) Å | β | 91.752(2)°, |
| | | c | 17.6250(4) Å | γ | 90° |
| V | 1389.14(5) Å$^3$ | | | | |
| Z | 2 | | | | |
| $D_c$ | 1.469 g · cm$^{-1}$ | | | | |
| μ | 3.196 mm$^{-1}$ | | | | |
| Source, λ | Cu—K, 1.54178 Å | | | | |
| F(000) | 640 | | | | |
| T | 293(2) K | | | | |
| Data truncated to | 0.80 Å | | | | |
| $\theta_{max}$ | 62.23° | | | | |
| Completeness | 91.1% | | | | |
| Reflections | 3528 | | | | |
| Unique reflections | 2562 | | | | |
| $R_{int}$ | 0.0227 | | | | |

Example 22-3

Single Crystal X-Ray Crystallography of $S_P$-4 (Form 2)

Figure 12:
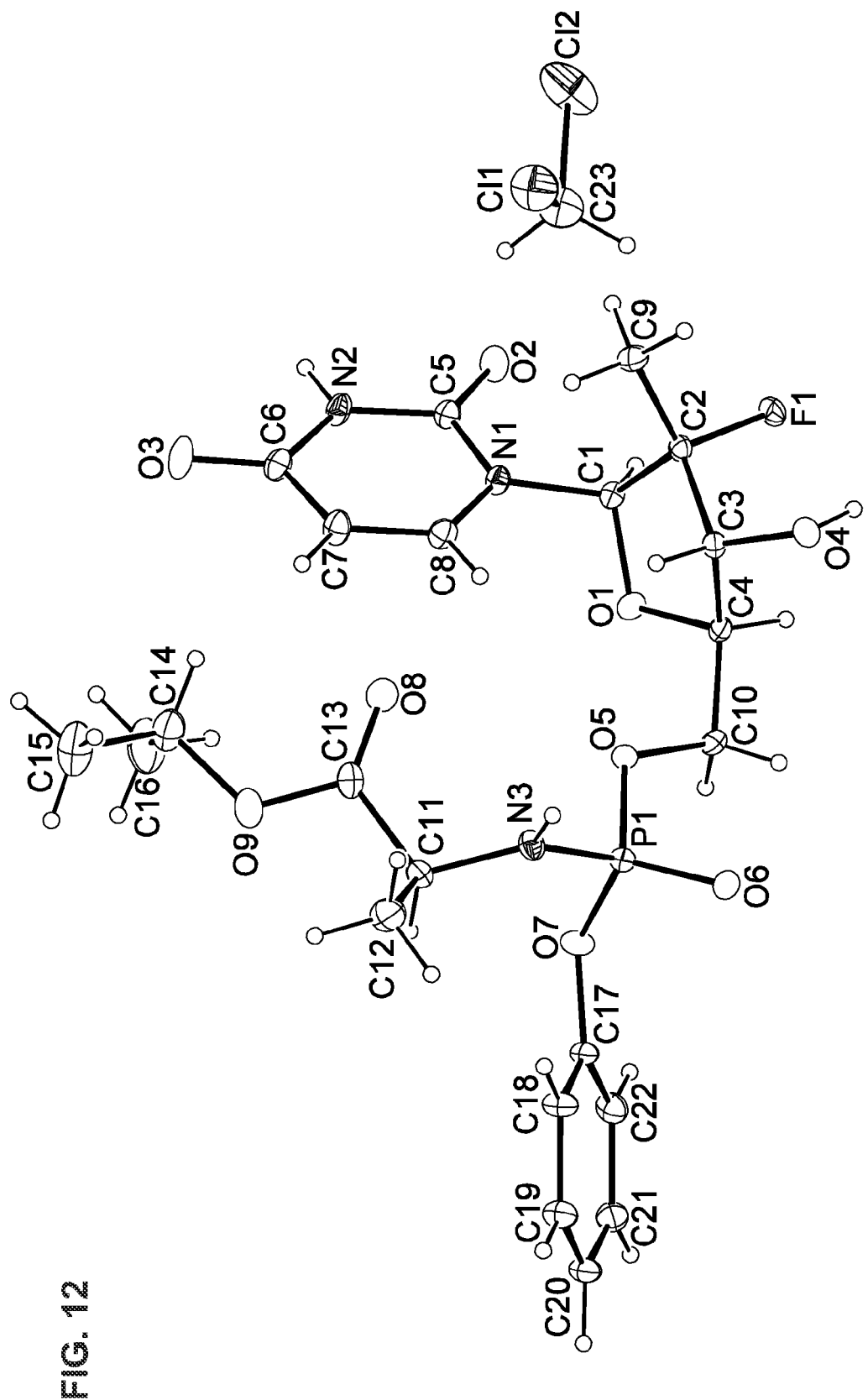
FIG. 12. X-Ray Crystal (Anisotropic) Structure for $S_P$-4.$CH_2Cl_2$ (Form 2).

FIG. 12 depicts an X-ray Crystal Structure (ORTEP—anisotropic) $S_P$-4 (Form 2). A crystal structure of the methylene chloride solvate of $S_P$-4 (Form 2), $C_{23}H_{31}N_3PO_9FCl_2$, yields a monoclinic space group $P2_1$ (systematic absences 0k0: k=odd) with a=12.8822(14) Å, b=6.1690(7) Å, c=17.733(2) Å, β=92.045(3)°, V=1408.4(3)Å$^3$, Z=2 and $d_{calc}=1.449$ g/cm$^3$. X-ray intensity data were collected on a Rigaku Mercury CCD area detector employing graphite-monochromated Mo—K$_\alpha$ radiation (λ=0.71073 Å) at a temperature of 143K. Preliminary indexing was performed from a series of twelve 0.5° rotation images with exposures of 30 seconds. A total of 648 rotation images were collected with a crystal to detector distance of 35 mm, a 2θ swing angle of −12°, rotation widths of 0.5° and exposures of 30 seconds: scan no. 1 was a ϕ-scan from 315° to 525° at ω=10° and χ=20°; scan no. 2 was an ω-scan from −20° to 5° at χ=−90° and ϕ=315°; scan no. 3 was an ω-scan from −20° to 4° at χ=−90° and ϕ=135°; scan no. 4 was an ω-scan from −20° to 5° at χ=−90° and ϕ=225°; scan no. 5 was an ω-scan from −20° to 20° at χ=−90° and ϕ=45°. Rotation images were processed using CrystalClear (CrystalClear: Rigaku Corporation, 1999), producing a listing of unaveraged $F^2$ and $\sigma(F^2)$ values which were then passed to the CrystalStructure (CrystalStructure: Crystal Structure Analysis Package, Rigaku Corp. Rigaku/MSC (2002)) program package for further processing and structure solution on a Dell Pentium III computer. A total of 7707 reflections were measured over the ranges 5.48≤2θ≤50.04°, −14≤h≤15, −7≤k≤6, −19≤l≤21 yielding 4253 unique reflections ($R_{int}$=0.0180). The intensity data were corrected for Lorentz and polarization effects and for absorption using REQAB (minimum and maximum transmission 0.824, 1.000).

The structure was solved by direct methods (SIR97, SIR97: Altomare, A., M. Burla, M. Camalli, G. Cascarano, C. Giacovazzo, A. Guagliardi, A. Moliterni, G. Polidori & R. Spagna (1999). *J. Appl. Cryst.*, 32, 115-119). Refinement was by full-matrix least squares based on $F^2$ using SHELXL-97 (SHELXL-97: Sheldrick, G. M. (2008) *Acta Cryst.*, A64, 112-122). All reflections were used during refinement. The weighting scheme used was $w=1/[\sigma^2(F_o^2)+0.0472P^2+0.4960P]$ where $P=(F_o^2+2F)/3$. Non-hydrogen atoms were refined anisotropically and hydrogen atoms were refined using a "riding" model. Refinement converged to $R_1=0.0328$ and $wR_2=0.0817$ for 4046 reflections for which $F>4\sigma(F)$ and $R_1=0.0348$, $wR_2=0.0838$ and GOF=1.056 for all 4253 unique, non-zero reflections and 358 variables ($R_1=\Sigma||F_o|-|F_c||/\Sigma|F_o|$; $wR_2=\{\Sigma w(F_o^2-F_c^2)^2/\Sigma w(F_o^2)^2\}^{1/2}$;

GOF=$\{\Sigma w(F_o^2-F_c^2)^2/(n-p)\}^{1/2}$; where n=the number of reflections and p=the number of parameters refined). The maximum $\Delta/\alpha$ in the final cycle of least squares was 0.000 and the two most prominent peaks in the final difference Fourier were +0.312 and −0.389 e/Å$^3$. The Flack absolute structure parameter refined to −0.06(6) thus corroborating the stereochemistry of the title compound.

Table 1 lists cell information, data collection parameters, and refinement data. Final positional and equivalent isotropic thermal parameters are given in Table 2. Anisotropic thermal parameters are in Table 3. ("ORTEP-II: A Fortran Thermal Ellipsoid Plot Program for Crystal Structure Illustrations". C. K. Johnson (1976) ORNL-5138.) representation of the molecule with 30% probability thermal ellipsoids displayed.

the non-hydrogen atoms are shown at the 50% probability level. Hydrogen atoms are displayed with an arbitrarily small radius.

The structure solution was obtained by direct methods, full-matrix least-squares refinement on F$^2$ with weighting $w^{-1}=\sigma^2(F_o^2)+(0.0512P)^2+(0.6810P)$, where $P=(F_o^2+2F_c^2)/3$, anisotropic displacement parameters, empirical absorption correction using spherical harmonics, implemented in SCALE3 ABSPACK scaling algorithm. Final $wR^2=\{\Sigma[w(F_o^2-F_c^2)^2]/\Sigma[w(F_o^2)^2]^{1/2}\}=0.0796$ for all data, conventional $R_1=0.0294$ on F values of 2486 reflections with $F_o>4\sigma(F_o)$, S=1.068 for all data and 377 parameters. Final $\Delta/\sigma(max)$ 0.001, $\Delta/\sigma(mean)$, 0.000. Final difference map between +0.211 and −0.334 e Å$^{-3}$.

TABLE 9

Summary of Structure Determination of Compound S$_P$-4•CH$_2$Cl$_2$.

| | |
|---|---|
| Formula: | C$_{23}$H$_{31}$N$_3$PO$_9$FCl$_2$ |
| Formula weight: | 614.38 |
| Crystal class: | monoclinic |
| Space group: | P2$_1$ (#4) |
| Z | 2 |
| Cell constants: | |
| a | 12.8822(14) Å |
| b | 6.1690(7) Å |
| c | 17.733(2) Å |
| β | 92.045(3)° |
| V | 1408.4(3) Å$^3$ |
| μ | 3.48 cm$^{-1}$ |
| crystal size, mm | 0.42 × 0.12 × 0.10 |
| D$_{calc}$ | 1.449 g/cm$^3$ |
| F(000) | 640 |
| Radiation: | Mo—K$_\alpha$($\lambda$ = 0.71073 Å) |
| 2θ range | 5.48-50.04° |
| hkl collected: | −14 ≤ h ≤ 15; −7 ≤ k ≤ 6; −19 ≤ l ≤ 21 |
| No. reflections measured: | 7707 |
| No. unique reflections: | 4253 (R$_{int}$ = 0.0180) |
| No. observed reflections | 4046 (F > 4σ) |
| No. reflections used in refinement | 4253 |
| No. parameters | 1358 |
| R indices (F > 4σ) | R$_1$ = 0.0328 |
| | wR$_2$ = 0.0817 |
| R indices (all data) | R$_1$ = 0.0348 |
| | wR$_2$ = 0.0838 |
| GOF: | 1.056 |
| Final Difference Peaks, e/Å$^3$ | +0.312, −0.389 |

Example 22-4

Single Crystal X-Ray Crystallography of S$_P$-4 (Form 3)

Figure 13:
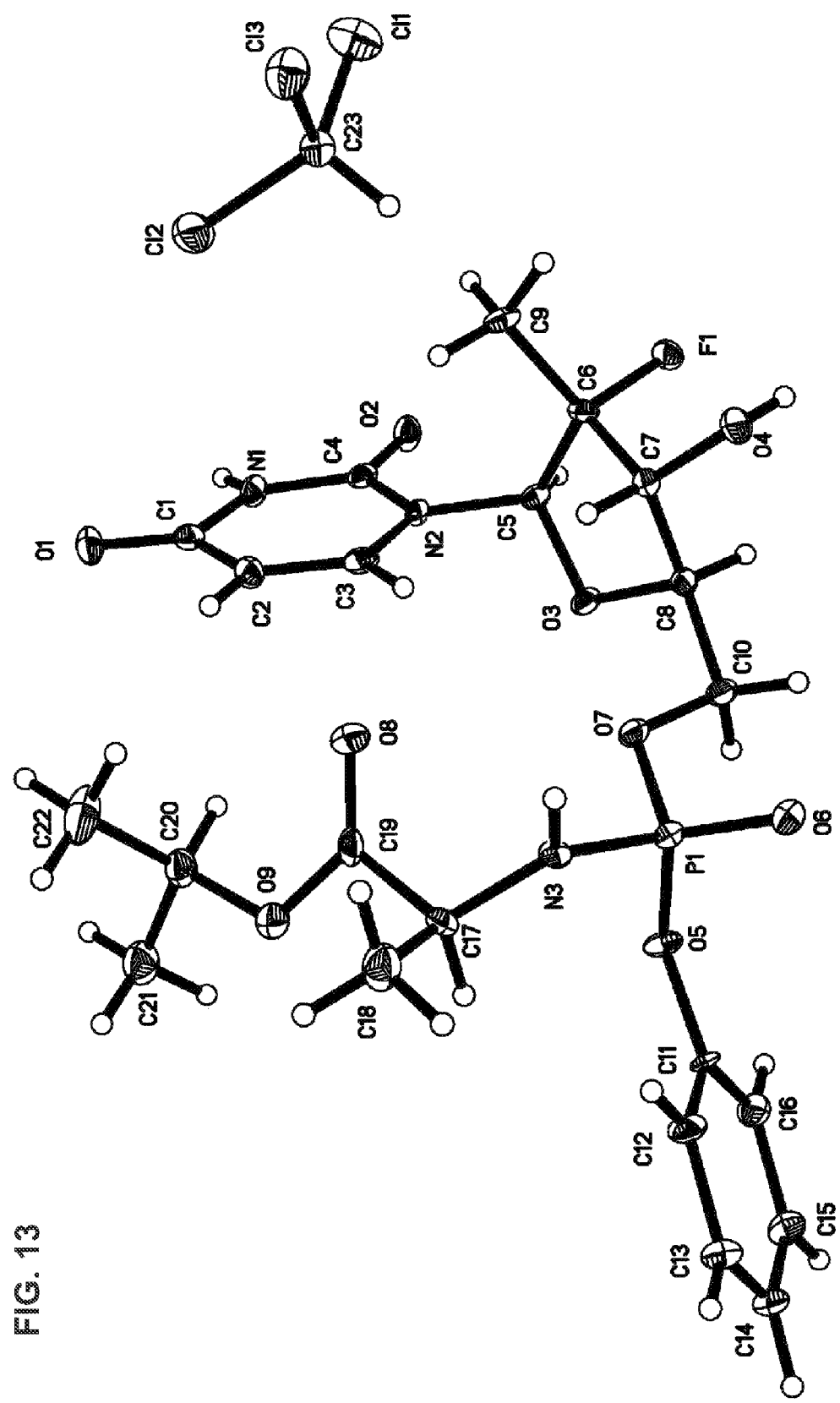
FIG. 13. X-Ray Crystal Structure for $S_P$-4.$CHCl_3$ (Form 3).

FIG. 13 shows an X-ray crystal structure for S$_P$-4 Form 3. There, this figure shows a view of molecules of Form 3 from the crystal structure showing the numbering scheme employed. Anisotropic atomic displacement ellipsoids for

TABLE 10

Single Crystal Parameters of Form 3

| | | | | |
|---|---|---|---|---|
| Molecular formula | C$_{23}$H$_{30}$Cl$_3$F$_1$N$_3$O$_9$P$_1$ | | | |
| Molecular weight | 648.82 | | | |
| Crystal system | Monoclinic | | | |
| Space group | P2$_1$ | a 12.9257(4) Å, | α | 90°, |
| | | b 6.18080(10) Å, | β | 96.399(2)°, |
| | | c 18.0134(4) Å, | γ | 90° |
| V | 1430.15(6) Å$^3$ | | | |
| Z | 2 | | | |
| D$_c$ | 1.507 g · cm$^{-1}$ | | | |
| μ | 3.977 mm$^{-1}$ | | | |
| Source, λ | Cu Kα, 1.54178 Å | | | |
| F(000) | 672 | | | |
| T | 100(1) K | | | |
| Crystal | Colorless needle, 0.22 × 0.03 × 0.02 mm | | | |
| Data truncated to | 0.80 Å | | | |
| θ$_{max}$ | 74.41° | | | |
| Completeness | 69.1% | | | |
| Reflections | 3062 | | | |
| Unique reflections | 2607 | | | |
| R$_{int}$ | 0.0198 | | | |

Example 23

Stability at Elevated Temperatures and Relative Humidity

A sample of R$_P$-4 was stored in a humidity chamber at 40° C. and 75% relative humidity for one week, and the sample was reanalyzed by XRPD. The powder pattern obtained for R$_P$-4 showed no substantial change during the course of the experiment, meaning that no change in solid form was observed. This should be contrasted to a sample of 4, which deliquesced within about 16 hours upon storage at 40° C. and 75% relative humidity. Indeed, an illustration of the deliquescent nature of 4 is illustrated by the following. A sample of 4 was passed through a 250 μm sieve then samples were stored at 40° C./75% RH and 25° C./53% relative humidity and visual observations were taken at regular intervals. The results are given in Table 4.

TABLE 11

Stability of 4 to elevated relative humidity.

| Conditions | t = 1.5 h | t = 4.5 h | t = 6.5 h | t = 8.5 h | t = 73 h |
|---|---|---|---|---|---|
| 40° C./75% RH | Deliquescence | — | — | — | — |
| 25° C./53% RH | No deliquescence | Sticky solid | Partial deliquescence | Almost complete deliquescence | Deliquescence |

Upon storage at 40° C. and 75% relative humidity a sample of $S_P$-4 deliquesced inside 16 hours. For instance, a sample of $S_P$-4 was ground with a pestle and mortar, and then successively passed through 500 and 250 µm sieves to yield the sample as a fine powder. Samples of this material were stored at 40° C. and 75% relative humidity and 25° C. and 53% RH and visual observations were taken at regular intervals. The results are given in Table 5.

TABLE 12

Stability of $S_P$-4 to elevated relative humidity.

| Conditions | t = 1.5 h | t = 4.5 h | t = 104 h |
|---|---|---|---|
| 40° C./75% RH | No deliquescence | Deliquescence | — |
| 25° C./53% RH | No deliquescence | No deliquescence | No deliquescence |

XRPD analysis of the sample after storage at 25° C. and 53% RH for 104 hours showed no significant changes in the diffractograms produced indicating that no form change had occurred.

Example 24

Fourier Transform—Infrared (FT-IR) Spectrometry

Data were collected on a Perkin-Elmer Spectrum One fitted with a universal Attenuated Total Reflectance (ATR) sampling accessory. The data were collected and analyzed using Spectrum v5.0.1 software.

Figure 14:
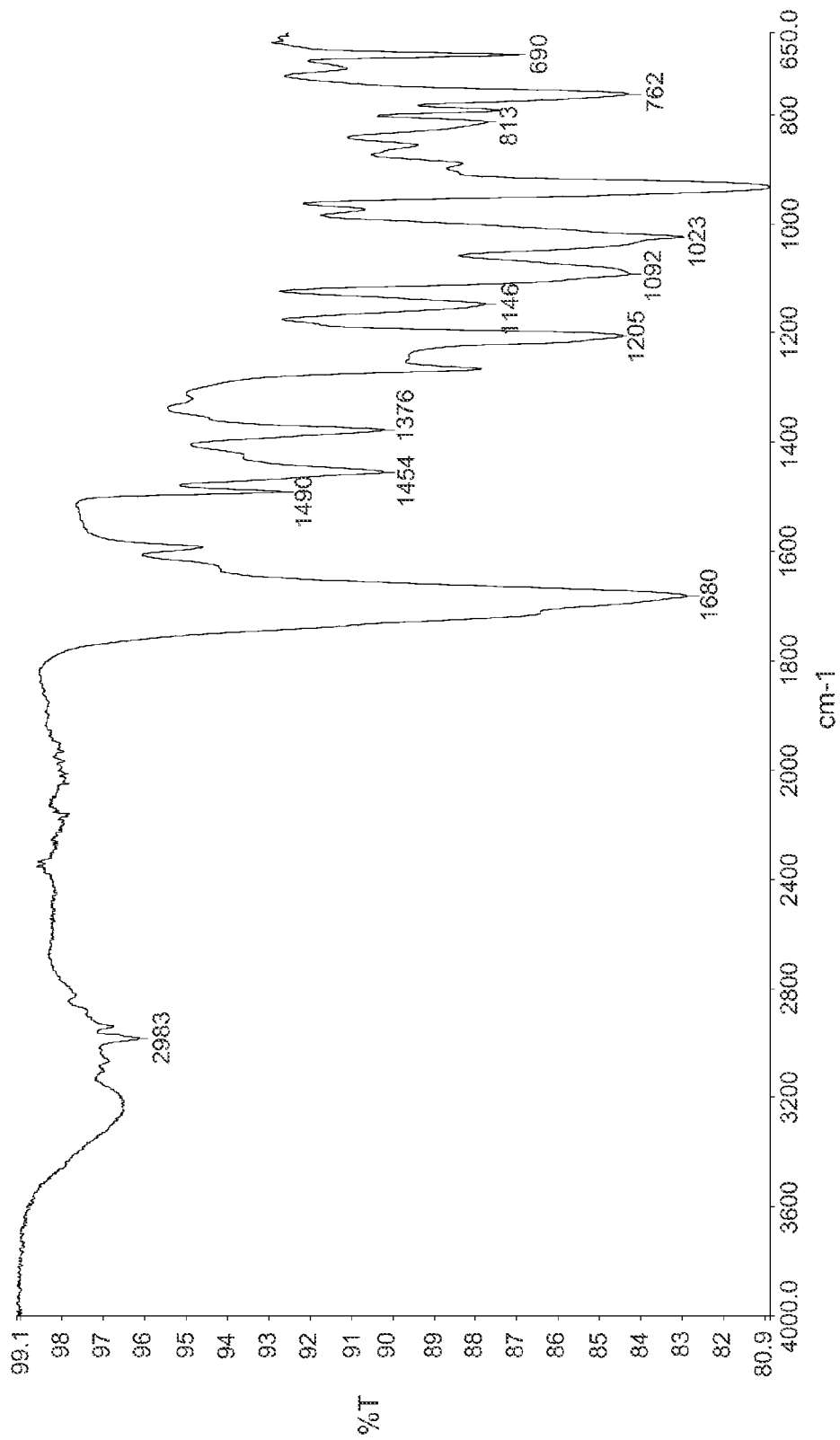
FIG. 14. FT-IR spectrum of 4.
Figure 16:
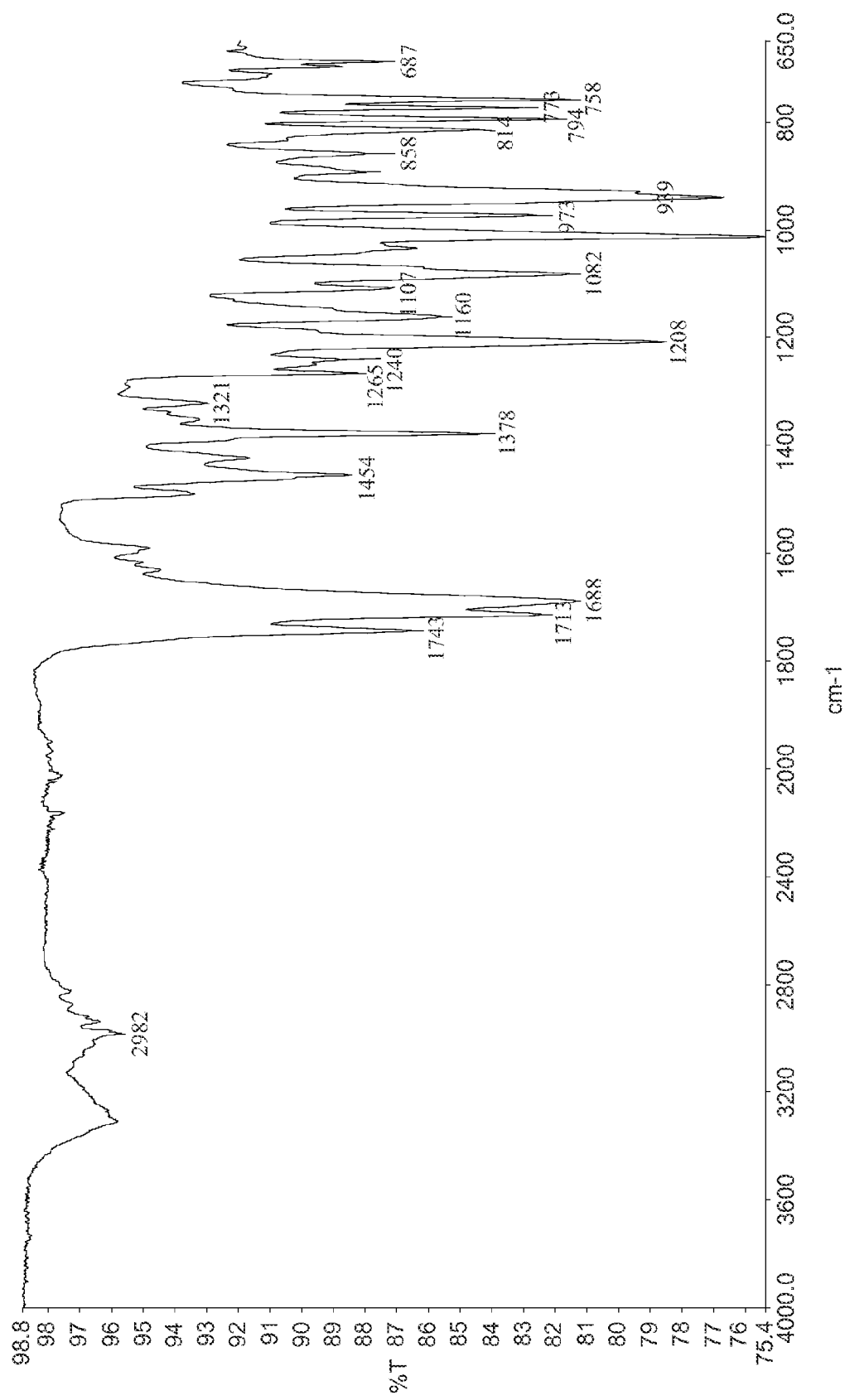
FIG. 16. FT-IR spectrum of $S_P$-4
FIG. 17. TGA and DSC analysis of 4.

The IR spectrum obtained for 4, $R_P$-4, and $S_P$-4 are shown in FIGS. 5-7, respectively. Selected peaks, in wavenumbers ($cm^{-1}$) are recited below:

4: ~1680, ~1454, ~1376, ~1205, ~1092, ~1023 (FIG. 14);
$R_P$-4: ~1742, ~1713, ~1679, ~1460, ~1377, ~1259, ~1157, ~1079 (FIG. 15); and
$S_P$-4 (Form 1): ~1743, ~1713, ~1688, ~1454, ~1378, ~1208, ~1082 (FIG. 16).

Example 25

Differential Scanning Calorimetry (DSC)
Thermo-Gravimetric Analysis (TGA)

DSC data were collected on a TA Instruments Q2000 equipped with a 50 position auto-sampler. The calibration for thermal capacity was carried out using sapphire and the calibration for energy and temperature was carried out using certified indium.

Modulated temperature DSC was carried out on typically 0.8-1.2 mg of each sample, in a pin-holed aluminum pan, using an underlying heating rate of 2° C.·$min^{-1}$ and temperature modulation parameters of ±0.2° C.·$min^{-1}$ and 40 seconds. A purge of dry nitrogen at 50 ml·$min^{-1}$ was maintained over the sample.

The instrument control software was Advantage for Q Series v2.8.0.392 and Thermal Advantage v4.8.3 and the data were analyzed using Universal Analysis v4.3A.

DSC data were collected on a Mettler DSC 823e equipped with a 34 position auto-sampler. The instrument was calibrated for energy and temperature using certified indium. Typically 0.8-1.2 mg of each sample, in a pin-holed aluminum pan, was heated at 10° C.·$min^{-1}$ from 25° C. to 250° C. A nitrogen purge at 50 ml·$min^{-1}$ was maintained over the sample. The instrument control and data analysis software was STARe v9.20.

TGA data were collected on a Mettler TGA/SDTA 851e equipped with a 34 position auto-sampler. The instrument was temperature calibrated using certified indium. Typically 8-12 mg of each sample was loaded onto a pre-weighed aluminum crucible and was heated at 10° C.·$min^{-1}$ from ambient temperature to 350° C. A nitrogen purge at 50 ml·$min^{-1}$ was maintained over the sample. The instrument control and data analysis software was STARe v9.20.

Figure 17:
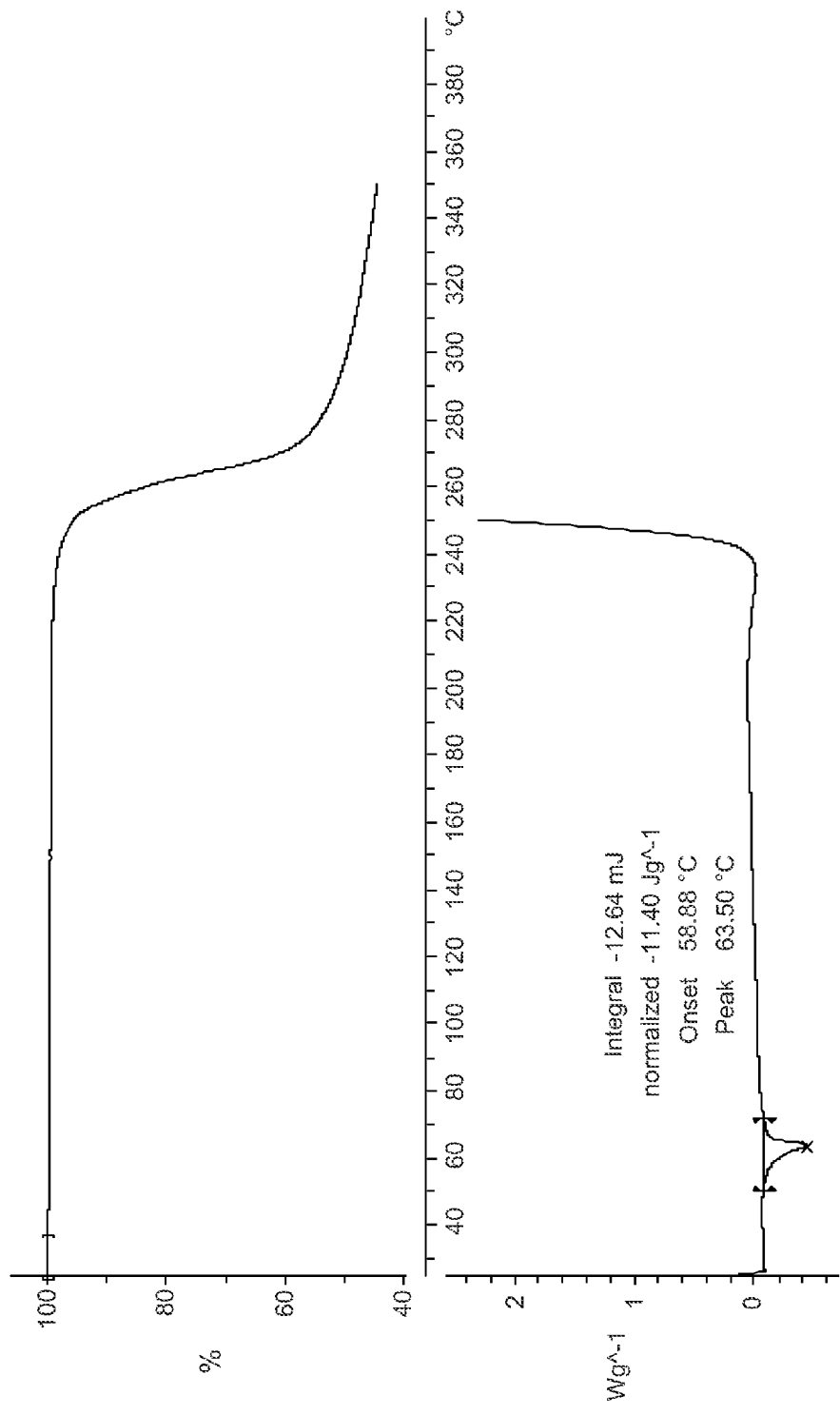

DSC analysis of 4 showed a single broad endotherm with an onset of 58.7° C. ($\Delta$H 14 J·$g^{-1}$) confirmed to be due to molecular relaxation during the glass transition by further modulated DSC analysis (FIG. 17). TGA analysis of 4 showed no weight loss before decomposition above 240° C., confirming the material to be non-solvated. As the XRPD analysis of 4 confirmed the material to be amorphous, modulated DSC analysis was undertaken in an attempt to calculate the glass transition temperature, which was found to be 57° C.

Figure 18:
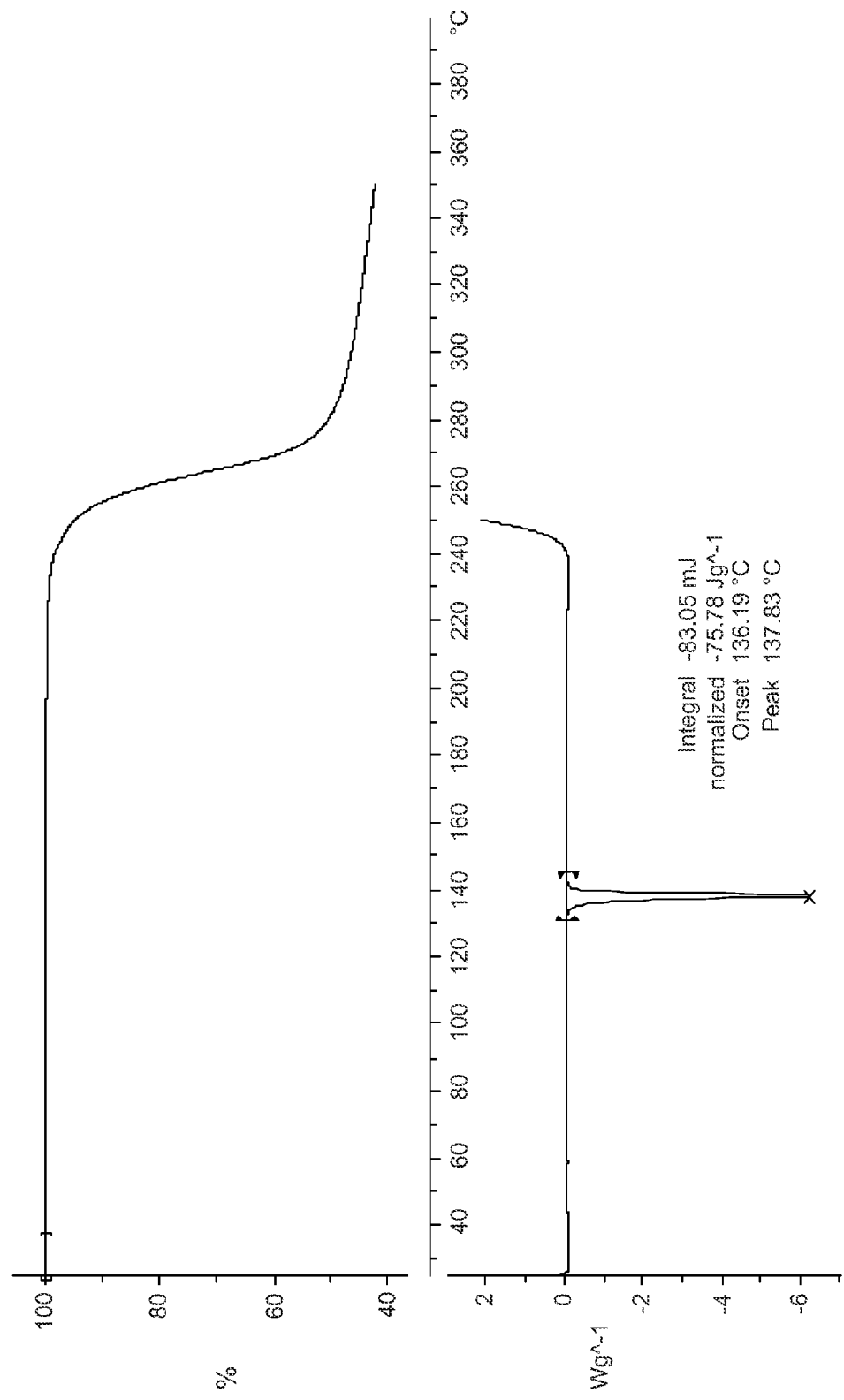
FIG. 18. TGA and DSC analysis of $R_P$-4.

DSC analysis showed a single sharp endotherm with an onset of 136.2° C. ($\Delta$H 76 J·$g^{-1}$) confirmed to be a melt by hot stage microscopy. See FIG. 18. TGA analysis of $R_P$-4 showed no weight loss before decomposition above 240° C., confirming the material to be non-solvated.

Figure 19:
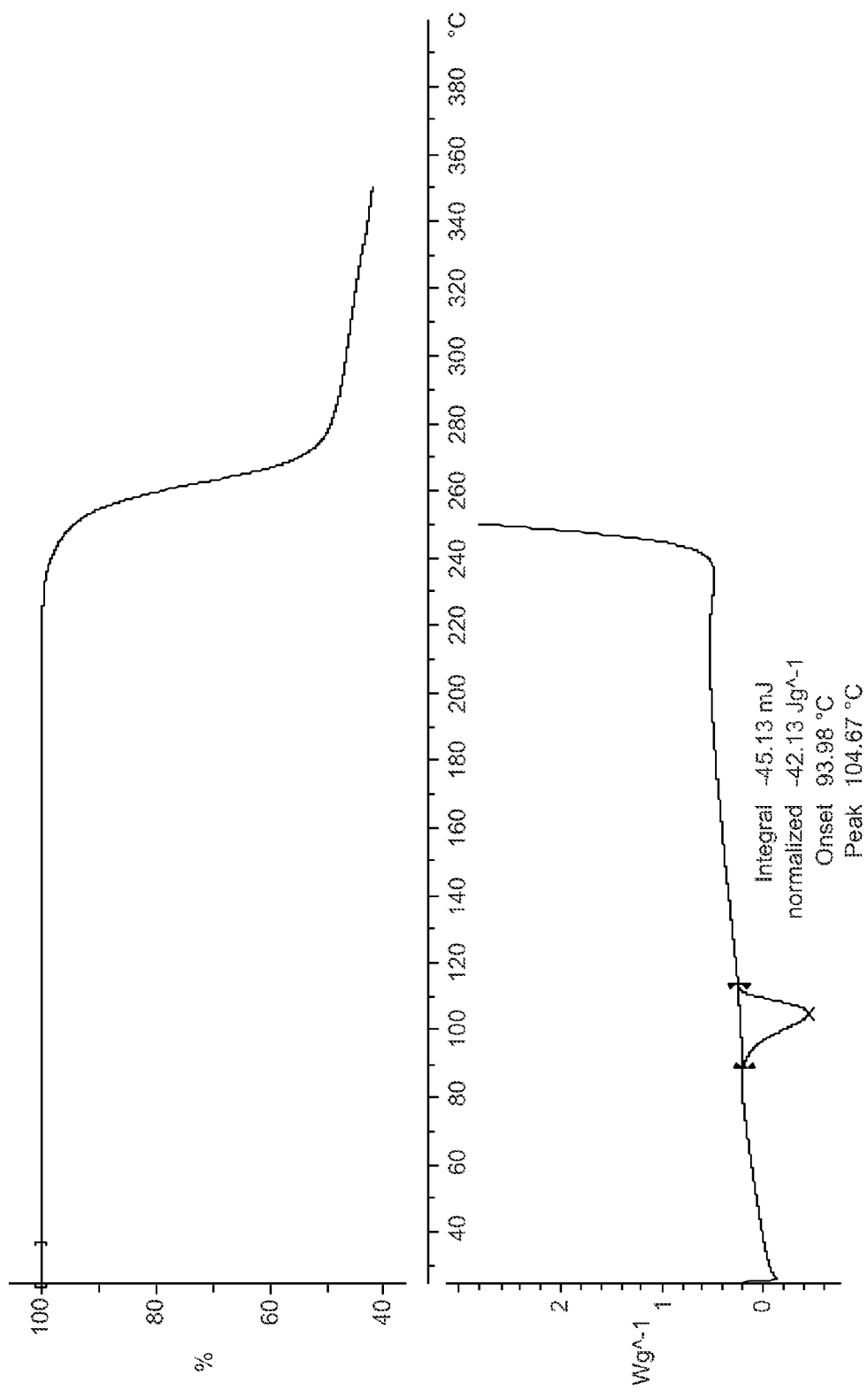
FIG. 19. TGA and DSC analysis of $S_P$-4.

DSC analysis of $S_P$-4 showed a single broad endotherm with an onset of 93.9° C. ($\Delta$H 43 J·$g^{-1}$) confirmed to a melt by hot stage microscopy. See FIG. 19. TGA analysis of $S_P$-4 showed no weight loss before decomposition above 240° C., confirming the material to be non-solvated.

Example 26

Gravimetric Vapour Sorption (GVS)

SMS DVS Intrinsic

Sorption isotherms were obtained using a SMS DVS Intrinsic moisture sorption analyzer, controlled by SMS Analysis Suite software. The sample temperature was maintained at 25° C. by the instrument controls. The humidity was controlled by mixing streams of dry and wet nitrogen, with a total flow rate of 200 ml·$min^{-1}$. The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg).

Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0.5-90% RH range.

TABLE 13

Method Parameters for SMS DVS Intrinsic Experiments

| Parameters | Values |
|---|---|
| Adsorption - Scan 1 | 40-90 |
| Desorption/Adsorption - Scan 2 | 90-0, 0-40 |
| Intervals (% RH) | 10 |
| Number of Scans | 2 |
| Flow rate (ml · $min^{-1}$) | 200 |
| Temperature (° C.) | 25 |
| Stability (° C. $min^{-1}$) | 0.2 |
| Sorption Time (hours) | 6 hour time out |

The sample was recovered after completion of the isotherm and re-analyzed by XRPD.

GVS analysis showed $R_P$-4 to be non-hygroscopic exhibiting reversible uptake of approximately 0.2 wt % of water from 0 to 90% relative humidity. Re-analysis of the sample by XRPD after the GVS experiment showed no change in form.

A sample of $S_P$-4 was ground with a pestle and mortar, and then successively passed through 500 and 250 μm sieves to yield the sample as a fine powder that was then analyzed using a modified single cycle method. The sample was taken from 40% RH (approximately ambient) to 60% RH, instead of 90% for the standard method, and then cycled to 0% and back to 40% RH. This analysis showed $S_P$-4 to be non-hygroscopic up to 60% RH, with reversible uptake of ~0.2% by weight of water from 0 to 60% RH.

Example 27

Thermodynamic Aqueous Solubility

Aqueous solubility was determined by suspending a sufficient amount of compound in water to give a maximum final concentration of ≥10 mg·ml$^{-1}$ of the parent free-form of the compound. The suspension was equilibrated at 25° C. for 24 hours then the pH was measured. The suspension was then filtered through a glass fiber C filter into a 96 well plate. The filtrate was then diluted by a factor of 101. Quantitation was by HPLC with reference to a standard solution of approximately 0.1 mg·ml$^{-1}$ in DMSO. Different volumes of the standard, diluted and undiluted sample solutions were injected. The solubility was calculated using the peak areas determined by integration of the peak found at the same retention time as the principal peak in the standard injection.

TABLE 14

HPLC Method Parameters for Solubility Measurements

| | | | |
|---|---|---|---|
| Type of method: | Reverse phase with gradient elution | | |
| Column: | Phenomenex Luna, C18 (2) 5 μm 50 × 4.6 mm | | |
| Column Temperature (° C.): | 25 | | |
| Standard Injections (μl): | 1, 2, 3, 5, 7, 10 | | |
| Test Injections (μl): | 1, 2, 3, 10, 20, 50 | | |
| Detection: Wavelength, Bandwidth (nm): | 260, 80 | | |
| Flow Rate (ml · min$^{-1}$): | 2 | | |
| Phase A: | 0.1% TFA in water | | |
| Phase B: | 0.085% TFA in acetonitrile | | |
| | Time (min) | % Phase A | % Phase B |
| Timetable: | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Analysis was performed under the above-noted conditions on an Agilent HP1100 series system equipped with a diode array detector and using ChemStation software vB.02.01-SR1.

TABLE 15

Aqueous solubility result for $R_P$-4, 4, and $S_P$-4.

| Sample ID | pH of Unfiltered mixture | Solubility/mg · ml$^{-1}$ | Comments |
|---|---|---|---|
| $R_P$-4 | 7.12 | 1.58 | Suspension |
| 4 | 7.03 | 6.11 | Residual solid |
| $S_P$-4 | 6.88 | 5.65 | Residual solid |

Example 28

Chemical Purity Determination by HPLC

Various HPLC conditions can be used to determine the chemical purity of the compounds disclosed herein. One such example is disclosed above in relation to the thermodynamic aqueous solubility studies. Another example is disclosed below.

HPLC Conditions:

| | |
|---|---|
| LC: | Waters Alliance 2695 Separations Module, Waters 2996 PDA detector and Waters Empower 2 Software (Version 6.00) |
| Column: | Phenomenex Luna C18(2); 4.6 × 50 mm; 3 μm |
| Flow rate: | 1.2 mL/min |
| Injection Volume: | 10 μL |
| Mobile phase: | Solvent A: 95% Water with 5% Methanol and 10 mM Ammonium Acetate; pH ~5.3 |
| | Solvent B: MeOH with 10 mM Ammonium Acetate |
| Gradient: | hold at 0% B      3 min |
| | 0-47% B           3-4 min |
| | hold at 47% B    4-10 min |
| | 47%-74% B        10-11 min |
| | hold at 74% B    11-13.5 min |
| | return to 0% B   13.5-13.6 min |
| | hold at 0% B     13.6-15.5 min |

Under these conditions, the purity of 4, $R_P$-4, and $S_P$-4 was determined to be ~99.6, ~99%, and ~99.5%, respectively. It is noted that higher purities can be realized by optimizing the methods disclosed above.

Inspection of the XRPD diffractograms shows that the two crystalline single diastereoisomers gave clearly different XRPD patterns. Additionally, there was a clear difference in the melting point of the two crystalline diastereoisomers, with $R_P$-4 having a considerably higher onset than $S_P$-4 (136° C. vs. 94° C.).

Example 29

Additional Separation Methods

The following SFC separation (conditions listed below) yielded adequate separation of a mixture of the diastereomers, $R_P$-4 and $S_P$-4.

| Preparative Method: | Analytical Method: |
|---|---|
| Chiralpak AS-H (2 × 25 cm) SN# 07-8656 | Chiralpak AS-H (25 × 0.46 cm) |
| 20% methanol/CO$_2$ (100 bar) 50 ml/min, 220 nm. Conc.: 260 mg/30 ml methanol, inj vol.: 1.5 ml | 20% methanol/CO$_2$ (100 bar) 3 ml/min, 220 nm. |

The following SFC separation (conditions listed below) yielded adequate separation of a mixture of the diastereomers, $R_P$-4 and $S_P$-4.

| Preparative Method: | Analytical Method: |
|---|---|
| Chiralpak IA(2 × 15 cm) 802091 | Chiralpak IA (15 × 0.46 cm) |
| 30% isopropanol(0.1% DEA)/CO$_2$, 100 bar | 40% methanol(DEA)/CO$_2$, 100 bar |
| 60 mL/min, 220 nm. | 3 mL/min, 220 nm. |
| inj vol.: 2 mL, 20 mg/mL methanol | |

TABLE 16

Summary of results from the batch characterization of R$_P$-4, 4, and S$_P$-4.

| Analysis | R$_P$-4 | 4 | S$_P$-4 |
|---|---|---|---|
| Proton NMR | Single diastereoisomer | 1:1 Mixture of diastereoisomers | Single diastereoisomer |
| XRPD | Crystalline - different | Amorphous | Crystalline - different |
| DSC | from S$_P$-4 Endotherm; melt - 136° C. | Endotherm; 59° C. | from R$_P$-4 Endotherm; melt - 94° C. |
| TGA | No wt loss, decomposition >240° C. | No wt loss, decomposition >240° C. | No wt loss, decomposition >240° C. |
| IR | See above | See above | See above |
| Aq Solubility (mg · ml$^{-1}$) | 1.58 | 6.11 | 5.65 |
| HPLC Purity | 96.9% | 99.6% | 99.5% |
| 40° C./75% RH | No form change | Deliquescence inside 1.5 h | Deliquescence inside 4.5 h |
| 25° C./53% RH | — | Deliquescence | No form change |
| GVS | Non-hygroscopic up to 90% RH | — | Non-hygroscopic up to 60% RH |

Example 30

X-Ray Crystallography of 8 (S$_P$-Isomer)

Figure 20A:
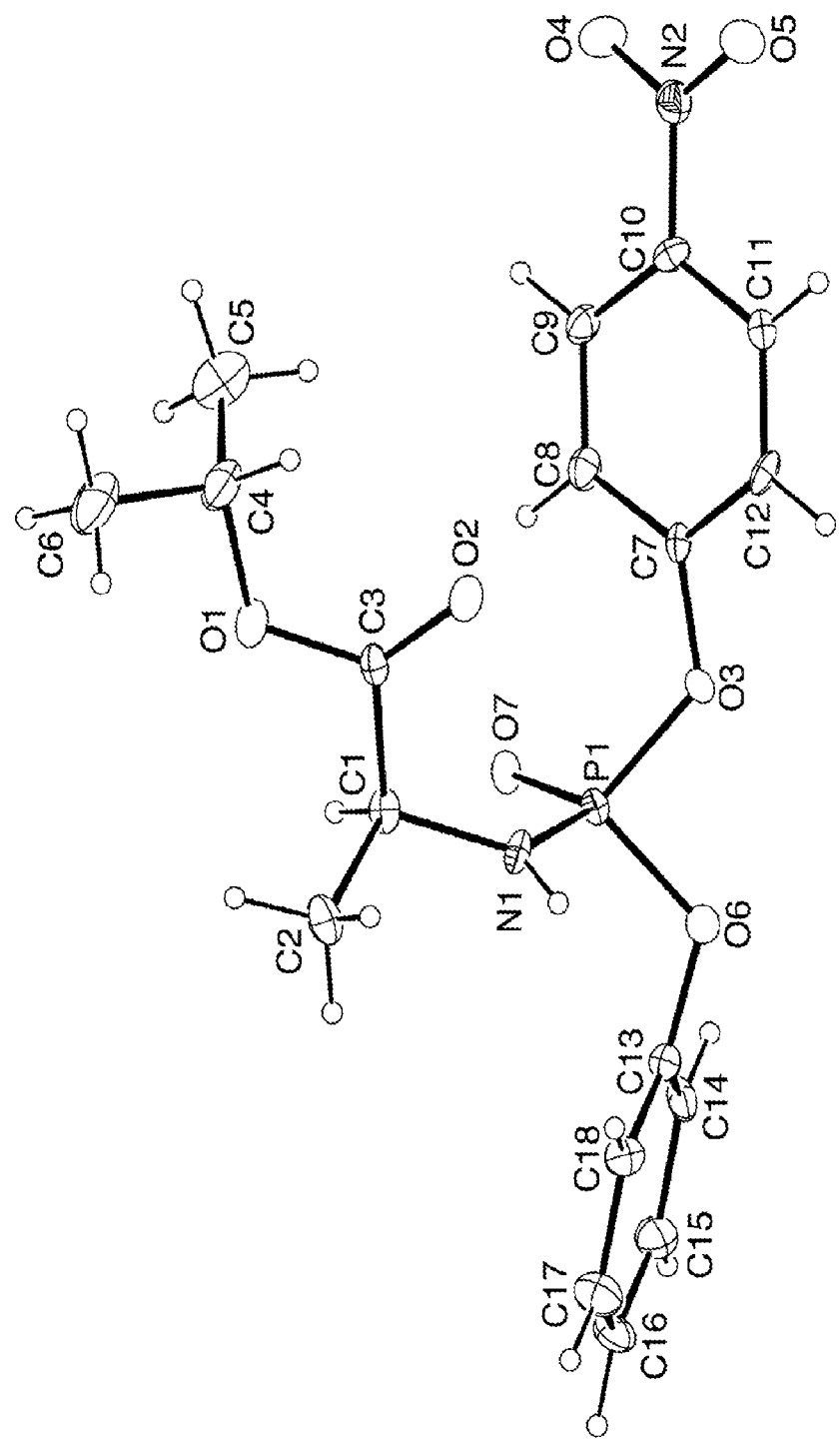
FIG. 20A. X-Ray Crystal Structure for 8 ($S_P$-isomer) (molecule no. 1 of the asymmetric unit).
Figure 20B:
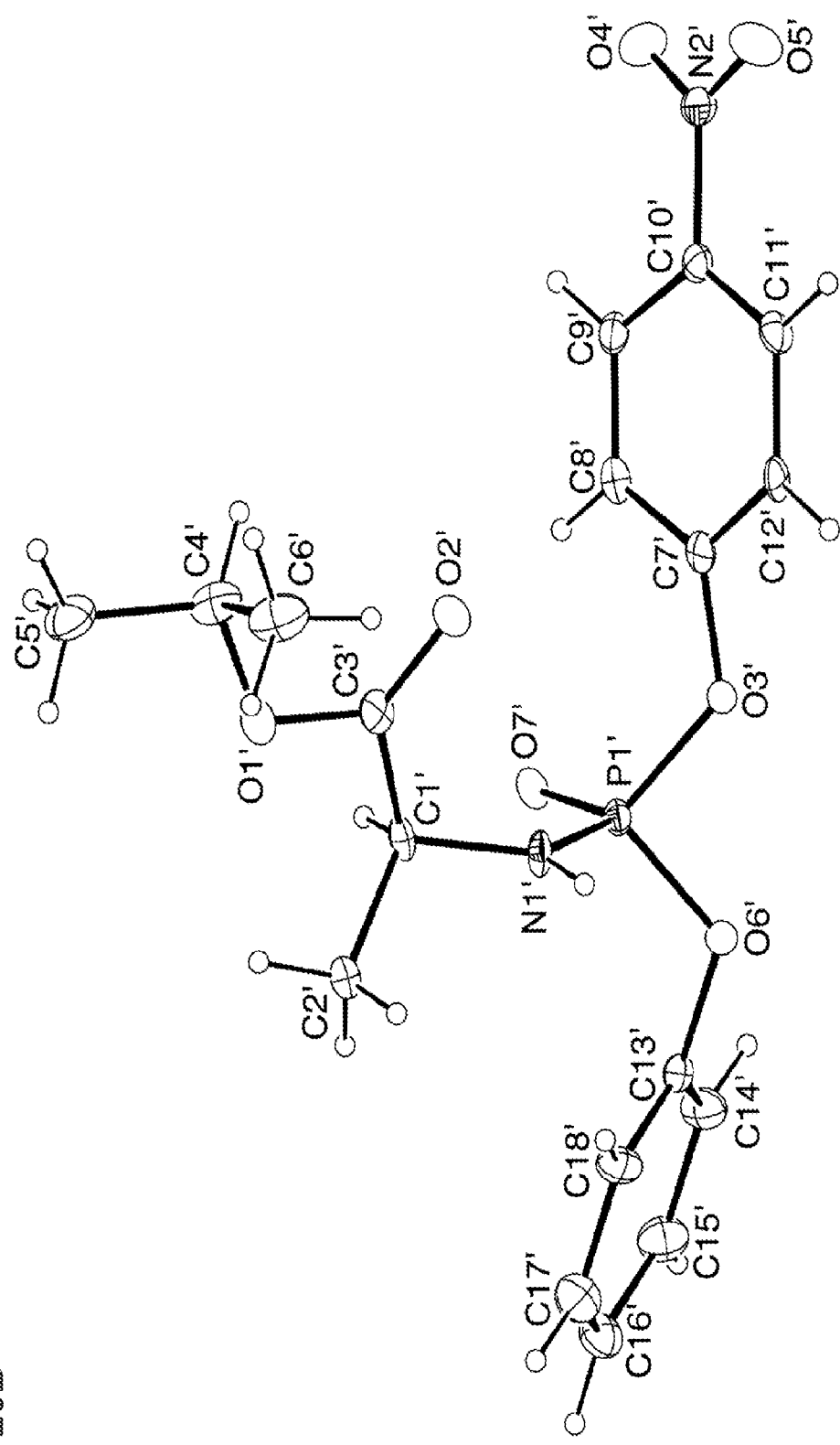
FIG. 20B. X-Ray Crystal Structure for 8 ($S_P$-isomer) (molecule no. 2 of the asymmetric unit).

Compound 8 (S$_P$-isomer), C$_{18}$H$_{21}$N$_2$PO$_7$, crystallizes in the monoclinic space group P2$_1$ (systematic absences 0k0: k=odd) with a=5.3312(4)Å, b=15.3388(8)Å, c=23.7807(13) Å, β=92.891(3)°, V=1942.2(2)Å$^3$, Z=4, and d$_{calc}$=1.397 g/cm$^3$. X-ray intensity data were collected on a Bruker APEXII CCD area detector employing graphite-monochromated Mo-Kα radiation (λ=0.71073 Å) at a temperature of 100(1)K. FIGS. 20A and 20B show molecules numbered 1 and 2, respectively, of the asymmetric unit.

Preliminary indexing was performed from a series of thirty-six 0.5° rotation frames with exposures of 30 seconds. A total of 3608 frames were collected with a crystal to detector distance of 70.00 mm, rotation widths of 0.5° and exposures of 20 seconds:

| scan type | 2θ | ω | φ | χ | frames |
|---|---|---|---|---|---|
| φ | −35.50 | 279.40 | 27.32 | 48.96 | 725 |
| φ | 24.50 | 22.31 | 35.56 | 69.08 | 692 |
| ω | −13.00 | 321.68 | 247.79 | 69.08 | 95 |
| φ | 34.50 | 204.08 | 28.21 | −92.80 | 293 |
| φ | −30.50 | 310.60 | 214.10 | 54.21 | 361 |
| φ | 32.00 | 304.67 | 24.47 | 50.72 | 722 |
| φ | −35.50 | 122.14 | 316.59 | −78.84 | 720 |

Rotation frames were integrated using SAINT (Bruker (2009) SAINT. Bruker AXS Inc., Madison, Wis., USA.) producing a listing of unaveraged F$^2$ and σ(F$^2$) values which were then passed to the SHELXTL (Bruker (2009) SHELXTL. Bruker AXS Inc., Madison, Wis., USA.) program package for further processing and structure solution on a Dell Pentium 4 computer. A total of 6909 reflections were measured over the ranges 1.58≤θ≤25.09°, −6≤h≤6, −18≤k≤18, −28≤l≤28 yielding 6909 unique reflections (Rint=0.0581). The intensity data were corrected for Lorentz and polarization effects and for absorption using SADABS (Sheldrick, G. M. (2007) SADABS. University of Gottingen, Germany.) (minimum and maximum transmission 0.6093, 0.7452).

The structure was solved by direct methods (SHELXS-97 (Sheldrick, G. M. (2008) Acta Cryst. A64, 112-122.)). Refinement was by full-matrix least squares based on F$^2$ using SHELXL-97 (Sheldrick, G. M. (2008) Acta Cryst. A64, 112-122.). All reflections were used during refinement. The weighting scheme used was w=1/[σ$^2$(F$_o^2$)+(0.0000P)$^2$+14.0738P] where P=(F$_o^2$+2F$_c^2$)/3. Non-hydrogen atoms were refined anisotropically and hydrogen atoms were refined using a riding model. Refinement converged to R1=0.0847 and wR2=0.1899 for 6173 observed reflections for which F>4σ(F) and R1=0.0963 and wR2=0.1963 and GOF=1.119 for all 6909 unique, non-zero reflections and 512 variables (R1=Σ||F$_o$|−|F$_c$||/Σ|F$_o$|; wR2=[Σw(F$_o^2$−F$_c^2$)$^2$/Σw(F$_o^2$)$^2$]$^{1/2}$; GOF=[Σw(F$_o^2$−F$_c^2$)$^2$/(n−p)]$^{1/2}$; where n=the number of reflections and p=the number of parameters refined). The maximum Δ/σ in the final cycle of least squares was 0.000 and the two most prominent peaks in the final difference Fourier were +0.402 and −0.559 e/Å$^3$.

TABLE 17

Summary of Structure Determination of Compound 8 (S$_P$-isomer)

| Empirical formula | C$_{18}$H$_{21}$N$_2$PO$_7$ |
|---|---|
| Formula weight | 408.34 |
| Temperature | 100(1) K |
| Wavelength | 0.71073 Å |
| Crystal system | monoclinic |
| Space group | P2$_1$ |
| Cell constants: | |
| a | 5.3312(4) Å |
| b | 15.3388(8) Å |
| c | 23.7807(13) Å |
| β | 92.891(3)° |
| Volume | 1942.2(2) Å$^3$ |
| Z | 4 |
| Density (calculated) | 1.397 Mg/m$^3$ |
| Absorption coefficient | 0.185 mm$^{-1}$ |
| F(000) | 856 |
| Crystal size | 0.40 × 0.10 × 0.08 mm$^3$ |
| Theta range for data collection | 1.58 to 25.09° |
| Index ranges | −6 ≤ h ≤ 6, −18 ≤ k ≤ 18, −28 ≤ l ≤ 28 |
| Reflections collected | 6909 |
| Independent reflections | 6909 [R(int) = 0.0581] |

TABLE 17-continued

Summary of Structure Determination of Compound 8 ($S_P$-isomer)

| | |
|---|---|
| Completeness to theta = 25.09° | 99.6% |
| Absorption correction | Semi-empirical from equivalents |
| Max. and min. transmission | 0.7452 and 0.6093 |
| Refinement method | Full-matrix least-squares on $F^2$ |
| Data/restraints/parameters | 6909/1/512 |
| Goodness-of-fit on $F^2$ | 1.119 |
| Final R indices [I > 2sigma(I)] | R1 = 0.0847, wR2 = 0.1899 |
| R indices (all data) | R1 = 0.0963, wR2 = 0.1963 |
| Absolute structure parameter | 0.1(2) |
| Largest diff. peak and hole | 0.402 and −0.559 e · Å$^{-3}$ |

Example 31

Biological Activity

Replicon containing cells were seeded at either 3,000 cells/well (50 µL) in 96-well white/opaque plates, or 1,500 cells/well (25 µL) in 384-well white/opaque plates. 50 µL of 2× compound were added in the 96 well plate or 25 µL of 2× compound were added in the 384 well plate. The plates were incubated at 37° C. in a humidified 5% $CO_2$ atmosphere for 4 days. After incubation, Bright-Glo reagent (50 µL for 96-well plate, or 25 µL for 384-well plate) was added to measure the firefly luciferase reporter for HCV replication. Percent inhibition was calculated against the no drug control.

| Compound | HCV Replicon Activity (µM) |
|---|---|
| 4 | 0.58 |
| $R_P$-4 | 2.87 |
| $S_P$-4 | 0.13 |

$R_P$-4 and $S_P$-4 have been demonstrated to have broad genotype coverage. For example, both have been shown to be active against hepatitis C virus, genotypes 1-4.

The subject matter of U.S. patent application Ser. No. 12/053,015 and U.S. Provisional Patent Application Nos. 61/179,923, filed May 20, 2009, and 61/319,513, filed Mar. 31, 2010, are hereby incorporated by reference in their entireties. The subject matter of all cited references is hereby incorporated by reference. In the event that the meaning of an incorporated term conflicts with the meaning of a term defined herein, the meaning of the terms contained in the present disclosure control over the meaning of the incorporated terms.

The invention claimed is:

1. A diastereoselective process for preparing (Sp-4):

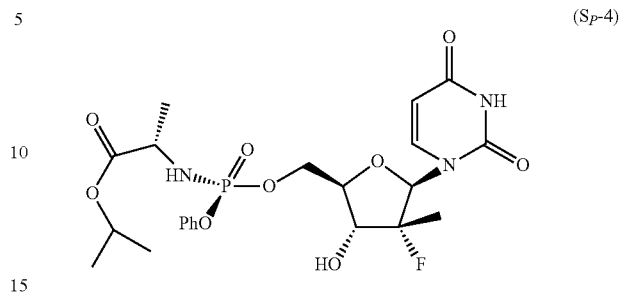

(Sp-4)

comprising:
i) reacting compound C:

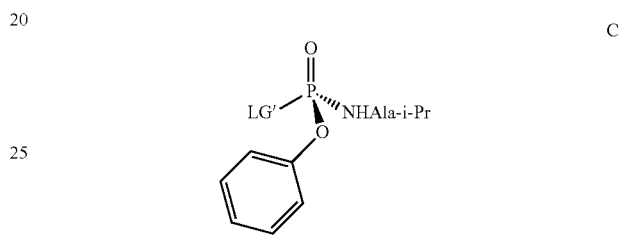

C wherein LG' is p-nitrophenoxide, 2,4-dinitrophenoxide or pentafluorophenoxide with a basic reagent and compound 3:

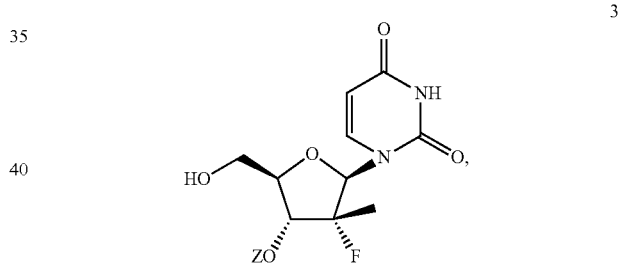

3 wherein Z is hydrogen, to obtain Sp-4; or
ii) reacting compound C with a basic reagent and compound 3, wherein Z is a protecting group, and deprotecting to obtain $S_P$-4.

2. The process of claim 1, wherein Z is hydrogen.
3. The process of claim 1, wherein no chromatography is performed.
4. The process of claim 1, wherein LG' is p-nitrophenoxide.
5. The process of claim 1, wherein LG' is pentafluorophenoxide.

* * * * *

UNITED STATES PATENT AND TRADEMARK OFFICE
CERTIFICATE OF CORRECTION

PATENT NO. : 9,637,512 B2
APPLICATION NO. : 14/152243
DATED : May 2, 2017
INVENTOR(S) : Byoung-Kwon Chun et al.

Page 1 of 1

It is certified that error appears in the above-identified patent and that said Letters Patent is hereby corrected as shown below:

In the Claims

In Claim 1, Column 78, Line 2, please replace "for preparing (Sp-4)" with --for preparing ($S_p$-4)--.

In Claim 1, Column 78, Lines 34-44, please replace

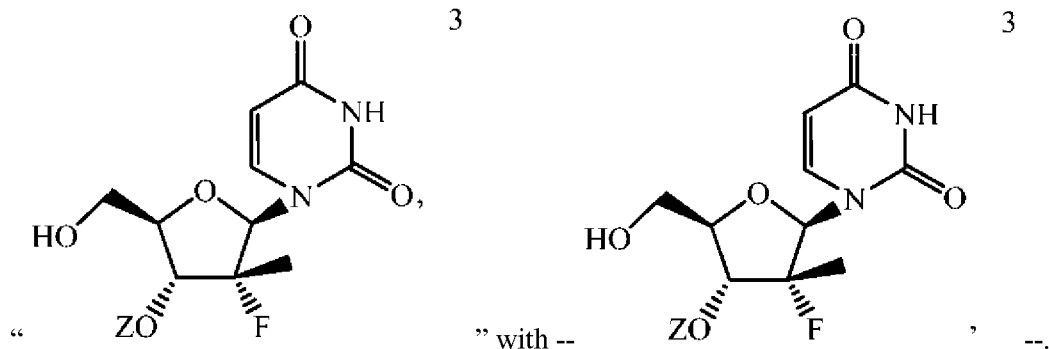

" with -- ... , --.

In Claim 1, Column 78, Line 45, please replace "to obtain Sp-4;" with --to obtain ($S_p$-4);--.

In Claim 1, Column 78, Line 48, please replace "to obtain S$p$-4." with --to obtain ($S_p$-4).--.

Signed and Sealed this
Twentieth Day of February, 2018

Andrei Iancu
*Director of the United States Patent and Trademark Office*